United States Patent
Liang et al.

(10) Patent No.: US 9,422,309 B2
(45) Date of Patent: Aug. 23, 2016

(54) 3-O-HETEROARYL-INGENOL

(71) Applicant: LEO LABORATORIES LIMITED, Dublin (IE)

(72) Inventors: Xifu Liang, Ballerup (DK); Thomas Högberg, Ballerup (DK); Bjarne Nørremark, Ballerup (DK); Kristoffer Månsson, Ballerup (DK); Carsten Ryttersgaard, Ballerup (DK); Gunnar Grue-Sørensen, Roskilde (DK)

(73) Assignee: LEO LABORATORIES LIMITED, Dublin (IE)

( * ) Notice: Subject to any disclaimer, the term of this patent is extended or adjusted under 35 U.S.C. 154(b) by 0 days.

(21) Appl. No.: 14/409,374

(22) PCT Filed: Jun. 21, 2013

(86) PCT No.: PCT/EP2013/062995
§ 371 (c)(1),
(2) Date: Dec. 18, 2014

(87) PCT Pub. No.: WO2014/001215
PCT Pub. Date: Jan. 3, 2014

(65) Prior Publication Data
US 2015/0175622 A1 Jun. 25, 2015

Related U.S. Application Data

(60) Provisional application No. 61/664,398, filed on Jun. 26, 2012, provisional application No. 61/763,206, filed on Feb. 11, 2013.

(51) Int. Cl.

| C07D 495/04 | (2006.01) |
| A61K 31/4164 | (2006.01) |
| A61K 31/416 | (2006.01) |
| A61K 31/4245 | (2006.01) |
| A61K 31/4355 | (2006.01) |
| A61K 31/44 | (2006.01) |
| A61K 31/47 | (2006.01) |
| A61K 31/506 | (2006.01) |
| C07D 213/84 | (2006.01) |
| C07D 215/22 | (2006.01) |
| C07D 231/56 | (2006.01) |

(Continued)

(52) U.S. Cl.
CPC .............. *C07D 495/04* (2013.01); *A61K 8/49* (2013.01); *A61K 8/4926* (2013.01); *A61K 8/4946* (2013.01); *A61K 8/4953* (2013.01); *A61K 31/416* (2013.01); *A61K 31/4164* (2013.01); *A61K 31/42* (2013.01); *A61K 31/423* (2013.01); *A61K 31/4245* (2013.01); *A61K 31/4355* (2013.01); *A61K 31/4365* (2013.01); *A61K 31/44* (2013.01); *A61K 31/47* (2013.01); *A61K 31/472* (2013.01); *A61K 31/505* (2013.01); *A61K 31/506* (2013.01); *A61K 45/06* (2013.01); *A61Q 19/08* (2013.01); *C07D 213/64* (2013.01); *C07D 213/84* (2013.01); *C07D 215/22* (2013.01); *C07D 217/24* (2013.01); *C07D 231/56* (2013.01); *C07D 233/70* (2013.01); *C07D 239/34* (2013.01); *C07D 261/20* (2013.01); *C07D 271/06* (2013.01); *C07D 271/07* (2013.01); *C07D 491/00* (2013.01); *C07D 491/048* (2013.01); *C07D 495/00* (2013.01)

(58) Field of Classification Search
None
See application file for complete search history.

(56) References Cited

U.S. PATENT DOCUMENTS 4,716,179 A 12/1987 Hecker et al.

FOREIGN PATENT DOCUMENTS

| EP | 0013983 A2 | 8/1980 |
| EP | 0013983 A3 | 8/1980 |
| WO | WO 99/08994 A1 | 2/1999 |

OTHER PUBLICATIONS

Appendino et al., "Synthesis of Modified Ingenol Esters," European Journal of Organic Chemistry, vol. 1999, Dec. 1999, available online Nov. 15, 1999, pp. 3413-3420.

(Continued)

*Primary Examiner* — Samantha Shterengarts
(74) *Attorney, Agent, or Firm* — Birch, Stewart, Kolasch & Birch, LLP

(57) ABSTRACT

The present invention relates to a compound according to formula (I) wherein $R_1$ represents optionally substituted heteroaryl, and pharmaceutically acceptable salts, hydrates, solvates or pharmaceutically acceptable and physiologically cleavable esters thereof. The invention relates further to intermediates for the preparation of said compounds, to said compounds for use in therapy, to pharmaceutical compositions comprising said compounds, to methods of treating diseases, e.g. diseases associated with hyperplasia, neoplasia or dysplasia, with said compounds, to methods of treatment of cosmetic indications with said compounds, and to the use of said compounds in the manufacture of medicaments.

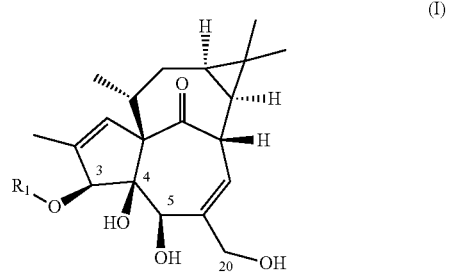

19 Claims, No Drawings

(51) Int. Cl.

| | | |
|---|---|---|
| C07D 233/70 | (2006.01) | |
| C07D 239/34 | (2006.01) | |
| C07D 261/20 | (2006.01) | |
| C07D 491/00 | (2006.01) | |
| C07D 271/06 | (2006.01) | |
| C07D 495/00 | (2006.01) | |
| C07D 213/64 | (2006.01) | |
| A61K 45/06 | (2006.01) | |
| A61K 31/472 | (2006.01) | |
| A61K 31/505 | (2006.01) | |
| A61K 8/49 | (2006.01) | |
| A61K 31/42 | (2006.01) | |
| A61K 31/423 | (2006.01) | |
| A61K 31/4365 | (2006.01) | |
| A61Q 19/08 | (2006.01) | |
| C07D 217/24 | (2006.01) | |
| C07D 271/07 | (2006.01) | |
| C07D 491/048 | (2006.01) | |

(56) References Cited

OTHER PUBLICATIONS

Blanco-Molina et al., "Ingenol esters induce apoptosis in Jurkat cells through an AP-1 and NF-κB independent pathway," Chemistry & Biology, vol. 8, 2001, available online Jun. 26, 2001, pp. 767-778.

Challacombe et al., "Neutrophils Are a Key Component of the Anti-tumor Efficacy of Topical Chemotherapy with Ingenol-3-Angelate," The Journal of Immunology, vol. 177, 2006, pp. 8123-8132.

Cozzi et al., "Induction of Senescence in Diterpene Ester-Treated Melanoma Cells via Protein Kinase C-Dependent Hyperactivation of the Mitogen-Activated Protein Kinase Pathway," Cancer Research, vol. 66, No. 20, Oct. 15, 2006, pp. 10083-10091.

Ersvaer et al., "The Protein Kinase C Agonist PEP005 (Ingenol 3-Angelate) in the Treatment of Human Cancer: A Balance between Efficacy and Toxicity," Toxins, vol. 2, 2010, pp. 174-194.

Hampson et al., "PEP005, a selective small-molecule activator of protein kinase C, has potent antileukemic activity mediated via the delta isoform of PKC," Blood, vol. 106, No. 4, Aug. 2005, available online Apr. 21, 2005, pp. 1362-1368.

Hampson et al., "The anti-tumor agent, ingenol-3-angelate (PEP005), promotes the recruitment of cytotoxic neutrophils by activation of vascular endothelial cells in a PKC-δdependent manner," Cancer Immunology, Immunotherapy, vol. 57, 2008, available online Feb. 12, 2008, pp. 1241-1251.

Le et al., "Immunostimulatory cancer chemotherapy using local ingenol-3-angelate and synergy with immunotherapies," Vaccine, vol. 27, 2009, pp. 3053-3062.

Ogbourne et al., "Antitumor Activity of 3-Ingenyl Angelate : Plasma Membrane and Mitochondrial Disruption and Necrotic Cell Death," Cancer Research, vol. 64, Apr. 15, 2004, pp. 2833-2839.

Rosen et al., "Dual mechanism of action of ingenol mebutate gel for topical treatment of actinic keratoses: Rapid lesion necrosis followed by lesion-specific immune response," Journal of the American Academy of Dermatology, vol. 66, No. 3, 2012, available online Nov. 7, 2011, pp. 486-493.

3-O-HETEROARYL-INGENOL

CROSS REFERENCE TO RELATED APPLICATIONS

This application is the National Phase of PCT International Application No. PCT/EP2013/062995, filed on Jun. 21, 2013, which claims priority under 35 U.S.C. 119(e) to U.S. Provisional Application Nos. 61/664,398 and 61/763,206, filed on Jun. 26, 2012 and Feb. 11, 2013 respectively, all of which are hereby expressly incorporated by reference into the present application.

FIELD OF THE INVENTION

This invention relates to novel derivatives of 3-O-heteroaryl-ingenol, to intermediates for the preparation thereof, to said compounds for use in therapy, to pharmaceutical compositions comprising said compounds, to methods of treating diseases with said compounds, and to the use of said compounds in the manufacture of medicaments.

BACKGROUND OF THE INVENTION

Ingenol-3-angelate (PEP005, ingenol mebutate, Picato®) is a diterpene-ester of the ingenol family which is isolated from various *Euphorbia* species, particularly from *Euphorbia peplus*. The compound has been launched for the treatment of actinic keratosis and is presently subject for clinical development for non-melanoma skin cancer.

WO99/08994 describes isolation of compounds from *Euphorbia* plant and their use in cancer and other neoplastic diseases hereunder actinic keratosis or solar keratosis.

WO 2012/085189, WO 2012/083954 and WO 2012/083953 describe ingenol-3-acylates and ingenol-3-carbamates which stimulate neutrophil oxidative burst, stimulate keratinocyte IL-8 release or which induce rapid necrosis.

Sorg et. al. Z Naturforsch. 37b, 1640-7 (1982) has described 3-O-(2-methoxyethoxy)methyl-ingenol as an intermediate in the preparation of ingenol derivatives.

Ingenol-3-angelate is believed to have a dual mode of action: 1) Induction of cell death by direct cytotoxicity or induction of apoptosis and 2) an immunostimulatory effect dominated by neutrophil recruitment and activation (Rosen, R. H., et al., *J Am Acad Derm* (2012), 66, 486-493; Ersvaer, E., et al., *Toxins*, (2010), 2, 174-194). Nanomolar concentrations of the agent cause activation and modulation of protein kinase C (PKC) classical and novel isoforms, with particular importance of PKCdelta. Through activation of PKCdelta the agent induces apoptosis in susceptible cells (Hampson, P., et al., *Blood*, (2005), 106, 1362-1368; Cozzi, S. J., et al., *Cancer Res*, (2006), 66, 10083-10091). Rapid cytotoxicity on cancer cells is observed at high micromolar concentrations (Ogbourne, S. M., et al., *Cancer Res* (2004), 64, 2833-2839). Through activation of various PKC isoforms the agent also induces pro-inflammatory effects, including release of pro-inflammatory mediators (Challacombe, J. M., et al., *J Immunol* (2006), 177, 8123-8132, activation of vascular endothelium (Hampson, P., et al., *Cancer Immunol Immunother*, (2008), 57, 1241-1251); chemoattraction of neutrophils through induction of interleukin 8 in keratinocytes and development of specific anti-cancer immune responses by CD8+ cells through adjuvant properties in animal models (Le, T. T., et al., *Vacccine*, (2009), 27, 3053-3062).

Compounds exerting dual mode of action by induction of cell death by direct cytotoxicity or induction of apoptosis, and by an immunostimulatory effect involving neutrophil recruitment and activation, may be useful for treatment of conditions associated with hyperplasia, neoplasia or dysplasia. Compounds inducing cell death by primary and/or secondary necrosis and compounds exhibiting a pro-apoptotic effect may reduce unwanted cell growth and remove unwanted cells, and furthermore, stimulation of the innate immune response and adjuvant effects may augment the biological response against aberrant or transformed cells.

Compounds inducing cell death by primary and/or secondary necrosis may be useful for treatment of cosmetic conditions, as these compounds may kill or remove unwanted tissue or cells.

There is a continuous need to find new ingenol derivatives which induce cell death by cytotoxicity or apoptosis and/or induce an immunostimulatory effect.

SUMMARY OF THE INVENTION

The present invention provides 3-O-heteroaryl-ingenol derivatives which may for example be useful for treatment of conditions associated with the use of ingenol-3-angelate or useful for treatment of conditions which are affected by induction of cell death by cytotoxicity or induction of apoptosis and/or by an immunostimulatory effect.

Compounds of the present invention stimulate neutrophil oxidative burst, which is part of the innate immune response.

Compounds of the present invention stimulate keratinocyte IL-8 release, thus inducing an immunostimulatory effect.

Some compounds of the present invention induce rapid necrosis.

Some compounds of the present invention exhibit favorable stability properties.

Accordingly, the present invention relates to a compound according to general formula I

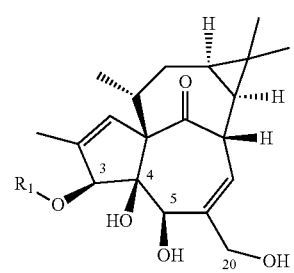

wherein $R_1$ represents heteroaryl, and wherein $R_1$ is optionally substituted with one or more substituents independently selected from $R_2$;

wherein $R_2$ represents cyano or halogen;

or $R_2$ represents $(C_1-C_6)$alkyl, $(C_2-C_6)$alkenyl, $(C_1-C_6)$alkoxy, $(C_3-C_6)$cycloalkyl, halo$(C_1-C_6)$alkyloxy, heterocycloalkyl, aryl or heteroaryl; said $(C_1-C_6)$alkyl optionally being substituted with one or more substituents independently selected from the group consisting of halogen, cyano, hydroxyl and oxo;

or $R_2$ represents $-NR_aCOR_b$, $-CONR_aR_b$, $-COOR_a$, $-OCOR_a$, $-OR_a$, $-OCONR_aR_b$, $-NR_aCOOR_b$, $-NR_aSO_2R_b$, $-SO_2NR_aR_b$, $-SO_2R_a$, $-S(O)R_a$ or $-NR_aR_b$;

wherein $R_a$ and $R_b$ are each independently selected from the group consisting of hydrogen, $(C_1-C_4)$alkyl, halo$(C_1-C_4)$alkyl, hydroxy$(C_1-C_4)$alkyl, cyano$(C_1-C_4)$alkyl, aryl, heteroaryl, $(C_3-C_6)$cycloalkyl and heterocycloalkyl;

or two adjacent R$_2$'s join together to form a 5-7 membered non-aromatic carbocyclic or heterocyclic ring together with the carbon or nitrogen atoms to which they are attached; and pharmaceutically acceptable salts, hydrates, solvates or pharmaceutically acceptable and physiologically cleavable esters thereof.

In another aspect, the invention relates to a compound according to formula I, for use as a medicament in therapy.

In yet another aspect, the invention relates to a compound according to formula I for use in the treatment, prevention, amelioration or prophylaxis of physiological disorders or diseases associated with hyperplasia, neoplasia or dysplasia.

In yet another aspect, the invention relates to use of a compound according to formula I for the manufacture of a pharmaceutical medicament.

In yet another aspect, the invention relates to a method of preventing, treating, amelioration or prophylaxis of physiological disorders or diseases associated with hyperplasia, neoplasia or dysplasia by administration to a subject in need thereof a compound according to formula I, optionally together with a pharmaceutically acceptable carrier or one or more excipients, optionally in combination with other therapeutically active compounds.

In yet another aspect, the invention relates to a compound according to formula I for use in the treatment or amelioration of cosmetic indications.

In yet another aspect, the invention relates to a method of treatment or amelioration of cosmetic indications by administration to a subject in need thereof a compound according to formula I, optionally together with a pharmaceutically acceptable carrier or one or more excipients, optionally in combination with other therapeutically active compounds.

In yet another aspect, the invention relates to a pharmaceutical composition comprising a compound according to formula I or a pharmaceutically acceptable stereoisomer, salt or in vivo hydrolysable ester thereof together with a pharmaceutically acceptable vehicle or excipient.

In yet another aspect, the invention relates to a pharmaceutical composition comprising a compound according to formula I or a pharmaceutically acceptable stereoisomer, salt or in vivo hydrolysable ester thereof in combination with one or more other therapeutically active agents.

In still a further aspect, the invention relates to intermediate compounds useful for the synthesis of compounds according to formula I.

DETAILED DESCRIPTION OF THE INVENTION

Definitions

The term "alkenyl" is intended to indicate a straight or branched hydrocarbon radical comprising 2-6 carbon atoms, such as 2-4 carbon atoms, and having from 1-3 carbon-carbon double bonds, e.g. ethenyl, propenyl (allyl), methylbutenyl, butenyl, pentenyl or hexenyl.

The term "alkyl" is intended to indicate a radical obtained when one hydrogen atom is removed from a branched or linear hydrocarbon. Said alkyl comprises 1-6, preferably 1-4, such as 1-3, such as 2-3 or such as 1-2 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, n-pentyl, isopentyl, neopentyl, n-hexyl and isohexyl.

The terms "alkyloxy" and "alkoxy" are intended to indicate a radical of the formula —OR', wherein R' is alkyl as indicated herein, wherein the alkyl group is appended to the parent molecular moiety through an oxygen atom, e.g. methoxy (—OCH$_3$), ethoxy (—OCH$_2$CH$_3$), n-propoxy, isopropoxy, butoxy, tert-butoxy, and the like.

The term "aryl" is intended to indicate a radical of aromatic carbocyclic rings comprising 6-13 carbon atoms, such as 6-9 carbon atoms, such as 6 carbon atoms, in particular 5- or 6-membered rings, including fused carbocyclic rings with at least one aromatic ring. If the aryl group is a fused carbocyclic ring, the point of attachment of the aryl group to the parent molecular moiety may be through an aromatic or through an alifatic carbon atom within the aryl group. Representative examples of aryl include, but are not limited to phenyl, naphthyl, indenyl, indanyl, dihydronaphtyl, tetrahydronaphtyl and fluorenyl.

The term "cyano" is intended to indicate a —CN group attached to the parent molecular moiety through the carbon atom.

The term "cycloalkyl" is intended to indicate a saturated cycloalkane hydrocarbon radical, including polycyclic radicals such as bicyclic or tricyclic radicals, comprising 3-10 carbon atoms, preferably 3-8 carbon atoms, such as 3-6 carbon atoms, such as 3-5 carbon atoms or such as 3-4 carbon atoms, e.g. cyclopropyl, cyclobutyl, cyclopentyl, cyclohexyl, or cycloheptyl, adamantly and cubanyl.

The term "dihydroxyl protective group" is intended to indicate any group which forms a derivative of a diol which is stable to the projected reactions wherein said dihydroxyl protective group subsequently optionally can be selectively removed. Said dihydroxyl derivative can be obtained by selective reaction of a dihydroxyl protecting agent with a diol.

Ketal derivatives, such as isopropylidene ketal (acetonide), cyclopentylidene ketal, cyclohexylidene ketal, cycloheptylidene ketal, benzophenone ketal, 1-tert-butylethylidene ketal or 1-phenylethylidene ketal, 3-pentylidene ketal, 2,4-dimethyl-3-pentylidene ketal, 2,6-dimethyl-4-heptylidene ketal, 3,3-dimethyl-2-butylidene ketal; and acetal derivatives such as benzylidene acetal, 2,4-dimethoxybenzylidene acetal, 4-nitrobenzylidene acetal, 2,4,6-trimethylbenzylidene acetal, 2,2-dimethyl-1-propylidene acetal, methylene acetal, ethylidene acetal, p-methoxybenzylidene acetal, tert-butylmethylidene acetal, 3-(benzyloxy)propylidene acetal, acrolein acetal, 2-nitrobenzylidene acetal, mesitylene acetal or 2-naphthaldehyde acetal, are examples of dihydroxyl protective groups.

The term "haloalkyl" is intended to indicate an alkyl group as defined herein substituted with one or more halogen atoms as defined herein, e.g. fluoro or chloro, such as difluoromethyl, trifluoromethyl, trifluoroethyl, difluoroethyl, fluoroethyl or fluoromethyl.

The terms "haloalkyloxy" and "haloalkoxy" are intended to indicate a haloalkyl group as defined herein which is appended to the parent molecular moiety through an oxygen atom, such as difluoromethoxy, trifluoromethoxy or fluoromethoxy.

The term "halogen" is intended to indicate a substituent from the 7$^{th}$ main group of the periodic table, such as fluoro, chloro and bromo.

The term "heteroaryl" is intended to indicate radicals of monocyclic heteroaromatic rings comprising 5- or 6-membered ring which contains from 1-5 carbon atoms and from 1-4 heteroatoms selected from oxygen, sulphur and nitrogen; and fused polycyclic heteroaromatic radicals which contains from 1-10 carbon atoms and 1-6 heteroatoms, selected from oxygen, sulphur and nitrogen, such as 1-5 heteroatoms and 1-6 carbon atoms, such as 1-5 heteroatoms and 1-4 carbon atoms, such as 1-4 heteroatoms and 1-5 carbon atoms. Said fused polycyclic heteroaromatic radicals comprise a monocyclic heteroaromatic ring fused to a cycloalkyl, a monocyclic heteroaromatic ring fused to an aryl, particularly a five-membered monocyclic heteroaromatic ring fused to a six-membered aromatic ring and a six-membered monocyclic heteroaromatic ring fused to a six-membered aromatic ring, a monocyclic heteroaromatic ring fused to a cycloalkenyl, a monocyclic heteroaromatic ring fused to a heterocycloalkyl, a monocyclic heteroaromatic ring fused to a heterocycloalkenyl and a monocyclic heteroaromatic ring fused to another heteroaromatic ring, particularly a five-membered monocyclic heteroaromatic ring fused to a six-membered heteroaromatic ring, a five-membered monocyclic heteroaromatic ring fused to a five-membered heteroaromatic ring, and a six-membered monocyclic heteroaromatic ring fused to a six-membered heteroaromatic ring as defined herein. The heteroaryl radical may be connected to the parent molecular moiety through a carbon atom or a nitrogen atom contained anywhere within the heteroaryl group. Representative examples of heteroaryl groups include, but are not limited to, azaindolyl, benzofuranyl, benzimidazolyl, benzooxazolyl, 1,2-benzoxazolyl, 1,3-benzoxazolyl, benzothiazolyl, benzothienyl, cinnolyl, furanyl, imidazolyl, imidazopyridinyl, imidazopyrimidinyl, imidazothiazolyl, indazolyl, indolyl, isobenzofuranyl, isoquinolyl, isothiazolyl, isoxazolyl, oxadiazolyl, oxazolyl, pyrazinyl, pyrazolyl, pyridazinyl, pyridyl, pyrimidinyl, pyrrolopyrimidinyl, pyrrolyl, quinolyl, tetrazolyl, thiadiazolyl, thiazolyl, thienopyridinyl, thienyl, triazinyl, triazolyl, furopyridinyl or isoquinolinyl.

The term "heterocycloalkyl" is intended to indicate a cycloalkane radical as described herein, wherein one or more carbon atoms are replaced by heteroatoms, comprising 1-10 carbon atoms, e.g. 2-5 or 2-4 carbon atoms, further comprising 1-6 heteroatoms, preferably 1, 2, or 3 heteroatoms, selected from O, N, or S. The term "heterocycloalkyl" furthermore refers to a cycloalkane radical optionally fused with carbocyclic rings, including aryl, the cycloalkane radical comprising 1-5 heteroatoms, selected from O, N, or S. The heterocycloalkyl radical may be connected to the parent molecular moiety through a carbon atom or a nitrogen atom contained anywhere within the heterocycloalkyl group. Representative examples of heterocycloalkyl groups include, but are not limited to azepanyl, azetidinyl, aziridinyl, benzoxazinyl, dihydroquinolinyl, dihydroquinoxalinyl, dioxolanyl, dioxolyl, imidazolidinyl, indolinyl, isoindolinyl, morpholinyl, oxetanyl, piperazinyl, piperidinyl, pyrrolidinyl, quinoxalinyl, tetrahydrofuranyl, tetrahydropyranyl, tetrahydrothiophenyl, tetrahydrothiopyranyl, thietanyl.

The terms "heterocyclyl" and "heterocyclic ring" are intended to include the definitions heteroaryl, heterocycloalkyl and heterocylcoalkenyl as defined herein, comprising 1-6 heteroatoms selected from oxygen, nitrogen and sulphur, including said ring systems fused with each other or with cycloalkyl, cycloalkenyl or aryl groups, as defined herein.

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-10 carbon atoms, and preferably comprises 1-8, e.g. 1-6, e.g. 1-4, e.g. 1-3, e.g. 1-2 carbon atoms. The term includes alkyl, alkenyl, cycloalkyl, cycloalkenyl, alkynyl and aryl, as indicated herein.

In some instances, the number of carbon atoms in a hydrocarbon radical (e.g. alkyl, alkenyl, cycloalkyl, cycloalkenyl, alkynyl and aryl, as indicated below) is indicated by the prefix "$(C_a-C_b)$", wherein a is the minimum number and b is the maximum number of carbons in the hydrocarbon radical.

Thus, for example $(C_1-C_4)$alkyl is intended to indicate an alkyl radical comprising from 1 to 4 carbon atoms, and $(C_3-C_5)$cycloalkyl is intended to indicate a cycloalkyl radical comprising from 3 to 5 carbon atoms.

The term "hydroxyalkyl" is intended to indicate an alkyl group as defined above substituted with one or more hydroxy, e.g. hydroxymethyl, hydroxyethyl, hydroxypropyl.

The term "oxo" is intended to indicate an oxygen atom which is connected to the parent molecular moiety via a double bond (=O).

The term "hydroxyl protecting agent" is intended to mean a reagent which under suitable reaction conditions reacts with a hydroxyl group to form a hydroxyl protective group.

The term "protective group" or "protecting group" is intended to indicate a group which is introduced into a molecule by chemical modification of a functional group in order to obtain chemoselectivity in a subsequent chemical reaction.

When two or more of the above defined terms are used in combination, such as arylalkyl, heteroarylalkyl, cycloalkylalkyl and the like, it is to be understood that the first mentioned radical is a substituent on the latter mentioned radical, where the point of attachment to the parent molecular moiety is on the latter radical.

The group C(O) is intended to represent a carbonyl group (C=O)

The term "pharmaceutically acceptable salt" is intended to indicate salts prepared by reacting a compound of formula I, which comprise a basic moiety, with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I comprising an acidic moiety may also be prepared by reaction with a suitable base such as sodium hydroxide, potassium hydroxide, magnesium hydroxide, calcium hydroxide, silver hydroxide, ammonia or the like, or suitable non-toxic amines, such as lower alkylamines, hydroxy-lower alkylamines, cycloalkylamines, or benzylamines, or L-arginine or L-lysine. Further examples of pharmaceutical acceptable salts are listed in Berge, S. M.; J. Pharm. Sci.; (1977), 66(1), 1-19, which is incorporated herein by reference.

The term "solvate" is intended to indicate a species formed by interaction between a compound, e.g. a compound of formula I, and a solvent, e.g. alcohol, glycerol or water, wherein said species are in a crystalline form. When water is the solvent, said species is referred to as a hydrate.

The term "substituted" as applied to any moiety herein is intended to indicate substitution with compatible substituents.

The terms "physiological disorders or diseases associated with hyperplasia, neoplasia or dysplasia" in the context of the present invention is intended to cover disorders or diseases such as cutaneous warts, including common warts (*Verruca vulgaris*), plantar warts (*Verruca plantaris*) and flat warts (*verruca plana*); Genital warts (*condyloma acuminatum*), Pyogenic granuloma, Haemangioma, Scleroderma; Cancers and precancerous lesions such as Actinic keratosis, Squamous cell carcinoma including squamous cell carcinoma in situ (Bowen's disease), invasive squamous cell carcinoma, cutaneous squamous cell carcinoma, mucosal squamous cell carcinoma, head and neck squamous cell carcinoma; Basal cell carcinoma including Superficial basal cell carcinoma and Nodular basal cell carcinoma; Bladder cancer, Lentigo maligna, Cervical dysplasia, Vulva dysplasia and anal dysplasia, Primary melanoma in situ, Head and neck cancer, Cutaneous metastases of any cancer, Kaposi's sarcoma, Keratoacanthoma, Merkel cell tumor, Prostate cancer, Mycosis fungoides, Intraepithelial neoplasias including anal, cervical, ductal, oral, perianal, prostatic, penile, vaginal and vulvar intraepithelial neoplasia.

The term "cosmetic indications" in the context of the present invention is intended to cover indications such as: Photodamaged skin, Seborrheic keratosis, Scars, Keloids, Melasma, Poikiloderma of Civatte, Tattoo removal, Naevi and Skin tags.

The term "photodamaged skin" in the context of the present invention is intended to cover fine lines, wrinkles and UV-ageing. UV ageing is often manifested by an increase in the epidermal thickness or epidermal atrophy and most notably by solar elastosis, the accumulation of elastin containing material just below the dermal-epidermal junction. Collagen and elastic fibres become fragmented and disorganised. At a cosmetic level this can be observed as a reddening and/or thickening of the skin resulting a leathery appearance, skin fragility and irregular pigmentation, loss of tone and elasticity, as well as wrinkling, dryness, sunspots and deep furrow formation.

The term "treatment" as used herein means the management and care of a patient for the purpose of combating a disease, disorder or condition. The term is intended to include the delaying of the progression of the disease, disorder or condition, the alleviation, amelioration or relief of symptoms and complications, and/or the cure or elimination of the disease, disorder or condition. The term may also include prevention of the condition, wherein prevention is to be understood as the management and care of a patient for the purpose of combating the disease, condition or disorder and includes the administration of the active compounds to prevent the onset of the symptoms or complications. Nonetheless, prophylactic (preventive) and therapeutic (curative) treatments are two separate aspects.

All references, including publications, patent applications and patents, cited herein are hereby incorporated by reference in their entirety and to the same extent as if each reference were individually and specifically indicated to be incorporated by reference, regardless of any separately provided incorporation of particular documents made elsewhere herein.

EMBODIMENTS OF THE INVENTION

In one or more embodiments of the present invention $R_1$ represents heteroaryl; said heteroaryl optionally being substituted with one or more substituents independently selected from $R_2$; and wherein said heteroaryl is selected from the group consisting of

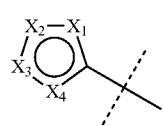
G1

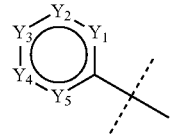
G2

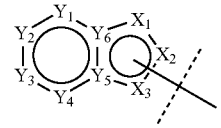
G3

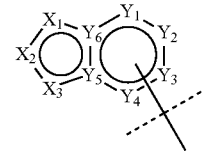
G4

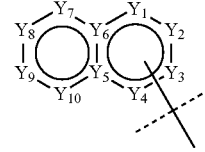
G5 wherein $X_1$, $X_2$, $X_3$ and $X_4$ are each independently selected from the group consisting of C, CH, N, NH, S and O;

and wherein $Y_1, Y_2, Y_3, Y_4, Y_5, Y_6, Y_7, Y_8, Y_9$ and $Y_{10}$ are each independently selected from the group consisting of C, CH and N;

In one or more embodiments of the present invention $R_1$ represents heteroaryl; said heteroaryl optionally being substituted with one or more substituents independently selected from $R_2$; and wherein said heteroaryl is selected from the group consisting of

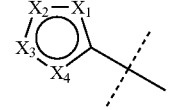
G1

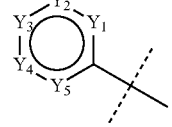
G2

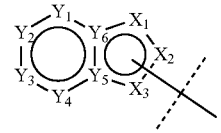
G3

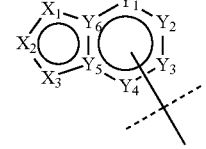
G4

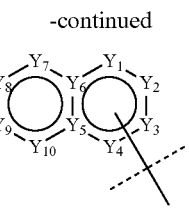

wherein $X_1$, $X_2$, $X_3$ and $X_4$ are each independently selected from the group consisting of C, CH, N, NH, S and O;
and wherein $Y_1$, $Y_2$, $Y_3$, $Y_4$, $Y_5$, $Y_6$, $Y_7$, $Y_8$, $Y_9$ and $Y_{10}$ are each independently selected from the group consisting of C, CH and N;
with the proviso for G1 that at least one of $X_1$, $X_2$, $X_3$ or $X_4$ is selected from N, NH, S and O;
with the proviso for G2 that at least one of $Y_1$, $Y_2$, $Y_3$, $Y_4$ or $Y_5$ represents N;
with the proviso for G3 that at least one of $X_1$, $X_2$ or $X_3$ is selected from N, NH, S and O;
with the proviso for G4 that at least one of $Y_1$, $Y_2$, $Y_3$ or $Y_4$ represents N;
with the proviso for G5 that at least one of $Y_1$, $Y_2$, $Y_3$ or $Y_4$ represents N;
with the proviso for G3, G4 and G5 that the point of attachment to 3-O-ingenol is through a carbon atom;

In one or more embodiments of the present invention $R_1$ represents $G_1$, wherein at least one of $X_1$ or $X_4$ is selected from the group consisting of N, NH, S and O;
or
$R_1$ represents $G_2$, wherein at least one of $Y_1$ or $Y_5$ represents N;
or
$R_1$ represents $G_3$, wherein the point of attachment to 3-O-ingenol occurs through $X_1$ or $X_3$ and wherein $X_2$ is selected from the group consisting of N, NH, S and O;
or
$R_1$ represents $G_3$, wherein the point of attachment to 3-O-ingenol occurs through $X_2$ and wherein at least one of $X_1$ and $X_3$ is selected from the group consisting of N, NH, S and O;
or
$R_1$ represents $G_4$, wherein the point of attachment to 3-O-ingenol occurs through $Y_1$ and wherein $Y_2$ represents N;
or
$R_1$ represents $G_4$, wherein the point of attachment to 3-O-ingenol occurs through $Y_2$ and wherein at least one of $Y_1$ and $Y_3$ represents N;
or
$R_1$ represents $G_5$, wherein the point of attachment to 3-O-ingenol occurs through $Y_1$ and wherein $Y_2$ represents N;
or
$R_1$ represents $G_5$, wherein the point of attachment to 3-O-ingenol occurs through $Y_2$ and wherein at least one of $Y_1$ and $Y_3$ represents N.

In one or more embodiments of the present invention $R_1$ represents $G_1$, wherein one $X_1$ or $X_4$ is selected from the group consisting of N, NH, S and O and wherein the other $X_1$ or $X_4$ is substituted with $R_2$;
or
$R_1$ represents $G_2$, wherein one $Y_1$ or $Y_5$ represents N, and wherein the other $Y_1$ or $Y_5$ is substituted with $R_2$;
or
$R_1$ represents $G_3$, wherein the point of attachment to 3-O-ingenol occurs through $X_1$ or $X_3$ and wherein $X_2$ is selected from the group consisting of N, NH, S and O;
or
$R_1$ represents $G_4$, wherein the point of attachment to 3-O-ingenol occurs through $Y_1$ and wherein $Y_2$ represents N;
or
$R_1$ represents $G_5$, wherein the point of attachment to 3-O-ingenol occurs through $Y_1$ and wherein $Y_2$ represents N.

In one or more embodiments of the present invention $R_1$ represents oxazolyl, isoxazolyl, thiazolyl, isothiazolyl, imidazolyl, pyrazolyl, pyridyl, pyrimidinyl, pyrazinyl, pyridazinyl, triazinyl, isoquinolinyl, 1,2-benzoxazolyl, 1,3-benzoxazolyl, indazolyl, thieno[2,3-c]pyridine or furo[3,2-c]pyridine.

In one or more embodiments of the present invention $R_1$ represents oxazolyl, isoxazolyl, thiazolyl, isothiazolyl, imidazolyl, pyrazolyl, pyridyl, pyrimidinyl, pyrazinyl, pyridazinyl, triazinyl, isoquinolinyl, benzoxazolyl, indazolyl, thienopyridyl, furopyridyl or oxadiazolyl.

In one or more embodiments of the present invention $R_2$ represents halogen, cyano, $(C_1-C_4)$alkyl, halo$(C_1-C_4)$alkyl, $(C_2-C_6)$alkenyl, $(C_1-C_6)$alkoxy or $(C_3-C_6)$cycloalkyl.

In one or more embodiments of the present invention $R_2$ represents methyl, trifluoromethyl, trifluoroethyl, propenyl, bromo, chloro, fluoro, cyano, methoxy, isopropyl, cyclopentyl, difluoroethyl or fluoroethyl.

In one or more embodiments of the present invention $R_1$ represents imidazolyl, pyridyl, pyrimidinyl, isoquinolinyl, benzoxazolyl, indazolyl, thienopyridinyl, furopyridinyl or oxadiazolyl.

In one or more embodiments of the present invention $R_2$ represents halogen, cyano, $(C_1-C_4)$alkyl, halo$(C_1-C_4)$alkyl, $(C_2-C_6)$alkenyl or $(C_1-C_6)$alkoxy.

In one or more embodiments of the present invention $R_2$ represents methyl, trifluoromethyl, trifluoroethyl, propenyl, bromo, chloro, fluoro, cyano or methoxy.

In an embodiment the present invention provides a compound according to formula I, said compound being selected from the group consisting of
3-O-(6-Chloro-5-methyl-pyrimidin-4-yl)-ingenol,
3-O-(1,2-Benzoxazol-3-yl)-ingenol,
3-O-(5-(Trifluoromethyl)-2-pyridyl)-ingenol,
3-O-(5-Allyl-6-chloro-pyrimidin-4-yl)-ingenol,
3-O-(3-Formyl-2-pyridyl)-ingenol,
3-O-(2-Pyridyl)-ingenol,
3-O-(1-Methylindazol-3-yl)-ingenol,
3-O-(1-Methylimidazol-2-yl)-ingenol,
3-O-(1-Allylimidazol-2-yl)-ingenol,
3-O-(5-(Trifluoromethyl)-pyrimidin-2-yl)-ingenol,
3-O-(4-Bromo-2-pyridyl)-ingenol,
3-O-(3-Fluoro-2-pyridyl)-ingenol,
3-O-(4-(Trifluoromethyl)-2-pyridyl)-ingenol,
3-O-(4-(Trifluoromethyl)-pyrimidin-2-yl)-ingenol,
3-O-(3-Chloro-2-pyridyl)-ingenol,
3-O-(3-Cyano-2-pyridyl)-ingenol,
3-O-(6-(Trifluoromethyl)-2-pyridyl)-ingenol,
3-O-(3-(Trifluoromethyl)-2-pyridyl)-ingenol,
3-O-(1-Isoquinolyl)-ingenol,
3-O-(1-Cyclopentylimidazol-2-yl)-ingenol,
3-O-(1-(2,2-Difluoroethyl)imidazol-2-yl)-ingenol,
3-O-(1-(2-Fluoroethyl)imidazol-2-yl)-ingenol,
3-O-(Thieno[2,3-c]pyridine-7-yl)-ingenol,
3-O-(3-Methyl-2-pyridyl)-ingenol,
3-O-(6-Chloro-1,2-benzoxazol-3-yl)-ingenol,
3-O-(Furo[3,2-c]pyridine-4-yl)-ingenol,
3-O-(Thieno[3,2-c]pyridine-4-yl)-ingenol,
3-O-(4-Fluoro-1,2-benzoxazol-3-yl)-ingenol,
3-O-(3-Methoxy-pyridin-2-yl)-ingenol,
3-O-(5-Methoxy-1,2-benzoxazol-3-yl)-ingenol,
3-O-(5-Chloro-1,2-benzoxazol-3-yl)-ingenol, 3-O-(6-Methoxy-1,2-benzoxazol-3-yl)-ingenol,
3-O-(5-Isopropyl-1,2,4-oxadiazol-3-yl)-ingenol
and pharmaceutically acceptable salts, hydrates, solvates or pharmaceutically acceptable and physiologically cleavable esters thereof.

In an embodiment the present invention provides a compound according to formula I, said compound being selected from the group consisting of
3-O-(6-Chloro-5-methyl-pyrimidin-4-yl)-ingenol,
3-O-(1,2-Benzoxazol-3-yl)-ingenol,
3-O-(5-(Trifluoromethyl)-2-pyridyl)-ingenol,
3-O-(5-Allyl-6-chloro-pyrimidin-4-yl)-ingenol,
3-O-(3-Formyl-2-pyridyl)-ingenol,
3-O-(2-Pyridyl)-ingenol,
3-O-(1-Methylindazol-3-yl)-ingenol,
3-O-(1-Methylimidazol-2-yl)-ingenol,
3-O-(1-Allylimidazol-2-yl)-ingenol,
3-O-(5-(Trifluoromethyl)-pyrimidin-2-yl)-ingenol,
3-O-(4-Bromo-2-pyridyl)-ingenol,
3-O-(3-Fluoro-2-pyridyl)-ingenol,
3-O-(4-(Trifluoromethyl)-2-pyridyl)-ingenol,
3-O-(4-(Trifluoromethyl)-pyrimidin-2-yl)-ingenol,
3-O-(3-Chloro-2-pyridyl)-ingenol,
3-O-(3-Cyano-2-pyridyl)-ingenol,
3-O-(6-(Trifluoromethyl)-2-pyridyl)-ingenol,
3-O-(3-(Trifluoromethyl)-2-pyridyl)-ingenol,
3-O-(1-Isoquinolyl)-ingenol,
3-O-(1-Cyclopentylimidazol-2-yl)-ingenol,
3-O-(1-(2,2-Difluoroethyl)imidazol-2-yl)-ingenol,
3-O-(1-(2-Fluoroethyl)imidazol-2-yl)-ingenol,
3-O-(Thieno[2,3-c]pyridine-7-yl)-ingenol,
3-O-(3-Methyl-2-pyridyl)-ingenol,
3-O-(6-Chloro-1,2-benzoxazol-3-yl)-ingenol,
3-O-(Furo[3,2-c]pyridine-4-yl)-ingenol,
3-O-(Thieno[3,2-c]pyridine-4-yl)-ingenol
and pharmaceutically acceptable salts, hydrates, solvates or pharmaceutically acceptable and physiologically cleavable esters thereof.

In an embodiment the present invention provides a compound according to formula I, said compound being selected from the group consisting of
3-O-(4-Fluoro-1,2-benzoxazol-3-yl)-ingenol,
3-O-(3-Methoxy-pyridin-2-yl)-ingenol,
3-O-(5-Methoxy-1,2-benzoxazol-3-yl)-ingenol,
3-O-(5-Chloro-1,2-benzoxazol-3-yl)-ingenol,
3-O-(6-Methoxy-1,2-benzoxazol-3-yl)-ingenol,
and pharmaceutically acceptable salts, hydrates, solvates or pharmaceutically acceptable and physiologically cleavable esters thereof.

In an embodiment the present invention provides a compound according to formula I, said compound being selected from the group consisting of
3-O-(6-Chloro-5-methyl-pyrimidin-4-yl)-ingenol,
3-O-(1,2-Benzoxazol-3-yl)-ingenol,
3-O-(5-(Trifluoromethyl)-2-pyridyl)-ingenol,
3-O-(5-Allyl-6-chloro-pyrimidin-4-yl)-ingenol,
3-O-(3-Formyl-2-pyridyl)-ingenol,
3-O-(2-Pyridyl)-ingenol,
3-O-(1-Methylindazol-3-yl)-ingenol,
3-O-(1-Methylimidazol-2-yl)-ingenol,
3-O-(1-Allylimidazol-2-yl)-ingenol,
3-O-(5-(Trifluoromethyl)-pyrimidin-2-yl)-ingenol,
3-O-(4-Bromo-2-pyridyl)-ingenol,
3-O-(3-Fluoro-2-pyridyl)-ingenol,
3-O-(4-(Trifluoromethyl)-2-pyridyl)-ingenol,
3-O-(4-(Trifluoromethyl)-pyrimidin-2-yl)-ingenol,
3-O-(3-Chloro-2-pyridyl)-ingenol,
3-O-(3-Cyano-2-pyridyl)-ingenol,
3-O-(6-(Trifluoromethyl)-2-pyridyl)-ingenol,
3-O-(3-(Trifluoromethyl)-2-pyridyl)-ingenol,
3-O-(1-Isoquinolyl)-ingenol,
3-O-(1-Cyclopentylimidazol-2-yl)-ingenol,
3-O-(1-(2,2-Difluoroethyl)imidazol-2-yl)-ingenol,
3-O-(1-(2-Fluoroethyl)imidazol-2-yl)-ingenol,
3-O-(Thieno[2,3-c]pyridine-7-yl)-ingenol,
3-O-(3-Methyl-2-pyridyl)-ingenol,
3-O-(6-Chloro-1,2-benzoxazol-3-yl)-ingenol,
3-O-(Furo[3,2-c]pyridine-4-yl)-ingenol,
3-O-(Thieno[3,2-c]pyridine-4-yl)-ingenol,
3-O-(4-Fluoro-1,2-benzoxazol-3-yl)-ingenol,
3-O-(3-Methoxy-pyridin-2-yl)-ingenol,
3-O-(5-Methoxy-1,2-benzoxazol-3-yl)-ingenol,
3-O-(5-Chloro-1,2-benzoxazol-3-yl)-ingenol,
3-O-(6-Methoxy-1,2-benzoxazol-3-yl)-ingenol,
and pharmaceutically acceptable salts, hydrates, solvates or pharmaceutically acceptable and physiologically cleavable esters thereof.

In an embodiment the present invention provides a compound according to formula I, said compound being 3-O-(6-Chloro-5-methyl-pyrimidin-4-yl)-ingenol.

In an embodiment the present invention provides a compound according to formula I, said compound being 3-O-(1,2-Benzoxazol-3-yl)-ingenol.

In an embodiment the present invention provides a compound according to formula I, said compound being 3-O-(5-Allyl-6-chloro-pyrimidin-4-yl)-ingenol.

In an embodiment the present invention provides a compound according to formula I, said compound being 3-O-(3-(Trifluoromethyl)-2-pyridyl)-ingenol.

In an embodiment the present invention provides a compound according to formula I, said compound being 3-O-(1-Isoquinolyl)-ingenol.

In an embodiment the present invention provides a compound according to formula I, said compound being 3-O-(1-Cyclopentylimidazol-2-yl)-ingenol.

In an embodiment the present invention provides a compound according to formula I, said compound being 3-O-(Thieno[2,3-c]pyridine-7-yl)-ingenol.

In an embodiment the present invention provides a compound according to formula I, said compound being 3-O-(6-Chloro-1,2-benzoxazol-3-yl)-ingenol.

In an embodiment the present invention provides a compound according to formula I, said compound being 3-O-(4-Fluoro-1,2-benzoxazol-3-yl)-ingenol and pharmaceutically acceptable salts, hydrates, solvates or pharmaceutically acceptable and physiologically cleavable esters thereof.

In an embodiment the present invention provides a compound according to formula I, said compound being 3-O-(5-Methoxy-1,2-benzoxazol-3-yl)-ingenol and pharmaceutically acceptable salts, hydrates, solvates or pharmaceutically acceptable and physiologically cleavable esters thereof and pharmaceutically acceptable salts, hydrates, solvates or pharmaceutically acceptable and physiologically cleavable esters thereof.

In an embodiment the present invention provides a compound according to formula I, said compound being 3-O-(5-Chloro-1,2-benzoxazol-3-yl)-ingenol and pharmaceutically acceptable salts, hydrates, solvates or pharmaceutically acceptable and physiologically cleavable esters thereof.

In an embodiment the present invention provides a compound according to formula I, said compound being 3-O-(6-Methoxy-1,2-benzoxazol-3-yl)-ingenol and pharmaceutically acceptable salts, hydrates, solvates or pharmaceutically acceptable and physiologically cleavable esters thereof.

In an embodiment the present invention provides a compound according to formula I, said compound being 3-O-(6-Chloro-5-methyl-pyrimidin-4-yl)-ingenol and pharmaceutically acceptable salts, hydrates, solvates or pharmaceutically acceptable and physiologically cleavable esters thereof.

In an embodiment the present invention provides a compound according to formula I, said compound being 3-O-(1,2-Benzoxazol-3-yl)-ingenol and pharmaceutically acceptable salts, hydrates, solvates or pharmaceutically acceptable and physiologically cleavable esters thereof.

In an embodiment the present invention provides a compound according to formula I, said compound being 3-O-(5-Allyl-6-chloro-pyrimidin-4-yl)-ingenol and pharmaceutically acceptable salts, hydrates, solvates or pharmaceutically acceptable and physiologically cleavable esters thereof.

In an embodiment the present invention provides a compound according to formula I, said compound being 3-O-(3-(Trifluoromethyl)-2-pyridyl)-ingenol and pharmaceutically acceptable salts, hydrates, solvates or pharmaceutically acceptable and physiologically cleavable esters thereof.

In an embodiment the present invention provides a compound according to formula I, said compound being 3-O-(1-Isoquinolyl)-ingenol and pharmaceutically acceptable salts, hydrates, solvates or pharmaceutically acceptable and physiologically cleavable esters thereof and pharmaceutically acceptable salts, hydrates, solvates or pharmaceutically acceptable and physiologically cleavable esters thereof.

In an embodiment the present invention provides a compound according to formula I, said compound being 3-O-(1-Cyclopentylimidazol-2-yl)-ingenol and pharmaceutically acceptable salts, hydrates, solvates or pharmaceutically acceptable and physiologically cleavable esters thereof.

In an embodiment the present invention provides a compound according to formula I, said compound being 3-O-(Thieno[2,3-c]pyridine-7-yl)-ingenol and pharmaceutically acceptable salts, hydrates, solvates or pharmaceutically acceptable and physiologically cleavable esters thereof.

In an embodiment the present invention provides a compound according to formula I, said compound being 3-O-(6-Chloro-1,2-benzoxazol-3-yl)-ingenol and pharmaceutically acceptable salts, hydrates, solvates or pharmaceutically acceptable and physiologically cleavable esters thereof.

In an embodiment the present invention provides a compound according to formula I, said compound being 3-O-(4-Fluoro-1,2-benzoxazol-3-yl)-ingenol and pharmaceutically acceptable salts, hydrates, solvates or pharmaceutically acceptable and physiologically cleavable esters thereof.

In an embodiment the present invention provides a compound according to formula I, said compound being 3-O-(5-Methoxy-1,2-benzoxazol-3-yl)-ingenol and pharmaceutically acceptable salts, hydrates, solvates or pharmaceutically acceptable and physiologically cleavable esters thereof.

In an embodiment the present invention provides a compound according to formula I, said compound being 3-O-(5-Chloro-1,2-benzoxazol-3-yl)-ingenol and pharmaceutically acceptable salts, hydrates, solvates or pharmaceutically acceptable and physiologically cleavable esters thereof.

In an embodiment the present invention provides a compound according to formula I, said compound being 3-O-(6-Methoxy-1,2-benzoxazol-3-yl)-ingenol and pharmaceutically acceptable salts, hydrates, solvates or pharmaceutically acceptable and physiologically cleavable esters thereof.

In an embodiment the present invention provides a compound according to formula I, said compound being selected from the group consisting of
3-O-(2-furyl)-ingenol,
3-O-(3-methyl-2-furyl)-ingenol,
3-O-(3-ethyl-2-furyl)-ingenol,
3-O-(4-methyl-2-furyl)-ingenol,
3-O-(4-ethyl-2-furyl)-ingenol,
3-O-(isobenzofuran-1-yl)-ingenol
3-O-(2-thienyl)-ingenol,
3-O-(3-methyl-2-thienyl)-ingenol,
3-O-(3-ethyl-2-thienyl)-ingenol,
3-O-(4-methyl-2-thienyl)-ingenol,
3-O-(4-ethyl-2-thienyl)-ingenol,
3-O-(2-benzothiophen-1-yl)-ingenol,
3-O-(1H-pyrrol-2-yl)-ingenol,
3-O-(isoxazol-3-yl)-ingenol,
3-O-(oxazol-4-yl)-ingenol,
3-O-(oxazol-2-yl)-ingenol,
3-O-(isothiazol-3-yl)-ingenol,
3-O-(1,2-benzothiazol-3-yl)-ingenol,
3-O-(thiazol-4-yl)-ingenol,
3-O-(thiazol-2-yl)-ingenol,
3-O-(1H-pyrazol-3-yl)-ingenol,
3-O-(1H-imidazol-4-yl)-ingenol,
3-O-(1H-imidazol-2-yl)-ingenol,
3-O-(isoxazol-5-yl)-ingenol,
3-O-(2,1-benzoxazol-3-yl)-ingenol,
3-O-(oxazol-5-yl)-ingenol,
3-O-(isothiazol-5-yl)-ingenol,
3-O-(thiazol-5-yl)-ingenol,
3-O-(1,2,5-oxadiazol-3-yl)-ingenol,
3-O-(1,2,4-oxadiazol-3-yl)-ingenol, Compounds useful as intermediates for the synthesis of compounds according to formula I, may in particular be selected amongst the list consisting of
3-O-(6-Chloro-5-methyl-pyrimidin-4-yl)-ingenol-5,20-acetonide,
3-O-(1,2-Benzoxazol-3-yl)-ingenol-5,20-acetonide,
3-O-(5-(Trifluoromethyl)-2-pyridyl)-ingenol-5,20-acetonide,
3-O-(5-Allyl-6-chloro-pyrimidin-4-yl)-ingenol-5,20-acetonide,
3-O-(3-Formyl-2-pyridyl)-ingenol-5,20-acetonide,
3-O-(2-Pyridyl)-ingenol-5,20-acetonide,
3-O-(1-Methylindazol-3-yl)-ingenol-5,20-acetonide,
3-O-(1-Methylimidazol-2-yl)-ingenol-5,20-acetonide,
3-O-(1-Allylimidazol-2-yl)-ingenol-5,20-acetonide,
3-O-(5-(Trifluoromethyl)-pyrimidin-2-yl)-ingenol-5,20-acetonide,
3-O-(4-Bromo-2-pyridyl)-ingenol-5,20-acetonide,
3-O-(3-Fluoro-2-pyridyl)-ingenol-5,20-acetonide,
3-O-(4-(Trifluoromethyl)-2-pyridyl)-ingenol-5,20-acetonide,
3-O-(4-(Trifluoromethyl)-pyrimidin-2-yl)-ingenol-5,20-acetonide,
3-O-(3-Chloro-2-pyridyl)-ingenol-5,20-acetonide,
3-O-(3-Cyano-2-pyridyl)-ingenol-5,20-acetonide,
3-O-(6-(Trifluoromethyl)-2-pyridyl)-ingenol-5,20-acetonide,
3-O-(3-(Trifluoromethyl)-2-pyridyl)-ingenol-5,20-acetonide,
3-O-(1-Isoquinolyl)-ingenol-5,20-acetonide,
3-O-(1-Cyclopentylimidazol-2-yl)-ingenol-5,20-acetonide,
3-O-(1-(2,2-Difluoroethyl)imidazol-2-yl)-ingenol-5,20-acetonide,
3-O-(1-(2-Fluoroethyl)imidazol-2-yl)-ingenol-5,20-acetonide,
3-O-(Thieno[2,3-c]pyridine-7-yl)-ingenol-5,20-acetonide,
3-O-(3-Methyl-2-pyridyl)-ingenol-5,20-acetonide,
3-O-(6-Chloro-1,2-benzoxazol-3-yl)-ingenol-5,20-acetonide, 3-O-(Furo[3,2-c]pyridine-4-yl)-ingenol-5,20-acetonide,
3-O-(Thieno[3,2-c]pyridine-4-yl)-ingenol-5,20-acetonide, Compounds useful as intermediates for the synthesis of compounds according to formula I, may in particular be selected amongst the list consisting of
3-O-(6-Chloro-5-methyl-pyrimidin-4-yl)-ingenol-5,20-acetonide,
3-O-(1,2-Benzoxazol-3-yl)-ingenol-5,20-acetonide,
3-O-(5-(Trifluoromethyl)-2-pyridyl)-ingenol-5,20-acetonide,
3-O-(5-Allyl-6-chloro-pyrimidin-4-yl)-ingenol-5,20-acetonide,
3-O-(3-Formyl-2-pyridyl)-ingenol-5,20-acetonide,
3-O-(2-Pyridyl)-ingenol-5,20-acetonide,
3-O-(1-Methylindazol-3-yl)-ingenol-5,20-acetonide,
3-O-(1-Methylimidazol-2-yl)-ingenol-5,20-acetonide,
3-O-(1-Allylimidazol-2-yl)-ingenol-5,20-acetonide,
3-O-(5-(Trifluoromethyl)-pyrimidin-2-yl)-ingenol-5,20-acetonide,
3-O-(4-Bromo-2-pyridyl)-ingenol-5,20-acetonide,
3-O-(3-Fluoro-2-pyridyl)-ingenol-5,20-acetonide,
3-O-(4-(Trifluoromethyl)-2-pyridyl)-ingenol-5,20-acetonide,
3-O-(4-(Trifluoromethyl)-pyrimidin-2-yl)-ingenol-5,20-acetonide,
3-O-(3-Chloro-2-pyridyl)-ingenol-5,20-acetonide,
3-O-(3-Cyano-2-pyridyl)-ingenol-5,20-acetonide,
3-O-(6-(Trifluoromethyl)-2-pyridyl)-ingenol-5,20-acetonide,
3-O-(3-(Trifluoromethyl)-2-pyridyl)-ingenol-5,20-acetonide,
3-O-(1-Isoquinolyl)-ingenol-5,20-acetonide,
3-O-(1-Cyclopentylimidazol-2-yl)-ingenol-5,20-acetonide,
3-O-(1-(2,2-Difluoroethyl)imidazol-2-yl)-ingenol-5,20-acetonide,
3-O-(1-(2-Fluoroethyl)imidazol-2-yl)-ingenol-5,20-acetonide,
3-O-(Thieno[2,3-c]pyridine-7-yl)-ingenol-5,20-acetonide,
3-O-(3-Methyl-2-pyridyl)-ingenol-5,20-acetonide,
3-O-(6-Chloro-1,2-benzoxazol-3-yl)-ingenol-5,20-acetonide,
3-O-(Furo[3,2-c]pyridine-4-yl)-ingenol-5,20-acetonide,
3-O-(Thieno[3,2-c]pyridine-4-yl)-ingenol-5,20-acetonide,
3-O-(4-Fluoro-1,2-benzoxazol-3-yl)-ingenol-5,20-acetonide,
3-O-(3-Methoxy-pyridin-2-yl)-ingenol-5,20-acetonide,
3-O-(5-Methoxy-1,2-benzoxazol-3-yl)-ingenol-5,20-acetonide,
3-O-(5-Chloro-1,2-benzoxazol-3-yl)-ingenol-5,20-acetonide,
3-O-(6-Methoxy-1,2-benzoxazol-3-yl)-ingenol-5,20-acetonide,
3-O-(5-Isopropyl-1,2,4-oxadiazol-3-yl)-ingenol-5,20-acetonide.

In one or more embodiments of the present invention $R_1$ is selected from the group consisting of G1a, G2a, G3a, G3b, G4a, G4b, G5a and G5b; G1a, G2a, G3a, G3b, G4a, G4b, G5a and G5b optionally being substituted with one or more substituents independently selected from $R_2$;

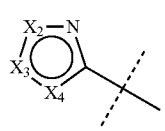
G1a

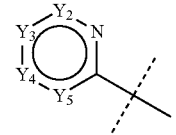
G2a

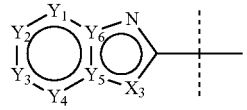
G3a

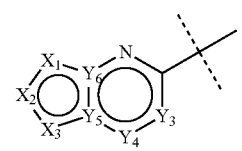
G4a

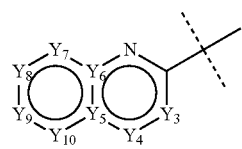
G5a

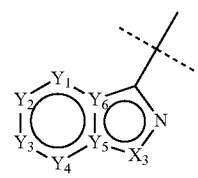
G3b

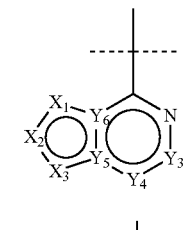
G4b

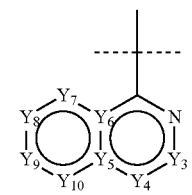
G5b wherein $X_1$, $X_2$, $X_3$ and $X_4$ are each independently selected from the group consisting of C, CH, N, NH, S and O;
and wherein $Y_1$, $Y_2$, $Y_3$, $Y_4$, $Y_5$, $Y_6$, $Y_7$, $Y_8$, $Y_9$ and $Y_{10}$ are each independently selected from the group consisting of C, CH and N;
and wherein $R_2$ represents cyano or halogen;
or $R_2$ represents $(C_1-C_6)$alkyl, $(C_2-C_6)$alkenyl, $(C_1-C_6)$alkoxy, $(C_3-C_6)$cycloalkyl, halo$(C_1-C_6)$alkyloxy, heterocycloalkyl, aryl or heteroaryl; said $(C_1-C_6)$alkyl optionally being substituted with one or more substituents independently selected from the group consisting of halogen, cyano, hydroxyl and oxo;
or $R_2$ represents —$NR_aCOR_b$, —$CONR_aR_b$, —$COOR_a$, —$OCOR_a$, —$OR_a$, —$OCONR_aR_b$, —$NR_aCOOR_b$, —$NR_aSO_2R_b$, —$SO_2NR_aR_b$, —$SO_2R_a$, —$S(O)R_a$ or —$NR_aR_b$;
wherein $R_a$ and $R_b$ are each independently selected from the group consisting of hydrogen, $(C_1-C_4)$alkyl, halo$(C_1-C_4)$ alkyl, hydroxy($C_1$-$C_4$)alkyl, cyano($C_1$-$C_4$)alkyl, aryl, heteroaryl, ($C_3$-$C_6$)cycloalkyl and heterocycloalkyl.

In one or more embodiments of the present invention $R_1$ represents G1, wherein $X_1$, $X_2$, $X_3$ and $X_4$ are each independently selected from the group consisting of C, CH, N, NH, S and O; G1 optionally being substituted with one or more substituents independently selected from $R_2$.

In one or more embodiments of the present invention $R_1$ represents G2, wherein $Y_1$, $Y_2$, $Y_3$, $Y_4$, and $Y_5$ are each independently selected from the group consisting of C, CH and N; G2 optionally being substituted with one or more substituents independently selected from $R_2$.

In one or more embodiments of the present invention $R_1$ represents G3, wherein $X_1$, $X_2$, and $X_3$ are each independently selected from the group consisting of C, CH, N, NH, S and O; and wherein $Y_1$, $Y_2$, $Y_3$, $Y_4$, $Y_5$ and $Y_6$ are each independently selected from the group consisting of C, CH and N; G3 optionally being substituted with one or more substituents independently selected from $R_2$.

In one or more embodiments of the present invention $R_1$ represents G4, wherein $X_1$, $X_2$, and $X_3$ are each independently selected from the group consisting of C, CH, N, NH, S and O; and wherein $Y_1$, $Y_2$, $Y_3$, $Y_4$, $Y_5$ and $Y_6$ are each independently selected from the group consisting of C, CH and N; G4 optionally being substituted with one or more substituents independently selected from $R_2$.

In one or more embodiments of the present invention $R_1$ represents G5, wherein $Y_1$, $Y_2$, $Y_3$, $Y_4$, $Y_5$, $Y_6$, $Y_7$, $Y_8$, $Y_9$ and $Y_{10}$ are each independently selected from the group consisting of C, CH and N; G5 optionally being substituted with one or more substituents independently selected from $R_2$.

In one or more embodiments of the present invention $R_1$ represents G1 or G3, wherein $X_1$, $X_2$, $X_3$ and $X_4$ are each independently selected from the group consisting of C, CH, N, NH, S and O; and wherein $Y_1$, $Y_2$, $Y_3$, $Y_4$, $Y_5$ and $Y_6$ are each independently selected from the group consisting of C, CH and N; G1 and G3 optionally being substituted with one or more substituents independently selected from $R_2$.

In one or more embodiments of the present invention $R_1$ represents G2, G4 or G5, wherein $X_1$, $X_2$, and $X_3$ are each independently selected from the group consisting of C, CH, N, NH, S and O; and wherein $Y_1$, $Y_2$, $Y_3$, $Y_4$, $Y_5$, $Y_6$, $Y_7$, $Y_8$, $Y_9$ and $Y_{10}$ are each independently selected from the group consisting of C, CH and N; G2, G4 and G5 optionally being substituted with one or more substituents independently selected from $R_2$.

In one or more embodiments of the present invention $R_1$ is selected from the group consisting of G1a, G2a, G3a, G3b, G4a, G4b, G5a and G5b; G1a, G2a, G3a, G3b, G4a, G4b, G5a and G5b optionally being substituted with one or more substituents independently selected from $R_2$;

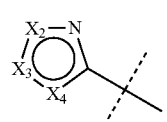
G1a

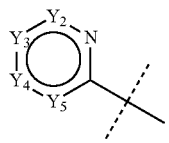
G2a

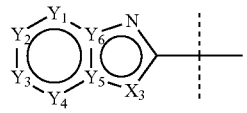
G3a

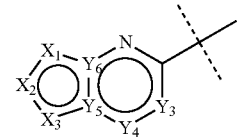
G4a

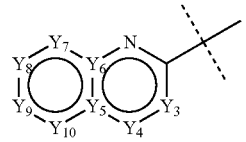
G5a

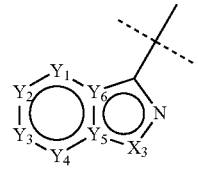
G3b

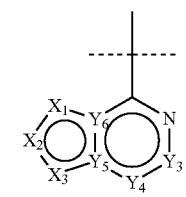
G4b

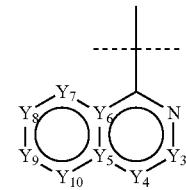
G5b wherein $X_1$, $X_2$, $X_3$ and $X_4$ are each independently selected from the group consisting of C, CH, N, NH, S and O;
and $Y_1$, $Y_2$, $Y_3$, $Y_4$, $Y_5$, $Y_6$, $Y_7$, $Y_8$, $Y_9$ and $Y_{10}$ are each independently selected from the group consisting of C, CH and N;
and wherein $R_2$ represents cyano or halogen; or $R_2$ represents ($C_1$-$C_6$)alkyl, ($C_2$-$C_6$)alkenyl, ($C_1$-$C_6$)alkoxy, ($C_3$-$C_6$)cycloalkyl, halo($C_1$-$C_6$)alkyloxy, heterocycloalkyl, aryl or heteroaryl; said ($C_1$-$C_6$)alkyl optionally being substituted with one or more substituents independently selected from the group consisting of halogen, cyano, hydroxyl and oxo.

In one or more embodiments of the present invention $R_1$ represents G1, wherein $X_1$, $X_2$, $X_3$ and $X_4$ are each independently selected from the group consisting of C, CH, N, NH, S and O; G1 optionally being substituted with one or more substituents independently selected from $R_2$; wherein $R_2$ represents cyano or halogen; or $R_2$ represents ($C_1$-$C_6$)alkyl, ($C_2$-$C_6$)alkenyl, ($C_1$-$C_6$)alkoxy, ($C_3$-$C_6$)cycloalkyl, halo($C_1$-$C_6$)alkyloxy, heterocycloalkyl, aryl or heteroaryl; said ($C_1$-$C_6$)alkyl optionally being substituted with one or more substituents independently selected from the group consisting of halogen, cyano, hydroxyl and oxo.

In one or more embodiments of the present invention $R_1$ represents G2, wherein $Y_1$, $Y_2$, $Y_3$, $Y_4$, and $Y_5$ are each independently selected from the group consisting of C, CH and N; G2 optionally being substituted with one or more substituents independently selected from $R_2$; wherein $R_2$ represents cyano or halogen; or $R_2$ represents $(C_1-C_6)$alkyl, $(C_2-C_6)$alkenyl, $(C_1-C_6)$alkoxy, $(C_3-C_6)$cycloalkyl, halo$(C_1-C_6)$alkyloxy, heterocycloalkyl, aryl or heteroaryl; said $(C_1-C_6)$alkyl optionally being substituted with one or more substituents independently selected from the group consisting of halogen, cyano, hydroxyl and oxo.

In one or more embodiments of the present invention $R_1$ represents G3, wherein $X_1$, $X_2$, and $X_3$ are each independently selected from the group consisting of C, CH, N, NH, S and O; and wherein $Y_1$, $Y_2$, $Y_3$, $Y_4$, $Y_5$ and $Y_6$ are each independently selected from the group consisting of C, CH and N; G3 optionally being substituted with one or more substituents independently selected from $R_2$; wherein $R_2$ represents cyano or halogen; or $R_2$ represents $(C_1-C_6)$alkyl, $(C_2-C_6)$alkenyl, $(C_1-C_6)$alkoxy, $(C_3-C_6)$cycloalkyl, halo$(C_1-C_6)$alkyloxy, heterocycloalkyl, aryl or heteroaryl; said $(C_1-C_6)$alkyl optionally being substituted with one or more substituents independently selected from the group consisting of halogen, cyano, hydroxyl and oxo.

In one or more embodiments of the present invention $R_1$ represents G4, wherein $X_1$, $X_2$, and $X_3$ are each independently selected from the group consisting of C, CH, N, NH, S and O; and wherein $Y_1$, $Y_2$, $Y_3$, $Y_4$, $Y_5$ and $Y_6$ are each independently selected from the group consisting of C, CH and N; G4 optionally being substituted with one or more substituents independently selected from $R_2$; wherein $R_2$ represents cyano or halogen; or $R_2$ represents $(C_1-C_6)$alkyl, $(C_2-C_6)$alkenyl, $(C_1-C_6)$alkoxy, $(C_3-C_6)$cycloalkyl, halo$(C_1-C_6)$alkyloxy, heterocycloalkyl, aryl or heteroaryl; said $(C_1-C_6)$alkyl optionally being substituted with one or more substituents independently selected from the group consisting of halogen, cyano, hydroxyl and oxo.

In one or more embodiments of the present invention $R_1$ represents G5, wherein $Y_1$, $Y_2$, $Y_3$, $Y_4$, $Y_5$, $Y_6$, $Y_7$, $Y_8$, $Y_9$ and $Y_{10}$ are each independently selected from the group consisting of C, CH and N; G5 optionally being substituted with one or more substituents independently selected from $R_2$; wherein $R_2$ represents cyano or halogen; or $R_2$ represents $(C_1-C_6)$alkyl, $(C_2-C_6)$alkenyl, $(C_1-C_6)$alkoxy, $(C_3-C_6)$cycloalkyl, halo$(C_1-C_6)$alkyloxy, heterocycloalkyl, aryl or heteroaryl; said $(C_1-C_6)$alkyl optionally being substituted with one or more substituents independently selected from the group consisting of halogen, cyano, hydroxyl and oxo.

In one or more embodiments of the present invention $R_1$ represents $G_1$, wherein at least one of $X_1$ or $X_4$ is selected from the group consisting of N, NH, S and O, and wherein $G_1$ is optionally substituted with one or more substituents independently selected from $R_2$, wherein $R_2$ represents cyano or halogen or $R_2$ represents $(C_1-C_6)$alkyl, $(C_2-C_6)$alkenyl, $(C_1-C_6)$alkoxy, $(C_3-C_6)$cycloalkyl or halo$(C_1-C_6)$alkyloxy, said $(C_1-C_6)$alkyl optionally being substituted with one or more substituents independently selected from the group consisting of halogen.

In one or more embodiments of the present invention $R_1$ represents $G_2$, wherein at least one of $Y_1$ or $Y_5$ represents N, and wherein $G_2$ is optionally substituted with one or more substituents independently selected from $R_2$, wherein $R_2$ represents cyano or halogen or $R_2$ represents $(C_1-C_6)$alkyl, $(C_2-C_6)$alkenyl, $(C_1-C_6)$alkoxy, $(C_3-C_6)$cycloalkyl or halo$(C_1-C_6)$alkyloxy, said $(C_1-C_6)$alkyl optionally being substituted with one or more substituents independently selected from the group consisting of halogen.

In one or more embodiments of the present invention $R_1$ represents $G_3$, wherein the point of attachment to 3-O-ingenol occurs through $X_1$ or $X_3$ and wherein $X_2$ is selected from the group consisting of N, NH, S and O;

or $R_1$ represents $G_3$, wherein the point of attachment to 3-O-ingenol occurs through $X_2$ and wherein at least one of $X_1$ and $X_3$ is selected from the group consisting of N, NH, S and O; and wherein $G_3$ is optionally substituted with one or more substituents independently selected from $R_2$, wherein $R_2$ represents cyano or halogen or $R_2$ represents $(C_1-C_6)$alkyl, $(C_2-C_6)$alkenyl, $(C_1-C_6)$alkoxy, $(C_3-C_6)$cycloalkyl or halo$(C_1-C_6)$alkyloxy, said $(C_1-C_6)$alkyl optionally being substituted with one or more substituents independently selected from the group consisting of halogen.

In one or more embodiments of the present invention $R_1$ represents $G_4$, wherein the point of attachment to 3-O-ingenol occurs through $Y_1$ and wherein $Y_2$ represents N;

or $R_1$ represents $G_4$, wherein the point of attachment to 3-O-ingenol occurs through $Y_2$ and wherein at least one of $Y_1$ and $Y_3$ represents N;

and wherein $G_4$ is optionally substituted with one or more substituents independently selected from $R_2$, wherein $R_2$ represents cyano or halogen or $R_2$ represents $(C_1-C_6)$alkyl, $(C_2-C_6)$alkenyl, $(C_1-C_6)$alkoxy, $(C_3-C_6)$cycloalkyl or halo$(C_1-C_6)$alkyloxy, said $(C_1-C_6)$alkyl optionally being substituted with one or more substituents independently selected from the group consisting of halogen.

In one or more embodiments of the present invention $R_1$ represents $G_5$, wherein the point of attachment to 3-O-ingenol occurs through $Y_1$ and wherein $Y_2$ represents N;

or $R_1$ represents $G_5$, wherein the point of attachment to 3-O-ingenol occurs through $Y_2$ and wherein at least one of $Y_1$ and $Y_3$ represents N;

and wherein $G_5$ is optionally substituted with one or more substituents independently selected from $R_2$, wherein $R_2$ represents cyano or halogen or $R_2$ represents $(C_1-C_6)$alkyl, $(C_2-C_6)$alkenyl, $(C_1-C_6)$alkoxy, $(C_3-C_6)$cycloalkyl or halo$(C_1-C_6)$alkyloxy, said $(C_1-C_6)$alkyl optionally being substituted with one or more substituents independently selected from the group consisting of halogen.

In one or more embodiments of the present invention $R_2$ represents cyano or halogen; or $R_2$ represents $(C_1-C_6)$alkyl, $(C_2-C_6)$alkenyl, $(C_1-C_6)$alkoxy, $(C_3-C_6)$cycloalkyl, halo$(C_1-C_6)$alkyloxy, heterocycloalkyl, aryl or heteroaryl; said $(C_1-C_6)$alkyl optionally being substituted with one or more substituents independently selected from the group consisting of halogen, cyano, hydroxyl and oxo.

In one or more embodiments of the present invention $R_2$ represents cyano or halogen; or $R_2$ represents $(C_1-C_6)$alkyl, $(C_2-C_6)$alkenyl, $(C_1-C_6)$alkoxy, $(C_3-C_6)$cycloalkyl or halo$(C_1-C_6)$alkyloxy; said $(C_1-C_6)$alkyl optionally being substituted with one or more substituents independently selected from the group consisting of halogen, cyano, hydroxyl and oxo.

In one or more embodiments of the present invention $R_2$ represents cyano or halogen; or $R_2$ represents $(C_1-C_6)$alkyl, $(C_2-C_6)$alkenyl, $(C_1-C_6)$alkoxy, $(C_3-C_6)$cycloalkyl or halo$(C_1-C_6)$alkyloxy; said $(C_1-C_6)$alkyl optionally being substituted with one or more substituents independently selected from the group consisting of halogen.

In one or more embodiments of the present invention $R_2$ represents cyano or halogen; or $R_2$ represents $(C_1-C_6)$alkyl, $(C_2-C_6)$alkenyl, $(C_1-C_6)$alkoxy or halo$(C_1-C_6)$alkyloxy; said $(C_1-C_6)$alkyl optionally being substituted with one or more substituents independently selected from the group consisting of halogen.

In one or more embodiments of the present invention R$_2$ represents cyano or halogen.

In one or more embodiments of the present invention R$_2$ represents (C$_1$-C$_6$)alkyl, (C$_2$-C$_6$)alkenyl, (C$_1$-C$_6$)alkoxy, (C$_3$-C$_6$)cycloalkyl or halo(C$_1$-C$_6$)alkyloxy.

In one or more embodiments of the present invention R$_2$ represents (C$_1$-C$_6$)alkyl, (C$_2$-C$_6$)alkenyl, (C$_1$-C$_6$)alkoxy, (C$_3$-C$_6$)cycloalkyl or halo(C$_1$-C$_6$)alkyloxy; said (C$_1$-C$_6$)alkyl optionally being substituted with one or more substituents independently selected from the group consisting of halogen.

In one or more embodiments of the present invention R$_2$ represents (C$_1$-C$_6$)alkyl, (C$_1$-C$_6$)alkoxy or (C$_3$-C$_6$)cycloalkyl; said (C$_1$-C$_6$)alkyl optionally being substituted with one or more substituents independently selected from the group consisting of halogen.

Any combination of two or more embodiments described herein is considered within the scope of the present invention, particularly R$_1$ and R$_2$ can be combined in any combination as described herein.

In one or more embodiments of the present invention, the compounds of general formula I have a molecular weight below 700 Dalton, such as below 650 Dalton, e.g. below 600 Dalton, or below 550, 500 or 450 Dalton.

In one or more embodiments of the present invention, the compounds of general formula I have a calculated log P value above 1.5 or above 2 or above 2.5.

In one or more embodiments of the present invention, the compounds of general formula I have a Rel EC$_{50}$ value in neutrophil oxidative burst assay of less than 1 micromolar, or of less than 500, 100, 50, 20 or 10 nanomolar.

In one or more embodiments of the present invention, the compounds of general formula I have a Rel EC$_{50}$ value in HeKa cytokine release (IL-8) assay of less than 1 micromolar, or of less than 500, 100, 50, 20 or 10 nanomolar.

In one or more embodiments of the present invention, the compounds of general formula I have a EC$_{50}$ value in the HeLa Necrosis assay of less than 1 micromolar, or of less than 500, 350, 250 or 150 nanomolar.

An embodiment of the present invention provides a compound of general formula I, wherein R$_1$ is selected from the group of heteroaryl consisting of a five-membered monocyclic heteroaromatic ring, a six-membered monocyclic heteroaromatic ring, a five-membered monocyclic heteroaromatic ring fused to a six-membered heteroaromatic ring, a five-membered monocyclic heteroaromatic ring fused to a five-membered heteroaromatic ring, a six-membered monocyclic heteroaromatic ring fused to a six-membered heteroaromatic ring, a five-membered monocyclic heteroaromatic ring fused to a six-membered aromatic ring and a six-membered monocyclic heteroaromatic ring fused to a six-membered aromatic ring.

An embodiment of the present invention provides a compound of general formula I, wherein R$_1$ represents heteroaryl; said heteroaryl optionally being substituted with one or more substituents independently selected from R$_2$; and wherein said heteroaryl is selected from the group consisting of

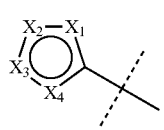

G1

-continued

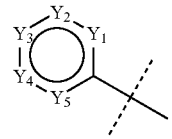

G2

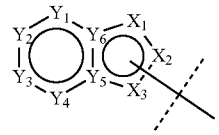

G3

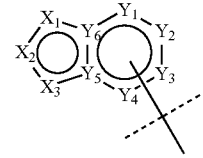

G4

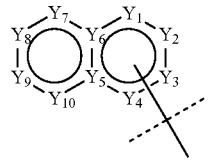

G5 wherein X$_1$, X$_2$, X$_3$ and X$_4$ are each independently selected from the group consisting of C, CH, N, NH, S and O; and wherein Y$_1$, Y$_2$, Y$_3$, Y$_4$, Y$_5$, Y$_6$, Y$_7$, Y$_8$, Y$_9$ and Y$_{10}$ are each independently selected from the group consisting of C, CH and N.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline forms, such as polymorphs and pseudopolymorphs, and also mixtures thereof.

Compounds of formula I may or may not comprise asymmetrically substituted (chiral) carbon atoms which give rise to the existence of isomeric forms, e.g. enantiomers and possibly diastereomers. The present invention relates to all such isomers, either in optically pure form or as mixtures thereof (e.g. racemic mixtures or partially purified optical mixtures). Pure stereoisomeric forms of the compounds and the intermediates of this invention may be obtained by the application of procedures known in the art. The various isomeric forms may be separated by physical separation methods such as selective crystallization and chromatographic techniques, e.g. high pressure liquid chromatography using chiral stationary phases. Enantiomers may be separated from each other by selective crystallization of their diastereomeric salts which may be formed with optically active amines, such as I-ephedrine, or with optically active acids. Optically purified compounds may subsequently be liberated from said purified diastereomeric salts. Enantiomers may also be resolved by the formation of diastereomeric derivatives. Alternatively, enantiomers may be separated by chromatographic techniques using chiral stationary phases. Pure stereoisomeric forms may also be derived from the corresponding pure stereoisomeric forms of the appropriate starting materials, provided that the reaction occur stereoselectively or stereospecifically. Preferably, if a specific stereoisomer is desired, said compound will be synthesized by stereoselective or stereospecific methods of preparation. These methods will advantageously employ chiral pure starting materials.

Furthermore, when a double bond or a fully or partially saturated ring system is present in the molecule geometric isomers may be formed. It is intended that any geometric isomer, as separated, pure or partially purified geometric isomers or mixtures thereof are included within the scope of the invention.

Compounds of the invention which comprise free hydroxyl groups or free carboxylic acid groups may also exist in the form of pharmaceutically acceptable, physiologically cleavable esters, and are as such included within the scope of the present invention. Such pharmaceutically acceptable esters are preferably prodrug ester derivatives, such being convertible by solvolysis or cleavage under physiologically conditions to the corresponding compounds of the invention which comprise free hydroxyl groups or free carboxylic acid groups respectively, e.g. in-vivo hydrolysable.

In one or more embodiments of the present invention, the compounds of formula I as defined above are useful in therapy and in particular useful for treatment of cutaneous warts, genital warts, actinic keratosis, squamous cell carcinoma (SCC), basal cell carcinoma (BCC), lentigo maligna, cervical intraepithelial neoplasia, anal intraepithelial neoplasia or vulva intraepithelial neoplasia.

In an embodiment the invention provides use of a compound according to formula I in the manufacture of a medicament for the treatment, amelioration or prophylaxis of physiological disorders or diseases associated with hyperplasia, neoplasia or dysplasia.

In an embodiment the invention provides use of a compound according to formula I in the manufacture of a medicament for the treatment of cutaneous warts, genital warts, actinic keratosis, squamous cell carcinoma (SCC), basal cell carcinoma (BCC), lentigo maligna, cervical intraepithelial neoplasia, anal intraepithelial neoplasia or vulva intraepithelial neoplasia.

In an embodiment the invention provides use of a compound according to formula I in the manufacture of a medicament for the treatment of actinic keratosis.

In an embodiment the invention provides a method of preventing, treating, amelioration or prophylaxis of cutaneous warts, genital warts, actinic keratosis, squamous cell carcinoma (SCC), basal cell carcinoma (BCC), lentigo maligna, cervical intraepithelial neoplasia, anal intraepithelial neoplasia or vulva intraepithelial neoplasia.
by administration to a subject in need thereof a compound according to formula I, optionally together with a pharmaceutically acceptable carrier or one or more excipients, optionally in combination with other therapeutically active compounds.

In an embodiment the invention provides a method of treating actinic keratosis by administration to a subject in need thereof a compound according to formula I, optionally together with a pharmaceutically acceptable carrier or one or more excipients, optionally in combination with other therapeutically active compounds.

In one or more embodiments of the present invention, the compounds of formula I as defined above are useful in therapy and in particular useful for treatment or amelioration of photodamaged skin or seborrheic keratosis.

In an embodiment the invention provides use of a compound according to formula I in the manufacture of a medicament for the treatment or amelioration of cosmetic indications.

In an embodiment the invention provides use of a compound according to formula I in the manufacture of a medicament for the treatment or amelioration of photodamaged skin or seborrheic keratosis.

In an embodiment the invention provides a method of treating or ameliorating photodamaged skin or seborrheic keratosis by administration to a subject in need thereof a compound according to formula I, optionally together with a pharmaceutically acceptable carrier or one or more excipients, optionally in combination with other therapeutically active compounds.

In an embodiment the invention provides a pharmaceutical composition comprising a compound of formula I, wherein the composition is suitable for topical administration.

In an embodiment the invention provides use of a compound according to formula I in the manufacture of a pharmaceutical composition for the treatment or amelioration of a disease, disorder or condition responsive to stimulation of neutrophil oxidative burst.

In an embodiment the invention provides use of a compound according to formula I in the manufacture of a pharmaceutical composition for the treatment or amelioration of a disease, disorder or condition responsive to stimulation of keratinocyte IL-8 release.

In an embodiment the invention provides use of a compound according to formula I in the manufacture of a pharmaceutical composition for the treatment or amelioration of a disease, disorder or condition responsive to induction of necrosis.

In an embodiment the invention provides a method of preventing, treating, amelioration or prophylaxis of physiological disorders or diseases responsive to stimulation of neutrophil oxidative burst by administration to a subject in need thereof a compound according to formula I.

In an embodiment the invention provides a method of preventing, treating, amelioration or prophylaxis of physiological disorders or diseases responsive to stimulation of keratinocyte IL-8 release by administration to a subject in need thereof a compound according to formula I.

In an embodiment the invention provides a method of preventing, treating, amelioration or prophylaxis of physiological disorders or diseases responsive to responsive to induction of necrosis by administration to a subject in need thereof a compound according to formula I.

In an embodiment the invention provides a compound according to formula I for use in the treatment or amelioration of a disease, disorder or condition responsive to stimulation of neutrophil oxidative burst.

In an embodiment the invention provides a compound according to formula I for use in the treatment or amelioration of a disease, disorder or condition responsive to stimulation of keratinocyte IL-8 release.

In an embodiment the invention provides a compound according to formula I for use in the treatment or amelioration of a disease, disorder or condition responsive to induction of necrosis.

Besides being useful for human treatment, the compounds of the present invention may also be useful for veterinary treatment of animals including mammals such as horses, cattle, sheep, pigs, dogs, and cats.

Pharmaceutical Compositions of the Invention

For use in therapy, compounds of the present invention are typically in the form of a pharmaceutical composition. The invention therefore relates to a pharmaceutical composition comprising a compound of formula I, together with a pharmaceutically acceptable excipient or vehicle. The excipient must be "acceptable" in the sense of being compatible with the other ingredients of the composition and not deleterious to the recipient thereof.

Pharmaceutical compositions of the invention may be in unit dosage form such as tablets, pills, capsules, powders, granules, elixirs, syrups, emulsions, ampoules, suppositories or parenteral solutions or suspensions; for oral, parenteral, opthalmic, transdermal, intra-articular, topical, pulmonal, nasal, buccal, sublingual or rectal administration or in any other manner appropriate for the formulation of compounds of the invention and in accordance with accepted practices such as those disclosed in *Remington: The Science and Practice of Pharmacy,* $21^{st}$ ed., 2000, Lippincott Williams & Wilkins.

For oral administration in the form of a tablet or capsule, a compound of formula I may suitably be combined with an oral, non-toxic, pharmaceutically acceptable carrier such as ethanol, glycerol, water or the like. Furthermore, suitable binders, lubricants, disintegrating agents, flavouring agents and colourants may be added to the mixture, as appropriate. Suitable binders include, e.g., lactose, glucose, starch, gelatin, *acacia* gum, tragacanth gum, sodium alginate, carboxymethylcellulose, polyethylene glycol, waxes or the like. Lubricants include, e.g., sodium oleate, sodium stearate, magnesium stearate, sodium benzoate, sodium acetate, sodium chloride or the like. Disintegrating agents include, e.g., starch, methyl cellulose, agar, bentonite, xanthan gum or the like. Additional excipients for capsules include macrogols or lipids.

For the preparation of solid compositions such as tablets, the active compound of formula I is mixed with one or more excipients, such as the ones described above, and other pharmaceutical diluents such as water to make a solid preformulation composition containing a homogenous mixture of a compound of formula I. The term "homogenous" is understood to mean that the compound of formula I is dispersed evenly throughout the composition so that the composition may readily be subdivided into equally effective unit dosage forms such as tablets or capsules.

In the form of a dosage unit, the compound may be administered one or more times a day at appropriate intervals, always depending, however, on the condition of the patient, and in accordance with the prescription made by the medical practitioner. Conveniently, a dosage unit of a formulation contain between 0.01 mg and 200 mg, preferably between 0.01 mg and 20 mg, such as 0.01-5 mg of a compound of formula I.

A suitable dosage of the compound of the invention will depend, inter alia, on the age and condition of the patient, the severity of the disease to be treated and other factors well known to the practising physician. The compound may be administered either orally, parenterally or topically according to different dosing schedules, e.g. daily or with weekly intervals. In general a single dose will be in the range from 0.01 to 200 mg/kg body weight. The compound may be administered as a bolus (i.e. the entire daily dose is administered at once) or in divided doses two or more times a day.

If the treatment involves administration of another therapeutically active compound it is recommended to consult *Goodman & Gilman's The Pharmacological Basis of Therapeutics,* $9^{th}$ Ed., J. G. Hardman and L. E. Limbird (Eds.), McGraw-Hill 1995, for useful dosages of said compounds. The administration of a compound of the present invention with one or more other active compounds may be either concomitantly or sequentially.

Liquid formulations for either oral or parenteral administration of the compound of the invention include, e.g., aqueous solutions, syrups, aqueous or oil suspensions and emulsion with edible oils such as cottonseed oil, sesame oil, coconut oil or peanut oil. Suitable dispersing or suspending agents for aqueous suspensions include synthetic or natural gums such as tragacanth, alginate, *acacia*, dextran, sodium carboxymethylcellulose, gelatin, methylcellulose or polyvinylpyrolidone.

For parenteral administration, e.g. intramuscular, intraperitoneal, subcutaneous or intravenous injection or infusion, the pharmaceutical composition preferably comprises a compound of formula I dissolved or solubilised in an appropriate, pharmaceutically acceptable solvent. For parenteral administration, the composition of the invention may include a sterile aqueous or non-aqueous solvent, in particular water, isotonic saline, isotonic glucose solution, buffer solution or other solvent conventionally used for parenteral administration of therapeutically active substances. The composition may be sterilised by, for instance, filtration through a bacteria-retaining filter, addition of a sterilising agent to the composition, irradiation of the composition, or heating the composition. Alternatively, the compound of the invention may be provided as a sterile, solid preparation, e.g. a freeze-dried powder, which is dissolved in sterile solvent immediately prior to use. The composition intended for parenteral administration may additionally comprise conventional additives such as stabilisers, buffers or preservatives, e.g. antioxidants such as methyl hydroxybenzoate or the like.

Compositions for rectal administration may be in the form of a suppository incorporating the active ingredient and a carrier such as cocoa butter, or in the form of an enema. Compositions suitable for intra-articular administration may be in the form of a sterile aqueous preparation of the active ingredient which may be in microcrystalline form, for example, in the form of an aqueous microcrystalline suspension. Liposomal formulations or biodegradable polymer systems may also be used to present the active ingredient for both intra-articular and ophthalmic administration.

Compositions suitable for topical administration, including ophthalmic treatment, include liquid or semi-liquid preparations such as liniments, lotions, gels, applicants, oil-in-water or water-in-oil emulsions such as creams, ointments or pastes; or solutions or suspensions such as drops. Compositions for ophthalmic treatment may preferably additionally contain a cyclodextrin. Compositions suitable for administration to the nasal or buccal cavity or for inhalation include powder, self-propelling and spray formulations, such as aerosols and atomizers.

Human skin, in particular the outer layer, the stratum corneum, provides an effective barrier against penetration of microbial pathogens and toxic chemicals. While this property of skin is generally beneficial, it complicates the dermal administration of pharmaceuticals in that a large quantity, if not most, of the active ingredient applied on the skin of a patient suffering from a dermal disease may not penetrate into the viable layers of the skin where it exerts its activity.

Penetration of the skin is facilitated by addition of penetration enhancers which include isopropyl alcohol, sulphoxides, azones, pyrrolidines, alkanols, and glycols. In embodiments of the invention the penetrations enhancers includes DMSO, laurocapram, 2-pyrrolidone, decanol and propylene glycol. In an embodiment of the invention the penetration enhancer is isopropyl alcohol.

In embodiments of the invention the therapeutically active compound is dissolved in a suitable solvent. Suitable solvents are glycols, ketone, acetates and ethers. Ingenol compounds have been shown to have good stability in alcohols such as benzyl alcohol and isopropyl alcohol. In general, ingenol compounds have previously shown to have good stability at low pH. In embodiments of the present invention pH the pharmaceutical formulation is below 7. In embodiments of the present invention the pH of the pharmaceutical formulation is below 6. In embodiments of the present invention the pH of the pharmaceutical formulation is below 4.5. In embodiments of the present invention the pH of the pharmaceutical formulation is below 4.0. In embodiments of the present invention the pH of the pharmaceutical formulation is below 4.5 and no less than 2.5. In embodiments of the present invention the pH of the pharmaceutical formulation is below 4.0 and no less than 2.5. The preferred pH range can be obtained by including an appropriate buffer. In an embodiment of the invention the buffer is an acetate buffer. In embodiments of the invention a citrate buffer is used. In embodiments of the invention a mixed citrate-phosphate buffer is used.

In one embodiment, the composition is an ointment. According to the current FDA classification, an ointment is a semisolid dosage from which may contain water and volatile substances in an amount of up to 20% by weight and which contains more than 50% by weight of hydrocarbons, waxes or polyols in the vehicle. Thus, according to the invention, the ointment may be a water-in-oil composition in which case the nanosuspension may be added as such to the lipophilic components of the composition, such that the composition contains up to 10% by weight or, preferably, up to 5% by weight of the aqueous phase. Alternatively, the composition may be a non-aqueous ointment which contains less than about 2%, preferably less than 1%, of free water by weight of the composition.

The ointment carrier may suitably contain a paraffin selected from paraffins consisting of hydrocarbons with chain lengths from $C_{5-60}$ and mixtures thereof. A frequently used ointment carrier is petrolatum, or white soft paraffin, which is composed of hydrocarbons of different chain lengths, peaking at about $C_{40-44}$, or a mixture of petrolatum and liquid paraffin (consisting of hydrocarbons of different chain lengths peaking at $C_{28-40}$). While petrolatum provides occlusion of the treated skin surface, reducing transdermal loss of water and potentiating the therapeutic effect of the active ingredient in the composition, it tends to have a greasy and/or tacky feel which persists for quite some time after application, and it is not easily spreadable. It may therefore be preferred to employ paraffins consisting of hydrocarbons of a somewhat lower chain length, such as paraffins consisting of hydrocarbons with chain lengths peaking at $C_{14-16}$, $C_{18-22}$, $C_{20-22}$, $C_{20-26}$ or mixtures thereof. It has been found that such paraffins are more cosmetically acceptable in that they are less tacky and/or greasy on application and more easily spreadable. They are therefore expected to result in improved patient compliance. Suitable paraffins of this type are manufactured by Sonneborn and marketed under the trade name Sonnecone, e.g. Sonnecone CM, Sonnecone DM1, Sonnecone DM2 and Sonnecone HV. These paraffins are further disclosed and characterized in WO08/141078 which is incorporated herein by reference. (The hydrocarbon composition of the paraffins has been determined by gas chromatography.)

To impart a desired viscosity to the composition, it may suitably include a lipophilic viscosity-increasing ingredient such as a wax. The wax may be a mineral wax composed of a mixture of high molecular weight hydrocarbons, e.g. saturated $C_{35-20}$ alkanes, such as microcrystalline wax. Alternatively, the wax may be a vegetable or animal wax, e.g. esters of $C_{14-32}$ fatty acids and $C_{14-32}$ fatty alcohols, such as beeswax. The amount of viscosity-increasing ingredient may vary according to the viscosifying power of the ingredient, but may typically be in the range of about 1-20% by weight of the composition. When the viscosity-increasing ingredient is microcrystalline wax it is typically present in an amount in the range of about 5-15% by weight, e.g. about 10% by weight, of the composition.

To maintain good physical stability of the composition, in particular to avoid separation of the aqueous and lipid phases therein, it may be advantageous to include a water-in-oil emulsifier with an HLB value of 3-8. Examples of such emulsifiers are polyoxyethylene $C_{8-22}$ alkyl ethers, e.g. polyoxyethylene stearyl ether, polyoxyethylene cetyl ether, polyoxyethylene oleyl ether or polyoxyethylene lauryl ether. The amount of emulsifier is typically in the range of 2-10% w/w of the composition.

In another embodiment, the composition is a cream which may comprise similar components to the ointment, but which is typically an oil-in-water-emulsion containing a substantial amount of water.

The composition may also comprise other components commonly used in dermal formulations, e.g. antioxidants (e.g. alpha-tocopherol), preservatives such as benzyl alcohol, sodium edetate, pigments, skin soothing agents, skin healing agents and skin conditioning agents such as urea, allantoin or bisabolol, cf. *CTFA Cosmetic Ingredients Handbook*, $2^{nd}$ Ed., 1992. In an embodiment of the invention the preservative is benzyl alcohol.

In an embodiment the composition is a gel. Suitable gelling agents include, water soluble cellulose derived polymers, such as hydroxyalkyl cellulose polymers. In embodiments of the invention the polymers are hydroxymethylcellulose, hydroxyethylcellulose, hydroxypropylcellulose and hydroxypropylmethylcellulose. Other gelling agents are celluloses such as carboxymethyl cellulose, methylhydroxyethyl cellulose and methyl cellulose, carbomer such as carbopol and carrageenans. In embodiments of the invention the gelling agent is cellulose derived. In embodiments of the invention the cellulose is a hydroxyalkylcellulose, such as hydroxyethylcellulose.

In an embodiment of the invention the composition comprises active compound, penetration enhancer, preservative, gelling agent and buffer at a pH of below 4 and not less than 2.5. For topical administration, the compound of formula I may typically be present in an amount of from 0.001 to 20% by weight of the composition, such as 0.01% to about 10%. In embodiments of the present invention the active compound is present in 0.05-1%. In an embodiment of the present invention the active compound is present in 0.01-0.5%. In an embodiment of the present invention the active compound is present in a concentration of around 0.1%. In an embodiment of the invention the composition comprises 0.005-0.1% active compound, 20-40% isopropyl alcohol, 0.5-10% benzyl alcohol, 0.5-5% hydroxyl ethyl cellulose and citrate buffer to 100%.

Formulation of ingenol derivatives in a gel for topical application has been described in WO07/068963, which is incorporated by reference.

Methods of Preparation

The compounds of formula I may for example be prepared using the reactions and techniques outlined below together with methods known in the art of synthetic organic chemistry, or variations thereof as appreciated by those skilled in the art. Preferred methods include, but are not limited to, those described below. The reactions are carried out in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognized by one skilled in the art. Not all compounds falling into a given class may be compatible with some of the reaction conditions required in some of the methods described. Such restrictions to the substituents which are compatible with the reaction conditions will be readily apparent to one skilled in the art and alternative methods can be used. The compounds of the present invention or any intermediate may be purified if required using standard methods well known to a synthetic organist chemist, e.g. methods described in W. Armarego "Purification of Laboratory Chemicals", Butterworth-Heinemann, 6$^{th}$ ed. 2009. Starting materials are either known compounds, commercially available, or they may be prepared by routine synthetic methods well known to a person skilled in the art.

The compounds of the invention may for example be prepared according to the following non-limiting general methods and examples.

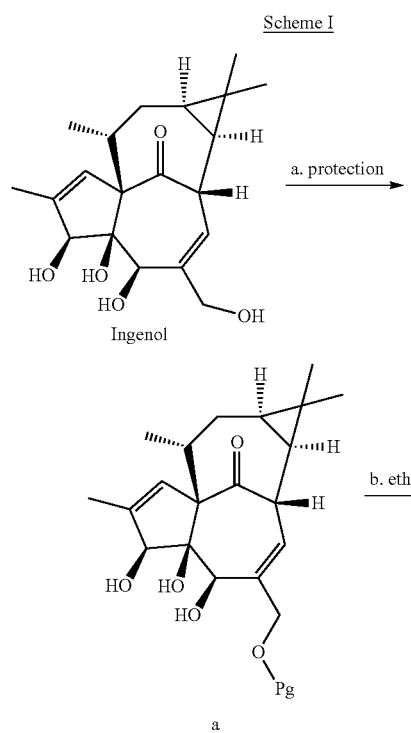

Scheme I

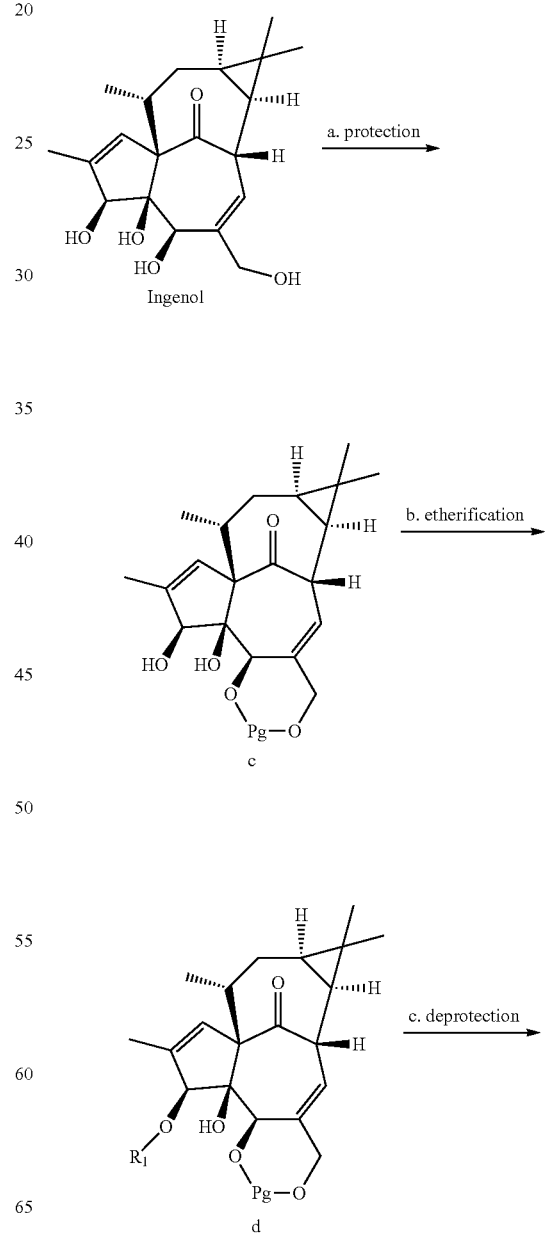

Scheme 2

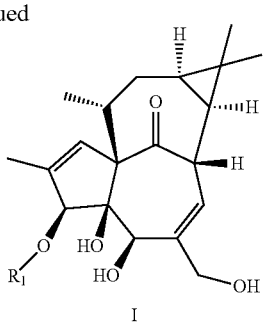

I

The compounds of the general formula I can for example be synthesised according to Scheme 1 or 2 by reacting ingenol with a hydroxyl protecting agent or a dihydroxyl protecting agent to afford the protected ingenol derivatives a or c according to methods described in, but not limited to "Protective Groups in Organic Synthesis", 4th ed. P. G. M. Wuts; T. W. Greene, John Wiley, 2007 or in P. J. Kocienski, "Protecting Groups", 3rd ed. G. Thieme, 2003 and references cited therein.

For example compound a, wherein the protective group (Pg) is triphenylmethyl, can be synthesised by reacting ingenol with a triphenylmethyl reagent such as triphenylmethylpyridinium fluoroborate or triphenylmethyl chloride in a suitable solvent such as pyridine, N,N-dimethylformamide or dichloromethane in the presence or in the absence of base (e.g. Opferkuch et. al., Z. Naturforschung, (1981), 36B, 878). Compound a, wherein the protective group (Pg) is silyl, can for example be synthesised by reacting ingenol with a silyl chloride such as tert-butyldimethylsilyl chloride, tert-butyldiphenylsilyl chloride or triisopropylsilyl chloride in a suitable solvent such as N,N-dimethylformamide, pyridine, dichloromethane, tetrahydrofuran or acetonitrile in the presence of a suitable base such as imidazole, triethylamine, N,N-diisopropylethylamine or 4-(N,N-dimethylamino)pyridine (e.g. Sorg, B. et. al, Z. Naturforsch., (1982), 37B, 1640-47), or by reacting ingenol with a silyl triflate such as tert-butyldimethylsilyl trifluoromethanesulfonate in a suitable solvent such as dichloromethane in the presence of a suitable base such as triethylamine.

Compound a wherein Pg is 2-tetrahydropyranyl, can for example be synthesised by reacting ingenol with dihydropyran in a suitable solvent such as dichloromethane or acetonitrile in the presence of a suitable acid such as p-toluenesulfonic acid.

Compound c wherein the protective group (Pg) represents an acetal such as benzylidene acetal can for example be prepared by reacting ingenol with benzaldehyde or benzaldehyde dimethyl acetal in a suitable solvent such as dichloromethane or N,N-dimethylformamide in the presence of a suitable acid such as p-toluenesulfonic acid. Compound c wherein the protective group (Pg) represents a ketal such as isopropylidene ketal can for example be synthesised by reacting ingenol with a ketone such as acetone or a dimethoxy ketal such as 2,2-dimethoxy propane in a suitable solvent such as dichloromethane or N,N-dimethylformamide in the presence of a suitable acid such as p-toluenesulfonic acid (e.g B. Sorg, Z. Naturforsch. (1982), 37b, 748-756). Acetone and 2,2-dimethoxy propane can also act as solvents.

As depicted in scheme 1 and 2 the protected ingenol derivatives a or c may be reacted to give compounds of the general formula b or d according to methods frequently described in the literature (e.g. Saari, R. et al. Bioorg. Med. Chem. (2011), 19, 935-950; Lloung, M. et al. Heterocycles (2004), 63, 297-308; Lin, N.-H. et al. Bioorg. Med. Chem. Lett. (1999), 9, 2747-2752; Fukuwa, I. et al. J. Chem. Soc., Perkin Trans. 2 (1992), 377-382; Uray, G. Synthesis 1984, 679-681; Gerrity K. et al. J. Med. Chem. (1978), 21, 123-126). 2-Halo-heteroaromatic compounds for example react with alcohols in the presence of a base, such as alkali (Na, K, Cs) carbonates, caesium fluoride, potassium tert-butoxide, sodium hydroxide, potassium hydroxide and sodium hydride, in solvents, such as acetonitrile, t-BuOH, THF, 1,4-dioxane, DMSO and DMF, to give 2-heteroaryl ethers. 2-Fluoro-heteroaromatic compounds react with the corresponding alcohols more readily than the corresponding chloro- or bromo-compounds. If they are not reactive enough, 2-chloro- or bromo-compounds can be converted to the corresponding 2-fluoro-heteroaryl compounds (e.g. Ahmadi, A. Asian J. Chem. (2009), 9, 6651-6655) and the reaction mixtures can be used directly in the next step without isolation of 2-fluoro-heteroaryl compounds.

Compounds of general formulae b and d can e.g. be prepared by the copper(I) catalysed reactions of haloheteroaryl compounds with compounds of general formulae a and c (for this type reaction, see: Stocking, E. M. et al. Bioorg. Med. Chem. (2010), 20, 2755-2760; Benaskar, F. et al. Tetrahedron Lett. (2010), 248-251; Altman, R. A. J. Org. Chem. (2008), 73, 284-286; Keegstra, M. A. Tetrahedron (1992), 3633-3652. For a review, see: Evano, G. Chem. Rev. (2008), 108, 3054-3131). Compounds of general formulae b and d can e.g. be prepared by the Pd-catalysed reactions of haloheteroaryl compounds with compounds of general formulae a and c (for this type reaction, see: Vorogushin, A. V. et al. J. Am. Chem. Soc. (2005), 127, 8146-8149).

The compounds of formula I may be prepared by selective removal of the protective groups Pg from the compounds of the general structure b or d according to methods for deprotection of hydroxyl or dihydroxyl protective groups described, in but not limited to "Protective Groups in Organic Synthesis", 4th ed. P. G. M. Wuts; T. W. Greene, John Wiley, 2007 or in P. J. Kocienski, "Protecting Groups", 3rd ed. G. Thieme, 2003 and references cited therein.

Compounds of general formula I can for example be prepared from compounds of general formula d wherein Pg represents an acetal such as benzylidene acetal or a ketal such as an isopropylidene ketal by cleavage of the protecting group in the presence of a suitable acid such as aqueous hydrogen chloride, acetic acid, trifluoroacetic acid or p-toluenesulfonic acid in a suitable solvent such as methanol or aqueous tetrahydrofuran. Compounds of general formula I can for example be prepared from compounds of general formula b wherein Pg represents an alkoxyalkyl such as 2-tetrahydropyranyl by cleaving the acetal moiety, for example by acid catalysed cleavage in the presence of a suitable acid such as p-toluenesulfonic acid in a suitable solvent such as methanol. Compounds of general formula I can for example be prepared from compounds of general formula b wherein Pg represents silyl such as tert-butyldimethylsilyl by reacting compound b with a suitable acid such as hydrogen chloride in a suitable solvent such as methanol or by reacting with a fluoride source such as tetra n-butylammonium fluoride or tetrafluorosilane in a suitable solvent such as tetrahydrofuran or acetonitrile. Compounds of general formula I can for example be prepared from compounds of general formula b wherein Pg represents triphenylmethyl by reacting compound b with a suitable acid such as formic acid or trifluoroacetic acid in a suitable solvent such as ether, methanol or dichloromethane.

GENERAL PROCEDURES, PREPARATIONS AND EXAMPLES

All the starting materials used are commercially available, unless otherwise described. For 1H nuclear magnetic resonance (NMR) spectra, chemical shift values (δ) (in ppm) are quoted; tetramethylsilane (δ=0.00) is as standard. The value of a defined singlet (s), doublet (d), triplet (t), quartet (q)) or a range (m) is given. All organic solvents used were anhydrous, unless otherwise specified. Flash chromatography was performed on silica gel. Appropriate mixtures of ethyl acetate and heptane were used as eluents unless otherwise noted. Compounds were detected on TLC plates by development with aqueous potassium permanganate solution.

The following abbreviations have been used throughout:
Abs absolute
DCM dichloromethane
DMF N,N'-Dimethylformamide
DMSO dimethyl sulfoxide
EtOAc ethyl acetate
h hour(s)
HPLC High pressure liquid chromatography
L liter
m milli
min minutes
MS Mass spectrometry
NMR nuclear magnetic resonance
Rel relative
rt room temperature
TFA trifluoroacetic acid
THF tetrahydrofuran
v volume

PREPARATIONS AND EXAMPLES

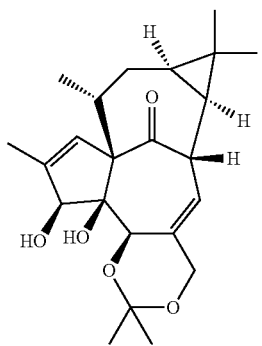

Ingenol-5,20-acetonide

Ingenol (1.00 g, 2.30 mmol) was dissolved in a solution of p-toluenesulphonic acid monohydrate in acetone (0.47 mg/mL, 22.5 mL). The solution was stirred at room temperature for 25 min. To this solution was added a saturated aqueous solution of NaHCO$_3$ (0.2 mL). The obtained mixture was concentrated in vacuo. The residue was taken up in brine and extracted with ethyl acetate. The combined organic phases were dried over sodium sulfate and concentrated in vacuo. The residue was purified by flash chromatography (heptane/ethyl acetate 19:1 heptane/ethyl acetate 0:1), giving the title compound as a white solid (616 mg, 69%). (See also: Opferkuch, H. J. et. al., *Z. Naturforsch.*, (1981), 86b, 878-887.)

$^1$H NMR (300 MHz, CDCl$_3$) δ 5.91 (q, J=1.5 Hz, 1H), 5.79 (m, 1H), 4.25 (d, J=4.5 Hz, 1H), 4.20-4.07 (m, 3H), 3.93 (s, 1H), 3.51 (s, 1H), 2.57-2.41 (m, 2H), 2.25 (ddd, J=15.7, 8.4, 2.9 Hz, 1H), 1.85 (d, J=1.5 Hz, 3H), 1.77 (dt, J=15.8, 5.9 Hz, 1H), 1.41 (s, 3H), 1.35 (s, 3H), 1.13 (s, 3H), 1.05 (s, 3H), 1.00-0.87 (m, 4H), 0.70 (td, J=8.4, 6.4 Hz, 1H).

General Procedures for the Preparation of Compounds of General Formula II

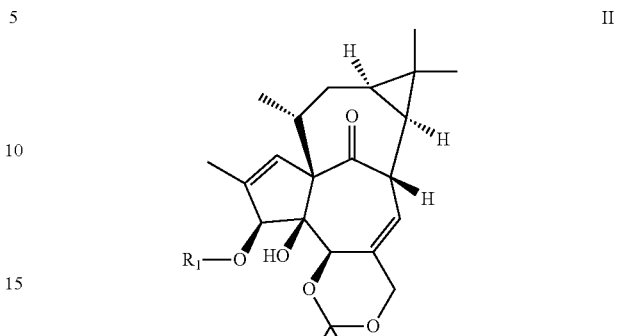

Procedure a

Ingenol-5,20-acetonide (0.13 mmol) dissolved in DMF (0.3 ml) was added a heteroaryl halide (0.65 mmol) and caesium carbonate (0.26 mmol). The mixture was stirred at 60° C. for 1 hour. After cooling to r.t. the mixture was partitioned between diethylether (2 ml) and saturated aq. sodium hydrogencarbonate (0.5 ml). The ether phase was isolated, dried over sodium sulphate and concentrated in vacuo. The residue was purified by flash chromatography (heptane→heptane/ethyl acetate 7:3), giving the title compound as a white solid.

Procedure b

A mixture of CuI (0.1 eq), 3,4,7,8-tetramethyl-1,10-phenanthroline (0.2 eq), heteroaryl halide (1.5 eq), caesium carbonate (1.5 eq), ingenol-5,20-acetonide (1 eq) and toluene was stirred in a closed vessel in an argon atmosphere at 80° C. until LC-MS of the crude reaction mixture showed that the ingenol-5,20-acetonide was consumed. The reaction mixture was
a) cooled to room temperature and filtered, toluene was removed in vacuo and the crude product was purified by HPLC (Eluent: acetonitrile/50 mM ammonium hydrogencarbonate 7:3→acetonitrile)
or
b) cooled to room temperature and diluted with EtOAc and water. The organic layer was washed twice with water. The organic layer was dried over MgSO4 and solvent removed in vacuo. The crude product was purified on flash chromatography (Silica gel) and eluted with 100% heptane→heptane/ethyl acetate 4:6.

Procedure c

A mixture of dry CsF (25-35 eq), heteroaryl chloride (3-5 eq) and dry DMSO was stirred in a closed vessel in an argon atmosphere at 130-140° C. and stirred until LC-MS of the crude reaction mixture indicated that approx. 50% of Cl was replaced with F. The reaction was cooled to room temperature and ingenol-5,20-acetonide was added. The reaction was stirred at room temperature until LC-MS of the crude reaction mixture showed that ingenol-5,20-acetonide was consumed.

The reaction mixture was diluted with diethylether and water. The organic layer was further washed three times with water. The organic layer was dried over sodium sulfate, filtered and solvent was removed in vacuo. The crude product was purified by flash chromatography as described in procedure b.

General Procedure for the Preparation of Compounds of General Formula I

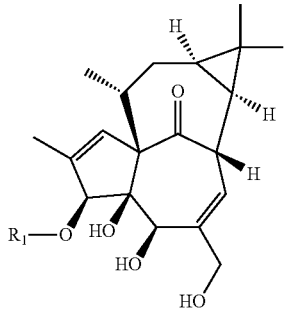

I

Procedure d

3-O-Heteroaryl-ingenol-5,20-acetonide (a compound of formula II) (0.10 mmol) was dissolved in tetrahydrofuran (0.47 mL) under argon. An aqueous solution of HCl (4 M, 4.7 μL) was added. The solution was stirred at room temperature for 20-27 h. Tetrahydrofuran may be replaced with methanol and the reaction time at room temperature shortened to 0.5 h. The solution was concentrated in vacuo. The residue was purified by flash chromatography (heptane/ethyl acetate 5:1→heptane/ethyl acetate 3:7), giving the title compound. For more polar compounds a dichloromethane/methanol 98:2→dichloromethane/methanol 95:5 gradient was used.

Procedure e

Preparation of 1-alkyl-2-iodo-imidazoles

2-Iodo-1H-imidazole (1.0 eq) was dissolved in dry DMF. Caesium carbonate (1.5 eq) and an alkyl halide (1.2 eq) was added, and the reaction was stirred at room temperature until 2-iodo-1H-imidazole was consumed. The mixture was diluted with diethylether and washed three times with water. The ether phase was dried over sodium sulphate and concentrated in vacuo. The product was used without further purification.

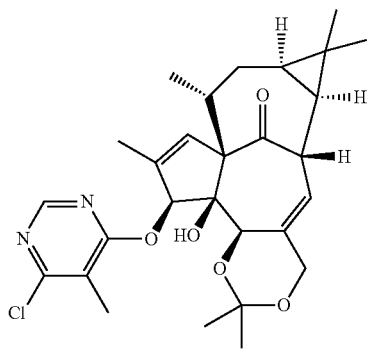 [SMILES: CC1=C[C@]23C(=O)[C@@H](C=C4COC(C)(C)O[C@H]4[C@]2(O)[C@H]1Oc1ncnc(Cl)c1C)[C@H]1[C@@H](C[C@H]3C)C1(C)C]

Preparation 201

3-O-(6-Chloro-5-methyl-pyrimidin-4-yl)-ingenol-5,20-acetonide (Compound 201)

Compound 201 was prepared according to Procedure a, but replacing DMF with acetonitrile at 100° C. for 18 h (sealed tube).

Starting material: 4,6-Dichloro-5-methyl-pyrimidine.

$^1$H NMR (300 MHz, CDCl$_3$) δ 8.34 (s, 1H), 6.14-6.12 (m, 1H), 5.97 (s, 1H), 5.81-5.78 (m, 1H), 4.27-4.11 (m, 3H), 4.06-4.04 (m, 1H), 3.60 (s, 1H), 2.67-2.62 (m, 1H), 2.29-2.20 (m, 4H), 1.82 (d, 3H), 1.82-1.72 (m, 1H), 1.46 (s, 3H), 1.45 (s, 3H), 1.07 (s, 3H), 1.04 (s, 3H), 1.03 (d, 3H), 0.95-0.85 (m, 1H), 0.74-0.66 (m, 1H).

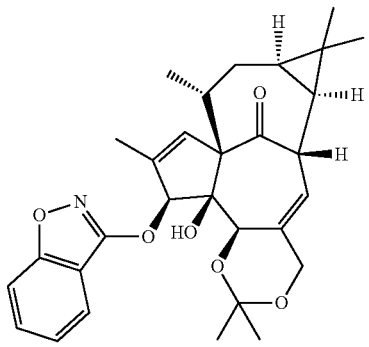 [SMILES: CC1=C[C@]23C(=O)[C@@H](C=C4COC(C)(C)O[C@H]4[C@]2(O)[C@H]1Oc1noc2ccccc12)[C@H]1[C@@H](C[C@H]3C)C1(C)C]

Preparation 202

3-O-(1,2-Benzoxazol-3-yl)-ingenol-5,20-acetonide (Compound 202)

Compound 202 was prepared according to Procedure c.

Starting material: 3-Chloro-1,2-benzoxazole.

$^1$H NMR (300 MHz, CDCl$_3$) δ 7.68-7.66 (m, 1H), 7.56-7.50 (m, 1H), 7.44-7.41 (m, 1H), 7.30-7.25 (m, 1H), 6.17-6.16 (m, 1H), 5.80-5.78 (m, 1H), 5.66 (s, 1H), 4.27-4.13 (m, 3H), 4.05-4.04 (m, 1H), 3.54 (s, 1H), 2.77-2.72 (m, 1H), 2.32-2.23 (m, 1H), 1.89 (d, 3H), 1.83-1.74 (m, 1H), 1.51 (s, 3H), 1.46 (s, 3H), 1.08-1.06 (m, 6H), 1.04 (s, 3H), 0.96-0.89 (m, 1H), 0.75-0.67 (m, 1H).

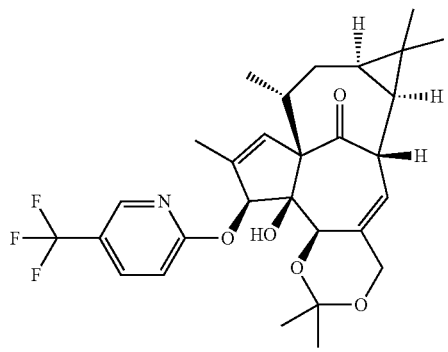 [SMILES: CC1=C[C@]23C(=O)[C@@H](C=C4COC(C)(C)O[C@H]4[C@]2(O)[C@H]1Oc1ccc(C(F)(F)F)cn1)[C@H]1[C@@H](C[C@H]3C)C1(C)C]

Preparation 203

3-O-(5-(Trifluoromethyl)-2-pyridyl)-ingenol-5,20-acetonide (Compound 203)

Compound 203 was prepared according to Procedure a, but replacing DMF with acetonitrile at 100° C. for 18 h (sealed tube).
Starting material: 2-Chloro-5-(trifluoromethyl)-pyridine.

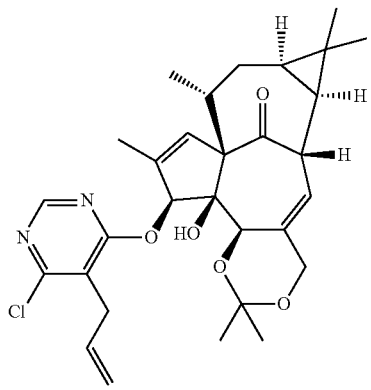 [SMILES: C=CCc1c(Cl)ncnc1O[C@H]1C(C)=C[C@]23C(=O)[C@@H](C=C4COC(C)(C)O[C@H]4[C@]12O)[C@H]1[C@@H](C[C@H]3C)C1(C)C]

Preparation 204

3-O-(5-Allyl-6-chloro-pyrimidin-4-yl)-ingenol-5,20-acetonide (Compound 204)

Compound 204 was prepared according to Procedure a.
Starting material: 5-Allyl-4,6-dichloro-pyrimidine.
$^1$H NMR (300 MHz, CDCl$_3$) δ 8.38 (s, 1H), 6.14-6.13 (m, 1H), 6.03 (s, 1H), 5.92-5.77 (m, 2H), 5.10-5.02 (m, 2H), 4.27-4.10 (m, 3H), 4.06 (t, 1H), 3.56 (s, 1H), 3.46 (dt, 2H), 2.67-2.61 (m, 1H), 2.28-2.19 (m, 1H), 1.80 (d, 3H), 1.79-1.70 (m, 1H), 1.47 (s, 3H), 1.45 (s, 3H), 1.07 (s, 3H), 1.05 (s, 3H), 1.02 (d, 3H), 0.94-0.86 (m, 1H), 0.74-0.66 (m, 1H).

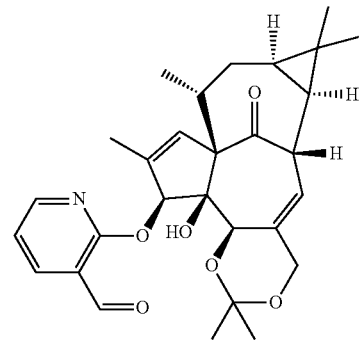 [SMILES: CC1=C[C@]23C(=O)[C@@H](C=C4COC(C)(C)O[C@H]4[C@]2(O)[C@H]1Oc1ncccc1C=O)[C@H]1[C@@H](C[C@H]3C)C1(C)C]

Preparation 205

3-O-(3-Formyl-2-pyridyl)-ingenol-5,20-acetonide (Compound 205)

Compound 205 was prepared according to Procedure a.
Starting material: 2-Chloropyridine-3-carbaldehyde.
$^1$H NMR (300 MHz, CDCl$_3$) δ 10.32 (s, 1H), 8.33 (dd, 1H), 8.13 (dd, 1H), 7.07 (dd, 1H), 6.14-6.13 (m, 1H), 6.01 (s, 1H), 5.80-5.77 (m, 1H), 4.42 (s, 1H), 4.22-4.15 (m, 3H), 4.05 (t, 1H), 2.69-2.65 (m, 1H), 2.34-2.25 (m, 1H), 1.87 (d, 3H), 1.84-1.78 (m, 1H), 1.43 (s, 6H), 1.09 (s, 3H), 1.05 (s, 3H), 1.03 (d, 3H), 0.95-0.86 (m, 1H), 0.75-0.67 (m, 1H).

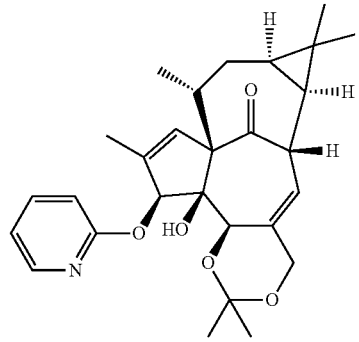 [SMILES: CC1=C[C@]23C(=O)[C@@H](C=C4COC(C)(C)O[C@H]4[C@]2(O)[C@H]1Oc1ccccn1)[C@H]1[C@@H](C[C@H]3C)C1(C)C]

Preparation 206

3-O-(2-Pyridyl)-ingenol-5,20-acetonide (Compound 206)

Compound 206 was prepared according to Procedure b.
Starting material: 2-Iodopyridine.
$^1$H NMR (300 MHz, CDCl$_3$) δ 8.11-8.08 (m, 1H), 7.64-7.58 (m, 1H), 6.94-6.90 (m, 1H), 6.84 (dt, 1H), 6.09-6.07 (m, 1H), 5.79-5.76 (m, 1H), 5.71 (s, 1H), 5.31 (s, 1H), 4.22-4.14 (m, 3H), 4.01 (s, 1H), 2.72-2.66 (m, 1H), 2.35-2.25 (m, 1H), 1.83 (d, 3H), 1.79-1.70 (m, 1H), 1.44 (s, 3H), 1.37 (s, 3H), 1.09 (s, 3H), 1.04 (s, 3H), 1.02 (d, 3H), 0.95-0.88 (m, 1H), 0.73-0.65 (m, 1H).

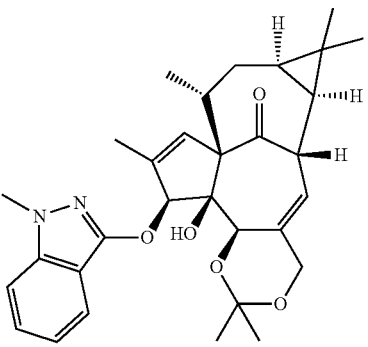

Preparation 207

3-O-(1-Methylindazol-3-yl)-ingenol-5,20-acetonide (Compound 207)

Compound 207 was prepared according to Procedure b.
Starting material: 3-Iodo-1-methyl-indazole.
$^1$H NMR (300 MHz, CDCl$_3$) δ 7.72-7.68 (m, 1H), 7.40-7.34 (m, 1H), 7.26-7.21 (m, 1H), 7.08-7.03 (m, 1H), 6.11-6.09 (m, 1H), 5.80-5.78 (m, 1H), 5.43 (s, 1H), 4.66 (s, 1H), 4.24-4.18 (m, 3H), 4.01-4.00 (m, 1H), 3.85 (s, 3H), 2.79-2.79 (m, 1H), 2.35-2.26 (m, 1H), 1.88 (d, 3H), 1.82-1.73 (m, 1H), 1.45 (s, 3H), 1.36 (s, 3H), 1.10 (s, 3H), 1.06 (d, 3H), 1.04 (s, 3H), 0.96-0.89 (m, 1H), 0.74-0.67 (m, 1H).

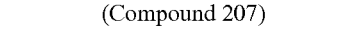

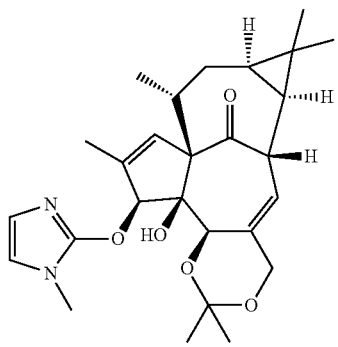 [SMILES: CC1=C[C@]23C(=O)[C@@H](C=C4COC(C)(C)O[C@H]4[C@]2(O)[C@H]1Oc1nccn1C)[C@H]1[C@@H](C[C@H]3C)C1(C)C]

Preparation 208

3-O-(1-Methylimidazol-2-yl)-ingenol-5,20-acetonide (Compound 208)

Compound 208 was prepared according to Procedure b.

Starting material: 2-Bromo-1-methyl-imidazole.

$^1$H NMR (300 MHz, CDCl$_3$) δ 6.55 (d, 1H), 6.48 (d, 1H), 6.16 (s, 1H), 6.12-6.11 (m, 1H), 5.76-5.73 (m, 1H), 5.35 (s, 1H), 4.25-4.13 (m, 3H), 3.92 (s, 1H), 3.43 (s, 3H), 2.69-2.64 (m, 1H), 2.40-2.31 (m, 1H), 1.86 (d, 3H), 1.78-1.69 (m, 1H), 1.41 (s, 3H), 1.33 (s, 3H), 1.10 (s, 3H), 1.04 (s, 3H), 1.01 (d, 3H), 0.94-0.87 (m, 1H), 0.72-0-67 (m, 1H).

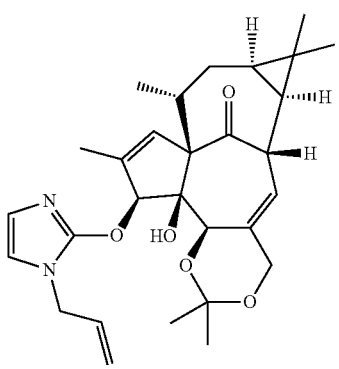 [SMILES: C=CCn1ccnc1O[C@H]1C(C)=C[C@]23C(=O)[C@@H](C=C4COC(C)(C)O[C@H]4[C@]12O)[C@H]1[C@@H](C[C@H]3C)C1(C)C]

Preparation 209

3-O-(1-Allylimidazol-2-yl)-ingenol-5,20-acetonide (Compound 209)

Compound 209 was prepared according to Procedure b.

Starting material: 1-Allyl-2-iodo-imidazole, prepared by procedure e with allyl bromide as starting material.

$^1$H NMR (300 MHz, CDCl$_3$) δ 6.58 (d, 1H), 6.50 (d, 1H), 6.11-6.09 (m, 1H), 6.02 (bs, 1H), 5.97-5.85 (m, 1H), 5.76-5.73 (m, 1H), 5.37 (s, 1H), 5.24-5.19 (m, 1H), 5.13-5.06 (m, 1H), 4.37-4.33 (m, 2H), 4.25-4.12 (m, 3H), 3.93-3.91 (m, 1H), 2.66-2.61 (m, 1H), 2.38-2.29 (m, 1H), 1.83 (d, 3H), 1.77-1.68 (m, 1H), 1.41 (s, 3H), 1.33 (s, 3H), 1.10 (s, 3H), 1.04 (s, 3H), 0.99 (d, 3H), 0.94-0.87 (m, 1H), 0.72-0.64 (m, 1H).

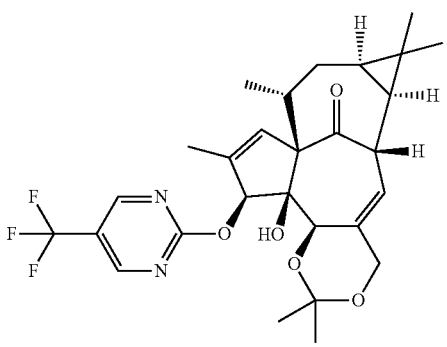 [SMILES: CC1=C[C@]23C(=O)[C@@H](C=C4COC(C)(C)O[C@H]4[C@]2(O)[C@H]1Oc1ncc(C(F)(F)F)cn1)[C@H]1[C@@H](C[C@H]3C)C1(C)C]

Preparation 210

3-O-(5-(Trifluoromethyl)-pyrimidin-2-yl)-ingenol-5,20-acetonide (Compound 210)

Compound 210 was prepared according to Procedure a.

Starting material: 2-Chloro-5-(trifluoromethyl)pyrimidine.

$^1$H NMR (300 MHz, CDCl$_3$) δ 8.74 (s, 2H), 6.17-6.16 (m, 1H), 5.98 (s, 1H), 5.82-5.79 (m, 1H), 4.27-4.13 (m, 3H), 4.09-4.08 (m, 1H), 3.44 (s, 1H), 2.77-2.72 (m, 1H), 2.29-2.20 (m, 1H), 1.8 (d, 3H), 1.83-1.74 (m, 1H), 1.48 (s, 3H), 1.46 (s, 3H), 1.05 (s, 3H), 1.04 (s, 3H), 1.03 (d, 3H), 0.94-0.87 (m, 1H), 0.74-0.66 (m, 1H).

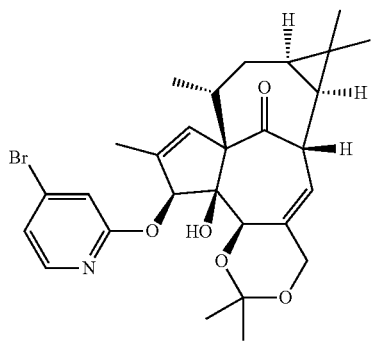 [SMILES: CC1=C[C@]23C(=O)[C@@H](C=C4COC(C)(C)O[C@H]4[C@]2(O)[C@H]1Oc1cc(Br)ccn1)[C@H]1[C@@H](C[C@H]3C)C1(C)C]

Preparation 211

3-O-(4-Bromo-2-pyridyl)-ingenol-5,20-acetonide (Compound 211)

Compound 211 was prepared according to Procedure a.

Starting material: 4-Bromo-2-fluoro-pyridine.

$^1$H NMR (300 MHz, CDCl$_3$) δ 7.92 (d, 1H), 7.08-7.05 (m, 2H), 7.53 (s, 1H), 6.09-6.08 (m, 1H), 5.79-5.77 (m, 1H), 5.74 (s, 1H), 4.20-4.12 (m, 3H), 4.02-4.01 (m, 1H), 2.69-2.63 (m, 1H), 2.31-2.22 (m, 1H), 1.82 (d, 3H), 1.80-1.71 (m, 1H), 1.45 (s, 3H), 1.40 (s, 3H), 1.08 (s, 3H), 1.04 (s, 3H), 1.02 (d, 3H), 0.95-0.89 (m, 1H), 0.73-0.65 (m, 1H).

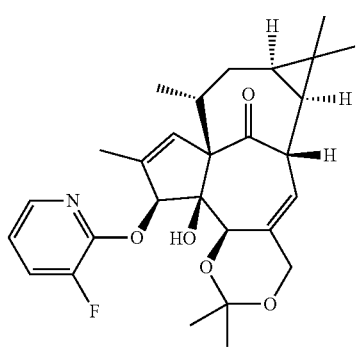 [SMILES: CC1=C[C@]23C(=O)[C@@H](C=C4COC(C)(C)O[C@H]4[C@]2(O)[C@H]1Oc1ncccc1F)[C@H]1[C@@H](C[C@H]3C)C1(C)C]

Preparation 212

3-O-(3-Fluoro-2-pyridyl)-ingenol-5,20-acetonide (Compound 212)

Compound 212 was prepared according to Procedure a.
Starting material: 2,3-Difluoro-pyridine.

$^1$H NMR (300 MHz, CDCl$_3$) δ 7.86 (dd, 1H), 7.40-7.33 (m, 1H), 6.93-6.88 (m, 1H), 6.11-6.10 (m, 1H), 5.81 (s, 1H), 5.79-5.76 (m, 1H), 4.60 (s, 1H), 4.21-4.14 (m, 3H), 4.03-4.02 (m, 1H), 2.74-2.69 (m, 1H), 2.32-2.23 (m, 1H), 1.85 (d, 3H), 1.82-1.73 (m, 1H), 1.43 (s, 3H), 1.39 (s, 3H), 1.09 (s, 3H), 1.04 (s, 3H), 1.03 (d, 3H), 0.96-0.89 (m, 1H), 0.74-0.66 (m, 1H).

Preparation 214

3-O-(4-(Trifluoromethyl)-pyrimidin-2-yl)-ingenol-5,20-acetonide (Compound 214)

Compound 214 was prepared according to Procedure a, but using 1.2 eq. of caesium carbonate at 40° C. for 4 h.
Starting material: 2-Chloro-4-(trifluoromethyl)-pyrimidine.

$^1$H NMR (300 MHz, CDCl$_3$) δ 8.77 (d, 1H), 7.29 (d, 1H), 6.17-6.15 (m, 1H), 5.99 (s, 1H), 5.80-5.77 (m, 1H), 4.22-4.12 (m, 3H), 4.09-4.08 (m, 1H), 3.40 (s, 1H), 2.80-2.73 (m, 1H), 2.29-2.20 (m, 1H), 1.84 (d, 3H), 1.83-1.74 (m, 1H), 1.45 (s, 3H), 1.44 (s, 3H), 1.06 (s, 3H), 1.04 (s, 3H), 1.03 (d, 3H), 0.94-0.85 (m, 1H), 0.74-0.66 (m, 1H).

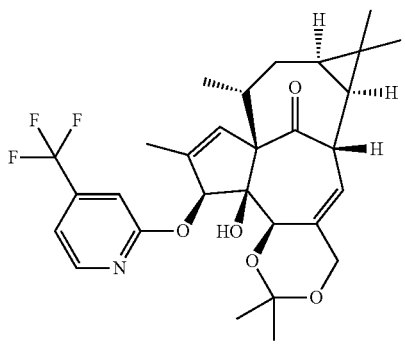 [SMILES: CC1=C[C@]23C(=O)[C@@H](C=C4COC(C)(C)O[C@H]4[C@]2(O)[C@H]1Oc1cc(C(F)(F)F)ccn1)[C@H]1[C@@H](C[C@H]3C)C1(C)C]

Preparation 213

3-O-(4-(Trifluoromethyl)-2-pyridyl)-ingenol-5,20-acetonide (Compound 213)

Compound 213 was prepared according to Procedure a.
Starting material: 2-Fluoro-4-(trifluoromethyl)-pyridine.

$^1$H NMR (300 MHz, CDCl$_3$) δ 8.24 (d, 1H), 7.12-7.10 (m, 1H), 7.06 (m, 1H), 6.12-6.10 (m, 1H), 5.86 (s, 1H), 5.80-5.77 (m, 1H), 4.22-4.13 (m, 4H), 4.06-4.05 (m, 1H), 2.70-2.65 (m, 1H), 2.31-2.22 (m, 1H), 1.83 (d, 3H), 1.82-1.73 (m, 1H), 1.46 (s, 3H), 1.42 (s, 3H), 1.08 (s, 3H), 1.04 (s, 3H), 1.03 (d, 3H), 0.95-0.86 (m, 1H), 0.74-0.66 (m, 1H).

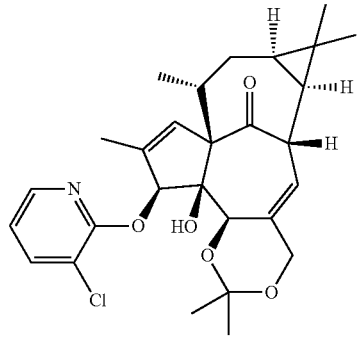 [SMILES: CC1=C[C@]23C(=O)[C@@H](C=C4COC(C)(C)O[C@H]4[C@]2(O)[C@H]1Oc1ncccc1Cl)[C@H]1[C@@H](C[C@H]3C)C1(C)C]

Preparation 215

3-O-(3-Chloro-2-pyridyl)-ingenol-5,20-acetonide (Compound 215)

Compound 215 was prepared according to Procedure a, but using 1.2 eq. of caesium carbonate at 40° C. for 5 h.
Starting material: 3-Chloro-2-fluoro-pyridine.

$^1$H NMR (300 MHz, CDCl$_3$) δ 7.99 (dd, 1H), 7.66 (dd, 1H), 6.89 (dd, 1H), 6.10-6.09 (m, 1H), 5.84 (s, 1H), 5.78-5.75 (m, 1H), 4.48 (s, 1H), 4.20-4.13 (m, 3H), 4.03-4.02 (m, 1H), 2.78-2.73 (m, 1H), 2.31-2.22 (m, 1H), 1.87 (d, 3H), 1.83-1.74 (m, 1H), 1.42 (s, 3H), 1.39 (s, 3H), 1.10 (s, 3H), 1.04 (s, 3H), 1.03 (d, 3H), 0.96-0.89 (m, 1H), 0.75-0.67 (m, 1H).

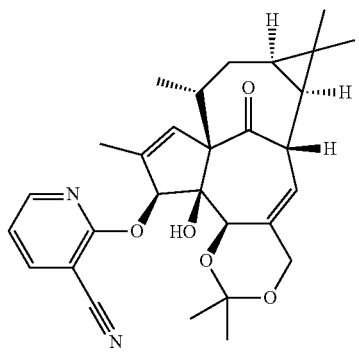 [SMILES: CC1=C[C@]23C(=O)[C@@H](C=C4COC(C)(C)O[C@H]4[C@]2(O)[C@H]1Oc1ncccc1C#N)[C@H]1[C@@H](C[C@H]3C)C1(C)C]

Preparation 216

3-O-(3-Cyano-2-pyridyl)-ingenol-5,20-acetonide (Compound 216)

Compound 216 was prepared according to Procedure a, but using 1.2 eq. of caesium carbonate at 40° C. for 16 h.

Starting material: 3-Cyano-2-fluoro-pyridine.

$^1$H NMR (300 MHz, CDCl$_3$) δ 8.29 (dd, 1H), 7.90 (dd, 1H), 7.01 (dd, 1H), 6.15-6.13 (m, 1H), 5.97 (s, 1H), 5.80-5.78 (m, 1H), 4.26-4.11 (m, 3H), 4.06-4.05 (m, 1H), 3.78 (s, 1H), 2.81-2.76 (m, 1H), 2.30-2.20 (m, 1H), 1.86 (d, 3H), 1.84-1.77 (m, 1H), 1.44 (s, 3H), 1.43 (s, 3H), 1.08 (s, 3H), 1.05 (d, 3H), 1.04 (s, 3H), 0.95-0.88 (m, 1H), 0.75-0.67 (m, 1H).

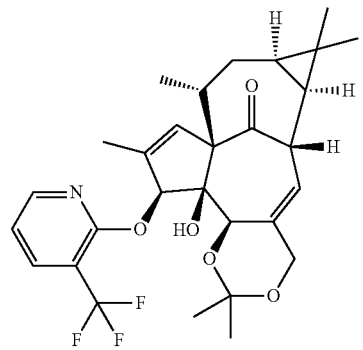

Preparation 218

3-O-(3-(Trifluoromethyl)-2-pyridyl)-ingenol-5,20-acetonide (Compound 218)

Compound 218 was prepared according to Procedure a, but using 1.2 eq. of caesium carbonate at 40° C. for 5 h.

Starting material: 2-Fluoro-3-(trifluoromethyl)-pyridine.

$^1$H NMR (300 MHz, CDCl$_3$) δ 8.25 (dd, 1H), 7.89 (dd, 1H), 7.01 (dd, 1H), 6.11-6.10 (m, 1H), 5.98 (s, 1H), 5.79-5.76 (m, 1H), 4.33 (s, 1H), 4.21-4.12 (m, 3H), 4.05 (t, 1H), 2.72-2.67 (m, 1H), 2.28-2.19 (m, 1H), 1.83 (d, 3H), 1.81-1.72 (m, 1H), 1.45 (s, 3H), 1.41 (s, 3H), 1.08 (s, 3H), 1.04 (s, 3H), 1.01 (d, 3H), 0.95-0.89 (m, 1H), 0.74-0.66 (m, 1H).

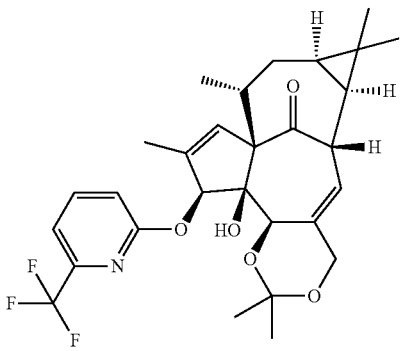 [SMILES: CC1=C[C@]23C(=O)[C@@H](C=C4COC(C)(C)O[C@H]4[C@]2(O)[C@H]1Oc1cccc(C(F)(F)F)n1)[C@H]1[C@@H](C[C@H]3C)C1(C)C]

Preparation 217

3-O-(6-(Trifluoromethyl)-2-pyridyl)-ingenol-5,20-acetonide (Compound 217)

Compound 217 was prepared according to Procedure a, but using 1.2 eq. of caesium carbonate at 40° C. for 16 h.

Starting material: 2-Fluoro-6-(trifluoromethyl)-pyridine.

$^1$H NMR (300 MHz, CDCl$_3$) δ 7.74 (t, 1H), 7.28 (d, 1H), 6.98 (d, 1H), 6.12-6.10 (m, 1H), 6.03 (s, 1H), 5.76-5.73 (m, 1H), 4.21-4.11 (m, 3H), 4.06 (t, 1H), 3.59 (s, 1H), 2.71-2.66 (m, 1H), 2.30-2.21 (m, 1H), 1.81 (d, 3H), 1.79-1.72 (m, 1H), 1.44 (s, 3H), 1.41 (s, 3H), 1.07 (s, 3H), 1.04 (s, 3H), 1.03 (d, 3H), 0.95-0.88 (m, 1H), 0.73-0.65 (m, 1H).

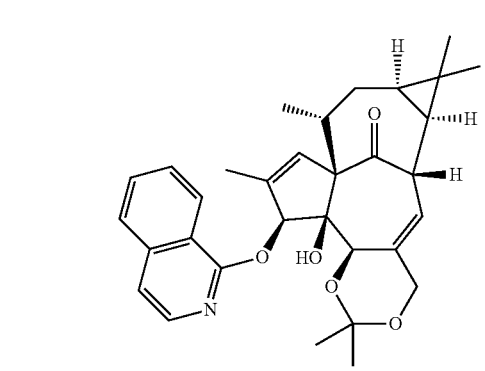 [SMILES: CC1=C[C@]23C(=O)[C@@H](C=C4COC(C)(C)O[C@H]4[C@]2(O)[C@H]1Oc1nccc2ccccc12)[C@H]1[C@@H](C[C@H]3C)C1(C)C]

Preparation 219

3-O-(1-Isoquinolyl)-ingenol-5,20-acetonide (Compound 219)

Compound 219 was prepared according to Procedure b.

Starting material: 1-Iodoisoquinoline.

$^1$H NMR (300 MHz, CDCl$_3$) δ 8.23 (d, 1H), 7.92 (d, 1H), 7.77-7.74 (m, 1H), 7.70-7.65 (m, 1H), 7.59-7.53 (m, 1H), 7.27-7.25 (m, 1H), 6.17-6.16 (m, 1H), 6.02 (s, 1H), 5.80-5.77 (m, 1H), 5.46 (s, 1H), 4.24-4.16 (m, 3H), 4.10-4.09 (m, 1H), 2.81-2.76 (m, 1H), 2.34-2.24 (m, 1H), 1.90 (d, 3H), 1.79-1.70 (m, 1H), 1.49 (s, 3H), 1.41 (s, 3H), 1.09 (d, 3H), 1.07 (s, 3H), 1.03 (s, 3H), 0.96-0.90 (m, 1H), 0.73-0.66 (m, 1H).

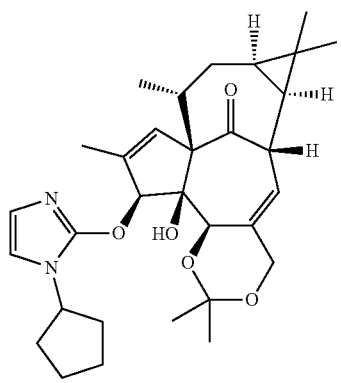 [SMILES: CC1=C[C@]23C(=O)[C@@H](C=C4COC(C)(C)O[C@H]4[C@]2(O)[C@H]1Oc1nccn1C1CCCC1)[C@H]1[C@@H](C[C@H]3C)C1(C)C]

Preparation 220

3-O-(1-Cyclopentylimidazol-2-yl)-ingenol-5,20-acetonide (Compound 220)

Compound 220 was prepared according to Procedure b.
Starting material: 1-Cyclopentyl-2-iodo-imidazole, prepared by procedure e with cyclopentyl iodide as starting material.
$^1$H NMR (300 MHz, CDCl$_3$) δ 6.55 (d, 1H), 6.54 (d, 1H), 6.13-6.11 (m, 1H), 5.76-5.73 (m, 1H), 5.38 (s, 1H), 4.46-4.41 (m, 1H), 4.26-4.11 (m, 3H), 3.93-3.92 (m, 1H), 2.68-2.63 (m, 1H), 2.40-2.31 (m, 1H), 2.12-2.03 (m, 2H), 1.85 (d, 3H), 1.83-1.65 (m, 7H), 1.42 (s, 3H), 1.33 (s, 3H), 1.09 (s, 3H), 1.04 (s, 3H), 1.01 (d, 3H), 0.94-0.87 (m, 1H), 0.72-0.64 (m, 1H).

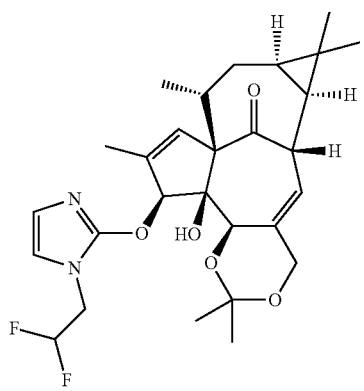 [SMILES: CC1=C[C@]23C(=O)[C@@H](C=C4COC(C)(C)O[C@H]4[C@]2(O)[C@H]1Oc1nccn1CC(F)F)[C@H]1[C@@H](C[C@H]3C)C1(C)C]

Preparation 221

3-O-(1-(2,2-Difluoroethyl)imidazol-2-yl)-ingenol-5,20-acetonide (Compound 221)

Compound 221 was prepared according to Procedure b.
Starting material: 1-(2,2-Difluoroethyl)-2-iodo-imidazole, prepared by procedure e with 2,2-difluoroethyl iodide as starting material.
$^1$H NMR (300 MHz, CDCl$_3$) δ 6.60 (d, 1H), 6.57 (d, 1H), 6.13-6.11 (m, 1H), 5.95 (tt, 1H), 5.77-5.75 (m, 1H), 5.46 (s, 1H), 5.26 (bs, 1H), 4.18-4.04 (m, 5H), 3.95-3.94 (m, 1H), 2.61-2.54 (m, 1H), 2.35-2.26 (m, 1H), 1.85 (d, 3H), 1.80-1.71 (m, 1H), 1.42 (s, 3H), 1.37 (s, 3H), 1.09 (s, 3H), 1.04 (s, 3H), 1.01 (d, 3H), 0.94-0.87 (m, 1H), 0.73-0.65 (m, 1H).

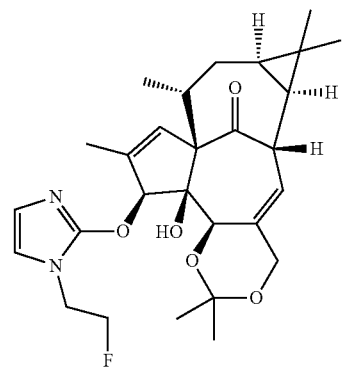 [SMILES: CC1=C[C@]23C(=O)[C@@H](C=C4COC(C)(C)O[C@H]4[C@]2(O)[C@H]1Oc1nccn1CCF)[C@H]1[C@@H](C[C@H]3C)C1(C)C]

Preparation 222

3-O-(1-(2-Fluoroethyl)imidazol-2-yl)-ingenol-5,20-acetonide (Compound 222)

Compound 222 was prepared according to Procedure b.
Starting material: 1-(2-Fluoroethyl)-2-iodo-imidazole, prepared by procedure e with 2-fluoroethyl iodide as starting material.
$^1$H NMR (300 MHz, CDCl$_3$) δ 6.59 (m, 2H), 6.12-6.10 (m, 1H), 5.76-5.74 (m, 2H), 5.43 (s, 1H), 4.62 (dt, 2H), 4.24-3.98 (m, 5H), 3.94-3.92 (m, 1H), 2.63-2.58 (m, 1H), 2.38-2.28 (m, 1H), 1.84 (d, 3H), 1.78-1.69 (m, 1H), 1.42 (s, 3H), 1.35 (s, 3H), 1.09 (s, 3H), 1.04 (s, 3H), 1.00 (d, 3H), 0.94-0.87 (m, 1H), 0.72-0.64 (m, 1H).

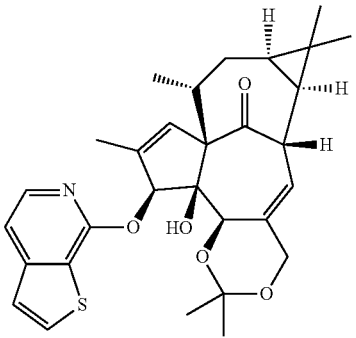 [SMILES: CC1=C[C@]23C(=O)[C@@H](C=C4COC(C)(C)O[C@H]4[C@]2(O)[C@H]1Oc1nccc2ccsc12)[C@H]1[C@@H](C[C@H]3C)C1(C)C]

Preparation 223

3-O-(Thieno[2,3-c]pyridine-7-yl)-ingenol-5,20-acetonide (Compound 223)

Compound 223 was prepared according to Procedure c.
Starting material: 7-Chlorothieno[2,3-c]pyridine.
$^1$H NMR (300 MHz, CDCl$_3$) δ 7.96 (d, 1H), 7.67 (d, 1H), 7.37-7.35 (d, 2H), 6.14-6.12 (m, 1H), 5.91 (s, 1H), 5.80-5.77 (m, 1H), 5.41 (s, 1H), 4.23-4.18 (m, 3H), 4.06-4.05 (m, 1H), 2.80-2.75 (m, 1H), 2.34-2.24 (m, 1H), 1.89 (d, 3H), 1.80-1.71 (m, 1H), 1.46 (s, 3H), 1.39 (s, 3H), 1.08 (s, 3H), 1.06 (d, 3H), 1.04 (s, 3H), 0.96-0.89 (m, 1H), 0.74-0.66 (m, 1H).

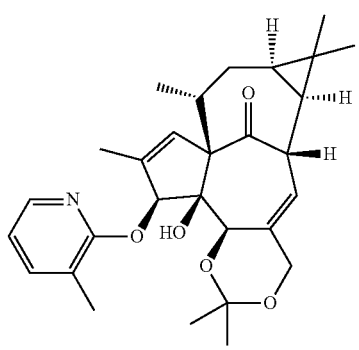 [SMILES: CC1=C[C@]23C(=O)[C@@H](C=C4COC(C)(C)O[C@H]4[C@]2(O)[C@H]1Oc1ncccc1C)[C@H]1[C@@H](C[C@H]3C)C1(C)C]

Preparation 224

3-O-(3-Methyl-2-pyridyl)-ingenol-5,20-acetonide (Compound 224)

Compound 224 was prepared according to Procedure b.
Starting material: 2-Bromo-3-methyl-pyridine.

$^1$H NMR (300 MHz, CDCl$_3$) δ 7.92 (dd, 1H), 7.45-7.42 (m, 1H), 6.84 (dd, 1H), 6.08-6.06 (m, 1H), 5.78-5.75 (m, 1H), 5.72 (bs, 1H), 5.70 (5.70 s, 1H), 4.22-4.14 (m, 3H), 4.01-4.00 (m, 1H), 2.74-2.68 (m, 1H), 2.34-2.25 (m, 1H), 2.21 (s, 3H), 1.85 (d, 3H), 1.79-1.70 (m, 1H), 1.43 (s, 3H), 1.36 (s, 3H), 1.10 (s, 3H), 1.04-1.01 (m, 6H), 0.96-0.89 (m, 1H), 0.73-0.65 (m, 1H).

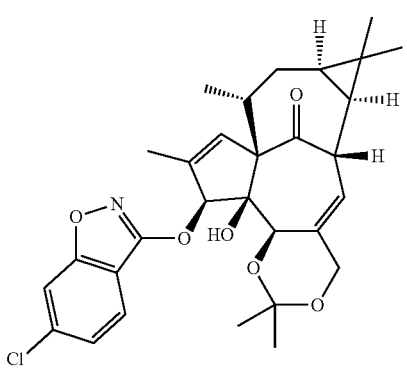 [SMILES: CC1=C[C@]23C(=O)[C@@H](C=C4COC(C)(C)O[C@H]4[C@]2(O)[C@H]1Oc1noc2cc(Cl)ccc12)[C@H]1[C@@H](C[C@H]3C)C1(C)C]

Preparation 225

3-O-(6-Chloro-1,2-benzoxazol-3-yl)-ingenol-5,20-acetonide (Compound 225)

Compound 225 was prepared according to Procedure c.
Starting material: 3,6-Dichloro-1,2-benzoxazole.

$^1$H NMR (300 MHz, CDCl$_3$) δ 7.58 (d, 1H), 7.45 (d, 1H), 7.26 (dd, 1H), 6.18-6.16 (m, 1H), 5.80-5.78 (m, 1H), 5.62 (s, 1H), 4.27-4.12 (m, 3H), 4.04-4.03 (m, 1H), 3.46 (s, 1H), 2.73-2.68 (m, 1H), 2.31-2.22 (m, 1H), 1.88 (d, 3H), 1.83-1.74 (m, 1H), 1.51 (s, 3H), 1.46 (s, 3H), 1.07-1.04 (m, 9H), 0.95-0.89 (m, 1H), 0.74-0.67 (m, 1H).

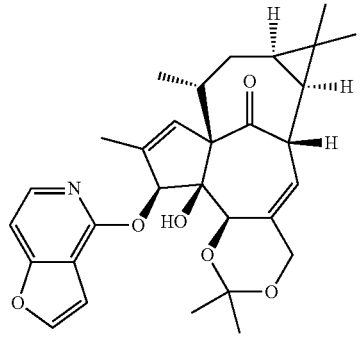 [SMILES: CC1=C[C@]23C(=O)[C@@H](C=C4COC(C)(C)O[C@H]4[C@]2(O)[C@H]1Oc1nccc2occc12)[C@H]1[C@@H](C[C@H]3C)C1(C)C]

Preparation 226

3-O-(Furo[3,2-c]pyridine-4-yl)-ingenol-5,20-acetonide (Compound 226)

Compound 226 was prepared according to Procedure c.
Starting material: 4-Chlorofuro[3,2-c]pyridine.

$^1$H NMR (300 MHz, CDCl$_3$) δ 7.93 (d, 1H), 7.59 (d, 1H), 7.14 (dd, 1H), 6.85 (dd, 1H), 6.13-6.11 (m, 1H), 5.87 (s, 1H), 5.79-5.77 (m, 1H), 5.54 (s, 1H), 4.22-4.15 (m, 3H), 4.05-4.04 (m, 1H), 2.76-2.70 (m, 1H), 2.34-2.25 (m, 1H), 1.86 (d, 3H), 1.79-1.70 (m, 1H), 1.46 (s, 3H), 1.38 (s, 3H), 1.08 (s, 3H), 1.06-1.04 (m, 6H), 0.96-0.89 (m, 1H), 0.73-0.65 (m, 1H).

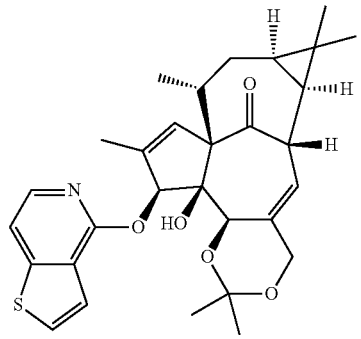 [SMILES: CC1=C[C@]23C(=O)[C@@H](C=C4COC(C)(C)O[C@H]4[C@]2(O)[C@H]1Oc1nccc2sccc12)[C@H]1[C@@H](C[C@H]3C)C1(C)C]

Preparation 227

3-O-(Thieno[3,2-c]pyridine-4-yl)-ingenol-5,20-acetonide (Compound 227)

Compound 227 was prepared according to Procedure c.
Starting material: 4-Chlorothieno[3,2-c]pyridine.

$^1$H NMR (300 MHz, CDCl$_3$) δ 7.91 (d, 1H), 7.51-7.40 (m, 3H), 6.13-6.12 (m, 1H), 5.93 (s, 1H), 5.79-5.77 (m, 1H), 5.45 (s, 1H), 4.23-4.16 (m, 3H), 4.07-4.05 (m, 1H), 2.78-2.72 (m, 1H), 2.33-2.24 (m, 1H), 1.87 (d, 3H), 1.79-1.70 (m, 1H), 1.46 (s, 3H), 1.39 (s, 3H), 1.08 (s, 3H), 1.06 (d, 3H), 1.04 (s, 3H), 0.99-0.89 (m, 1H), 0.73-0.66 (m, 1H).

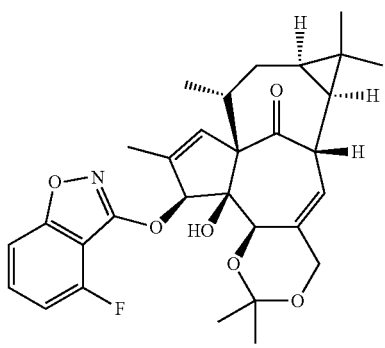 [SMILES: CC1=C[C@]23C(=O)[C@@H](C=C4COC(C)(C)O[C@H]4[C@]2(O)[C@H]1Oc1noc2cccc(F)c12)[C@H]1[C@@H](C[C@H]3C)C1(C)C]

Preparation 228

3-O-(4-Fluoro-1,2-benzoxazol-3-yl)-ingenol-5,20-acetonide (Compound 228)

Compound 228 was prepared according to Procedure c.

Starting material: 3-Chloro-4-fluoro-1,2-benzoxazole.

$^1$H NMR (300 MHz, CDCl$_3$) δ 7.47 (td, J=8.2, 5.0 Hz, 1H), 7.22 (d, J=9.1 Hz, 1H), 6.90 (dd, J=9.1, 8.1 Hz, 1H), 6.18-6.15 (m, 1H), 5.82-5.77 (m, 1H), 5.65 (s, 1H), 4.33-4.11 (m, 3H), 4.08-4.00 (m, 1H), 3.48 (s, 1H), 2.87-2.69 (m, 1H), 2.27 (ddd, J=15.8, 8.5, 3.1 Hz, 1H), 1.91 (d, J=1.6 Hz, 3H), 1.88-1.71 (m, 1H), 1.49 (s, 3H), 1.45 (s, 3H), 1.11-1.02 (m, 9H), 1.00-0.84 (m, 1H), 0.71 (td, J=8.4, 6.2 Hz, 1H).

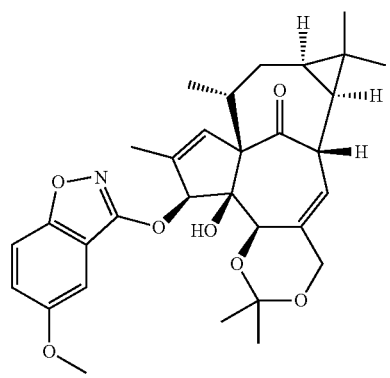

Preparation 230

3-O-(5-Methoxy-1,2-benzoxazol-3-yl)-ingenol-5,20-acetonide (compound 230)

Compound 230 was prepared according to Procedure c.

Starting material: 3-Chloro-5-methoxy-1,2-benzoxazole.

$^1$H NMR (300 MHz, CDCl$_3$) δ 7.32 (d, J=8.9 Hz, 1H), 7.15 (dd, J=9.1, 2.5 Hz, 1H), 6.98 (d, J=2.5 Hz, 1H), 6.19-6.15 (m, 1H), 5.81-5.76 (m, 1H), 5.64 (s, 1H), 4.31-4.12 (m, 3H), 4.04 (s, 1H), 3.87 (s, 3H), 3.59 (s, 1H), 2.80-2.67 (m, 1H), 2.29 (ddd, J=15.8, 8.9, 3.1 Hz, 1H), 1.89 (d, J=1.6 Hz, 3H), 1.79 (dt, J=15.8, 5.8 Hz, 1H), 1.51 (s, 3H), 1.45 (s, 3H), 1.08 (d, J=8.2 Hz, 3H), 1.07 (s, 3H), 1.04 (s, 3H), 1.00-0.84 (m, 1H), 0.71 (td, J=8.6, 6.2 Hz, 1H).

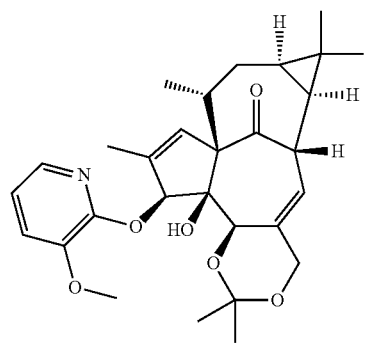 [SMILES: COc1cccnc1O[C@H]1C(C)=C[C@]23C(=O)[C@@H](C=C4COC(C)(C)O[C@H]4[C@]12O)[C@H]1[C@@H](C[C@H]3C)C1(C)C]

Preparation 229

3-O-(3-Methoxy-pyridin-2-yl)-ingenol-5,20-acetonide (Compound 229)

Compound 229 was prepared according to Procedure b.

Starting material: 2-Iodo-3-methoxy-pyridine.

$^1$H NMR (300 MHz, CDCl$_3$) δ 7.68 (dd, J=5.0, 1.5 Hz, 1H), 7.10 (dd, J=7.9, 1.6 Hz, 1H), 6.90 (dd, J=7.9, 5.0 Hz, 1H), 6.08 (q, J=1.5 Hz, 1H), 5.78-5.73 (m, 1H), 5.69 (s, 1H), 5.31 (s, 1H), 4.33-4.11 (m, 3H), 4.03-3.94 (m, 1H), 3.84 (s, 3H), 2.80-2.65 (m, 1H), 2.30 (ddd, J=15.7, 8.8, 3.3 Hz, 1H), 1.89 (d, J=1.5 Hz, 3H), 1.78 (dt, J=15.8, 5.9 Hz, 1H), 1.37 (s, 3H), 1.35 (s, 3H), 1.11 (s, 3H), 1.05 (s, 3H), 1.03 (d, J=8.2 Hz, 3H), 0.98-0.85 (m, 1H), 0.70 (td, J=8.5, 6.2 Hz, 1H).

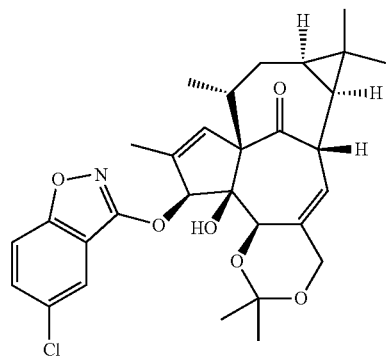 [SMILES: CC1=C[C@]23C(=O)[C@@H](C=C4COC(C)(C)O[C@H]4[C@]2(O)[C@H]1Oc1noc2ccc(Cl)cc12)[C@H]1[C@@H](C[C@H]3C)C1(C)C]

Preparation 231

3-O-(5-Chloro-1,2-benzoxazol-3-yl)-ingenol-5,20-acetonide (Compound 231)

Compound 231 was prepared according to Procedure c.

Starting material: 3,5-Dichloro-1,2-benzoxazole.

$^1$H NMR (300 MHz, CDCl$_3$) δ 7.64 (d, J=1.9 Hz, 1H), 7.48 (dd, J=9.0, 2.1 Hz, 1H), 7.36 (d, J=8.9 Hz, 1H), 6.20-6.15 (m, 1H), 5.83-5.75 (m, 1H), 5.62 (s, 1H), 4.30-4.09 (m, 3H), 4.04 (s, 1H), 3.47 (s, 1H), 2.80-2.65 (m, 1H), 2.27 (ddd, J=15.7, 8.9, 3.1 Hz, 1H), 1.88 (d, J=1.6 Hz, 3H), 1.80 (dt, J=15.8, 5.8 Hz, 1H), 1.51 (s, 3H), 1.46 (s, 3H), 1.10-1.02 (m, 9H), 0.98-0.82 (m, 1H), 0.71 (td, J=8.6, 6.2 Hz, 1H).

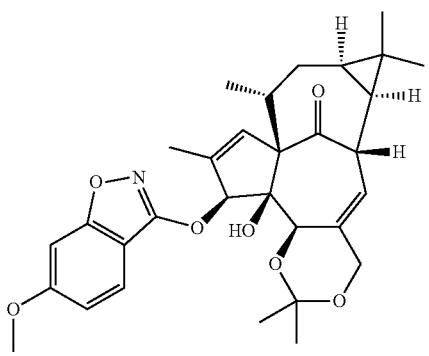 [SMILES: COc1ccc2c(O[C@H]3C(C)=C[C@]45C(=O)[C@@H](C=C6COC(C)(C)O[C@H]6[C@]34O)[C@H]3[C@@H](C[C@H]5C)C3(C)C)noc2c1]

Preparation 232

3-O-(6-Methoxy-1,2-benzoxazol-3-yl)-ingenol-5,20-acetonide (Compound 232)

Compound 232 was prepared according to Procedure c.
Starting material: 3-Chloro-6-methoxy-1,2-benzoxazole.

$^1$H NMR (300 MHz, CDCl$_3$) δ 7.55-7.44 (m, 1H), 6.96-6.81 (m, 2H), 6.15 (q, J=1.6 Hz, 1H), 5.80-5.75 (m, 1H), 5.61 (s, 1H), 4.30-4.11 (m, 3H), 4.05-4.00 (m, 1H), 3.87 (s, 3H), 3.57 (s, 1H), 2.80-2.65 (m, 1H), 2.27 (ddd, J=15.8, 8.7, 3.1 Hz, 1H), 1.88 (d, J=1.5 Hz, 3H), 1.78 (dt, J=15.8, 5.7 Hz, 1H), 1.51 (s, 3H), 1.45 (s, 3H), 1.10-1.00 (m, 9H), 1.00-0.84 (m, 1H), 0.70 (td, J=8.5, 6.2 Hz, 1H).

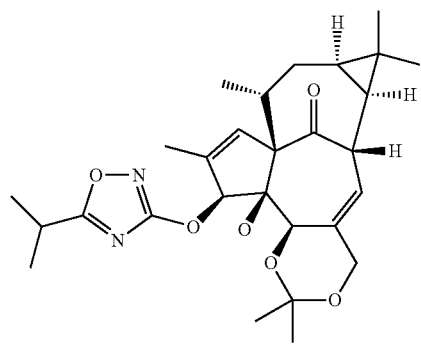 [SMILES: CC1=C[C@]23C(=O)[C@@H](C=C4COC(C)(C)O[C@H]4[C@]2(O)[C@H]1Oc1noc(C(C)C)n1)[C@H]1[C@@H](C[C@H]3C)C1(C)C]

Preparation 233

3-O-(5-Isopropyl-1,2,4-oxadiazol-3-yl)-ingenol-5,20-acetonide (Compound 233)

Compound 233 was prepared according to Procedure b.
Starting material: 3-chloro-5-isopropyl-1,2,4-oxadiazole $^1$H NMR (300 MHz, CDCl$_3$) δ 6.13 (q, J=1.7 Hz, 1H), 5.79 (m, 1H), 5.37 (s, 1H), 4.30-4.07 (m, 3H), 4.00 (bs, 1H), 3.47 (s, 1H), 3.17-3.00 (m, 1H), 2.78-2.63 (m, 1H), 2.26 (ddd, J=15.8, 9.2, 3.1 Hz, 1H), 1.86 (d, 3H), 1.85-1.70 (m, 1H), 1.47 (s, 3H), 1.43-1.34 (m, 9H), 1.07 (s, 3H), 1.05 (s, 3H), 0.99 (d, J=7.1 Hz, 3H), 0.95-0.83 (m, 1H), 0.76-0.64 (m, 1H).

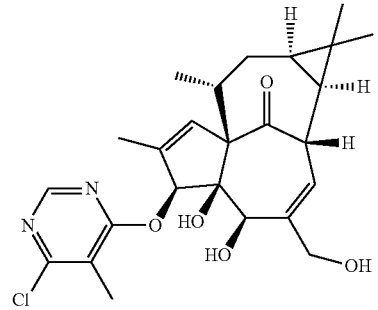 [SMILES: CC1=C[C@]23C(=O)[C@@H](C=C(CO)[C@@H](O)[C@]2(O)[C@H]1Oc1ncnc(Cl)c1C)[C@H]1[C@@H](C[C@H]3C)C1(C)C]

Example 101

3-O-(6-Chloro-5-methyl-pyrimidin-4-yl)-ingenol (Compound 101)

Compound 101 was prepared according to Procedure d.
Starting material: Compound 201.

$^1$H NMR (300 MHz, CDCl$_3$) δ 8.40 (s, 1H), 6.12-6.10 (m, 1H), 6.08-6.06 (m, 1H), 5.77 (s, 1H), 4.9 (bs, 1H), 4.16-4.06 (m, 4H), 3.67 (bs, 1H), 2.61-2.56 (m, 1H), 2.28 (s, 3H), 2.26-2.19 (m, 1H), 2.0 (bs, 1H), 1.83 (d, 3H), 1.80-1.73 (m, 1H), 1.07 (s, 3H), 1.05 (s, 3H), 1.01 (d, 3H), 0.99-0.92 (m, 1H), 0.74-0.67 (m, 1H).

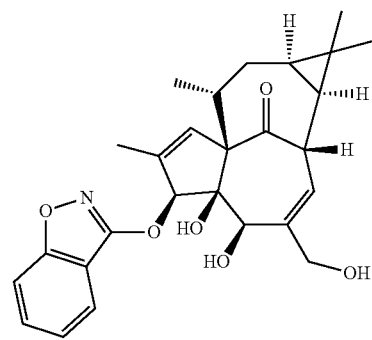 [SMILES: CC1=C[C@]23C(=O)[C@@H](C=C(CO)[C@@H](O)[C@]2(O)[C@H]1Oc1noc2ccccc12)[C@H]1[C@@H](C[C@H]3C)C1(C)C]

Example 102

3-O-(1,2-Benzoxazol-3-yl)-ingenol (Compound 102)

Compound 102 was prepared according to Procedure d.
Starting material: Compound 202.

$^1$H NMR (300 MHz, CDCl$_3$) δ 7.71-7.68 (m, 1H), 7.60-7.54 (m, 1H), 7.47-7.44 (m, 1H), 7.33-7.28 (m, 1H), 7.18-7.16 (m, 1H), 6.08-6.06 (m, 1H), 5.63 (s, 1H), 4.42 (d, 1H), 4.19-4.10 (m, 4H), 3.77 (s, 1H), 2.68-2.61 (m, 1H), 2.33-2.24 (m, 2H), 1.90 (d, 3H), 1.84-1.75 (m, 1H), 1.07-1.05 (m, 9H), 0.99-0.92 (m, 1H), 0.75-0.67 (m, 1H).

Example 103

3-O-(5-(Trifluoromethyl)-2-pyridyl)-ingenol (Compound 103)

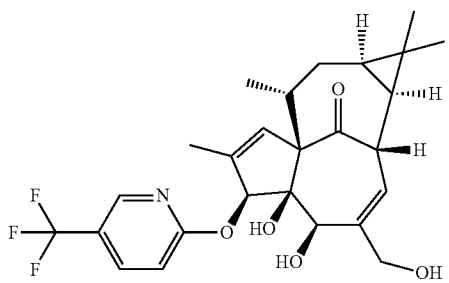 [SMILES: CC1=C[C@]23C(=O)[C@@H](C=C(CO)[C@@H](O)[C@]2(O)[C@H]1Oc1ccc(C(F)(F)F)cn1)[C@H]1[C@@H](C[C@H]3C)C1(C)C]

Compound 103 was prepared according to Procedure d.
Starting material: Compound 203.

$^1$H NMR (300 MHz, CDCl$_3$) δ 8.41-8.40 (m, 1H), 7.87 (dd, 1H), 7.97 (d, 1H), 6.10-6.06 (m, 2H), 5.75 (s, 1H), 4.86 (bs, 1H), 4.16-4.06 (m, 4H), 3.75 (s, 1H), 2.61-2.56 (m, 1H), 2.45 (bs, 1H), 2.29-2.20 (m, 1H), 1.83 (d, 3H), 1.81-1.73 (m, 1H), 1.07 (s, 3H), 1.05 (s, 3H), 1.01 (d, 3H), 0.98-0.93 (m, 1H), 0.74-0.66 (m, 1H).

Example 104

3-O-(5-Allyl-6-chloro-pyrimidin-4-yl)-ingenol (Compound 104)

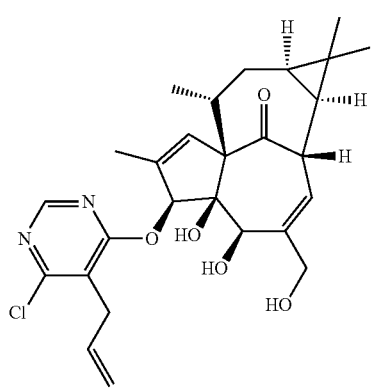 [SMILES: C=CCc1c(Cl)ncnc1O[C@H]1C(C)=C[C@]23C(=O)[C@@H](C=C(CO)[C@@H](O)[C@]12O)[C@H]1[C@@H](C[C@H]3C)C1(C)C]

Compound 104 was prepared according to Procedure d.
Starting material: Compound 204.

$^1$H NMR (300 MHz, CDCl$_3$) δ 8.44 (s, 1H), 6.12-6.10 (m, 1H), 6.07-6.04 (m, 1H), 5.91-5.81 (m, 2H), 5.13-5.02 (m, 2H), 4.6 (bs, 1H), 4.20-4.06 (m, 4H), 3.69 (bs, 1H), 3.51-3.46 (m, 2H), 2.59-2.54 (m, 1H), 2.5 (bs, 1H), 2.27-2.18 (m, 1H), 1.81-1.72 (m, 4H), 1.06 (s, 3H), 1.05 (s, 3H), 1.01 (d, 3H), 0.98-0.91 (m, 1H), 0.74-0.66 (m, 1H).

Example 105

3-O-(3-Formyl-2-pyridyl)-ingenol (Compound 105)

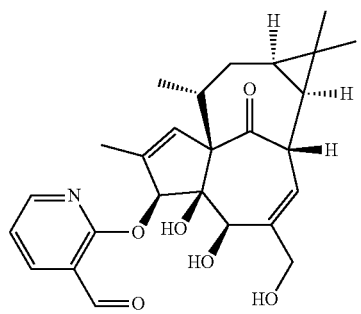 [SMILES: CC1=C[C@]23C(=O)[C@@H](C=C(CO)[C@@H](O)[C@]2(O)[C@H]1Oc1ncccc1C=O)[C@H]1[C@@H](C[C@H]3C)C1(C)C]

Compound 105 was prepared according to Procedure d.
Starting material: Compound 205.

$^1$H NMR (300 MHz, CDCl$_3$) δ 10.27 (s, 1H), 8.35 (dd, 1H), 8.16 (dd, 1H), 7.13 (dd, 1H), 6.13-6.11 (m, 1H), 6.08-6.06 (m, 1H), 5.85 (s, 1H), 4.49 (d, 1H), 4.45 (s, 1H), 4.17-4.09 (m, 4H), 2.65-2.60 (m, 1H), 2.38-2.27 (m, 2H), 1.89 (d, 3H), 1.87-1.78 (m, 1H), 1.10 (s, 3H), 1.06 (s, 3H), 1.01 (d, 3H), 1.00-0.94 (m, 1H), 0.76-0.69 (m, 1H).

Example 106

3-O-(2-Pyridyl)-ingenol (Compound 106)

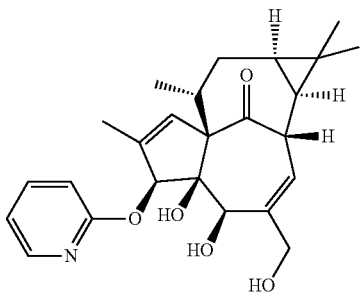 [SMILES: CC1=C[C@]23C(=O)[C@@H](C=C(CO)[C@@H](O)[C@]2(O)[C@H]1Oc1ccccn1)[C@H]1[C@@H](C[C@H]3C)C1(C)C]

Compound 106 was prepared according to Procedure d.
Starting material: Compound 206.

$^1$H NMR (300 MHz, CDCl$_3$) δ 8.08 (d, 1H), 7.71-7.65 (m, 1H), 6.99-6.95 (m, 1H), 6.90 (d, 1H), 6.06-6.05 (m, 2H), 5.53 (s, 1H), 5.0 (bs, 2H), 4.15-4.07 (m, 4H), 2.63-2.56 (m, 1H), 2.6 (bs, 1H), 2.29-2.20 (m, 1H), 1.84-1.73 (m, 4H), 1.08 (s, 3H), 1.04 (s, 3H), 1.02-0.94 (m, 4H), 0.74-0.66 (m, 1H).

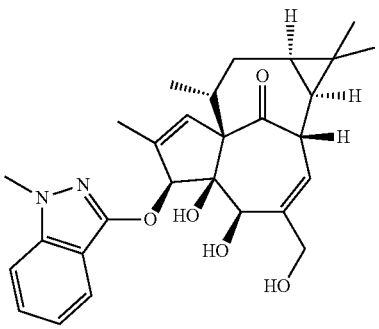

Example 107

3-O-(1-Methylindazol-3-yl)-ingenol (Compound 107)

Compound 107 was prepared according to Procedure d.
Starting material: Compound 207.
$^1$H NMR (300 MHz, CDCl$_3$) δ 7.69 (d, 1H), 7.43-7.38 (m, 1H), 7.24 (d, 1H), 7.09 (t, 1H), 6.10-6.07 (m, 2H), 5.42 (s, 1H), 4.17-4.08 (m, 4H), 4.2-2.8 (bs, 3H), 3.86 (s, 3H), 2.66-2.61 (m, 1H), 2.33.2.24 (m, 1H), 1.89 (d, 3H), 1.84-1.75 (m, 1H), 1.09 (s, 3H), 1.05 (s, 3H), 1.05 (d, 3H), 1.01-0.94 (m, 1H), 0.75-0.68 (m, 1H).

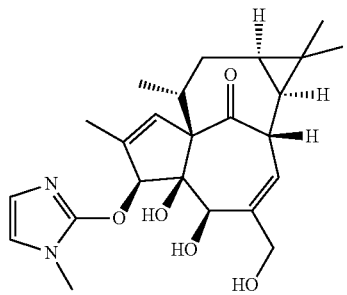 [SMILES: CC1=C[C@]23C(=O)[C@@H](C=C(CO)[C@@H](O)[C@]2(O)[C@H]1Oc1nccn1C)[C@H]1[C@@H](C[C@H]3C)C1(C)C]

Example 108

3-O-(1-Methylimidazol-2-yl)-ingenol (Compound 108)

Compound 108 was prepared according to Procedure d.
Starting material: Compound 208.
$^1$H NMR (300 MHz, CDCl$_3$) δ 6.53 (d, 1H), 6.50 (d, 1H), 6.4 (bs, 1H), 6.07-6.06 (m, 1H), 6.04-6.02 (m, 1H), 5.16 (s, 1H), 4.6 (bs, 1H), 4.17-4.05 (m, 4H), 3.44 (s, 3H), 3.0 (bs, 1H), 2.62-2.56 (m, 1H), 2.31-2.22 (m, 1H), 1.85 (d, 3H), 1.81-1.72 (m, 1H), 1.09 (s, 3H), 1.04 (s, 3H), 1.00-0.92 (m, 4H), 0.73-0.65 (m, 1H).

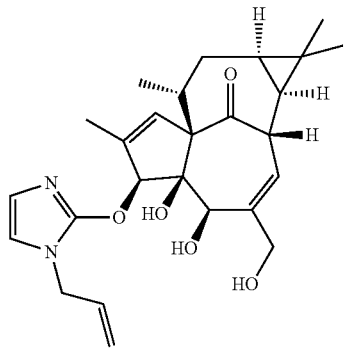 [SMILES: C=CCn1ccnc1O[C@H]1C(C)=C[C@]23C(=O)[C@@H](C=C(CO)[C@@H](O)[C@]12O)[C@H]1[C@@H](C[C@H]3C)C1(C)C]

Example 109

3-O-(1-Allylimidazol-2-yl)-ingenol (Compound 109)

Compound 109 was prepared according to Procedure d.
Starting material: Compound 209.
$^1$H NMR (300 MHz, CDCl$_3$) δ 6.56 (d, 1H), 6.51 (d, 1H), 6.06-6.02 (m, 2H), 5.96-5.84 (m, 1H), 5.26-5.21 (m, 1H), 5.19 (s, 1H), 5.16-5.08 (m, 1H), 4.7 (bs, 1H), 4.43-4.29 (m, 2H), 4.17-4.05 (m, 4H), 2.9 (bs, 1H), 2.60-2.54 (m, 1H), 2.30-2.21 (m, 1H), (2.00 (s, 1H), 1.82 (d, 3H), 1.80-1.70 (m, 1H), 1.09 (s, 3H), 1.04 (s, 3H), 1.00-0.94 (m, 4H), 0.72-0.65 (m, 1H).

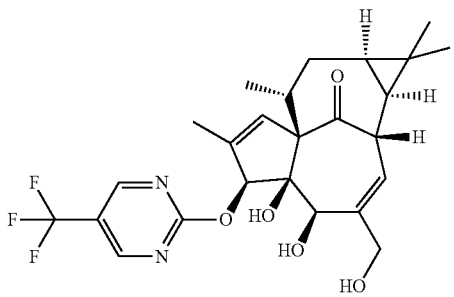 [SMILES: CC1=C[C@]23C(=O)[C@@H](C=C(CO)[C@@H](O)[C@]2(O)[C@H]1Oc1ncc(C(F)(F)F)cn1)[C@H]1[C@@H](C[C@H]3C)C1(C)C]

Example 110

3-O-(5-(Trifluoromethyl)-pyrimidin-2-yl)-ingenol (Compound 110)

Compound 110 was prepared according to Procedure d.
Starting material: Compound 210.
$^1$H NMR (300 MHz, CDCl$_3$) δ 8.78 (s, 2H), 6.15-6.13 (m, 1H), 6.09-6.07 (m, 1H), 5.98 (s, 1H), 4.19-4.07 (m, 5H), 3.82 (s, 1H), 2.69-2.64 (m, 1H), 2.38 (t, 1H), 2.30-2.20 (m, 1H), 1.85 (d, 3H), 1.83-1.76 (m, 1H), 1.06 (s, 3H), 1.06 (s, 3H), 1.02 (d, 3H), 0.98-0.90 (m, 1H), 0.75-0.67 (m, 1H).

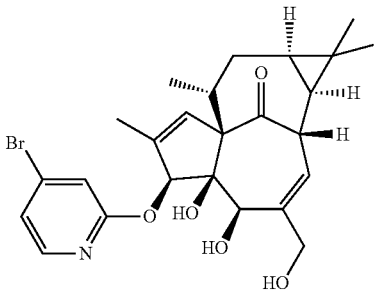 [SMILES: CC1=C[C@]23C(=O)[C@@H](C=C(CO)[C@@H](O)[C@]2(O)[C@H]1Oc1cc(Br)ccn1)[C@H]1[C@@H](C[C@H]3C)C1(C)C]

Example 111

3-O-(4-Bromo-2-pyridyl)-ingenol (Compound 111)

Compound 111 was prepared according to Procedure d.
Starting material: Compound 211.
$^1$H NMR (300 MHz, CDCl$_3$) δ 7.92-7.90 (m, 1H), 7.13-7.10 (m, 2H), 6.07-6.05 (m, 2H), 5.58 (s, 1H), 5.15 (bs, 1H), 4.15-4.05 (m, 4H), 3.86 (s, 1H), 2.60-2.50 (m, 2H), 2.28-2.19 (m, 1H), 1.82-1.73 (m, 4H), 1.07 (s, 3H), 1.04 (s, 3H), 1.01-0.96 (m, 4H), 0.74-0.66 (m, 1H).

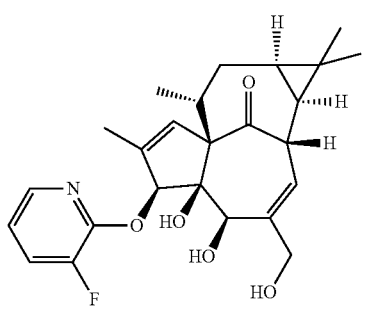 [SMILES: CC1=C[C@]23C(=O)[C@@H](C=C(CO)[C@@H](O)[C@]2(O)[C@H]1Oc1ncccc1F)[C@H]1[C@@H](C[C@H]3C)C1(C)C]

Example 112

3-O-(3-Fluoro-2-pyridyl)-ingenol (Compound 112)

Compound 112 was prepared according to Procedure d. Starting material: Compound 212.
$^1$H NMR (300 MHz, CDCl$_3$) δ 7.88 (dd, 1H), 7.45-7.39 (m, 1H), 6.98-6.93 (m, 1H), 6.09-6.06 (m, 2H), 5.69 (s, 1H), 4.71 (d, 1H), 4.16-4.07 (m, 4H), 4.03 (s, 1H), 2.64-2.59 (m, 1H), 2.46 (t, 1H), 2.30-2.21 (m, 1H), 1.86 (d, 3H), 1.84-1.75 (m, 1H), 1.09 (s, 3H), 1.05 (s, 3H), 1.02 (d, 3H), 1.01-0.94 (m, 1H), 0.75-0.67 (m, 1H).

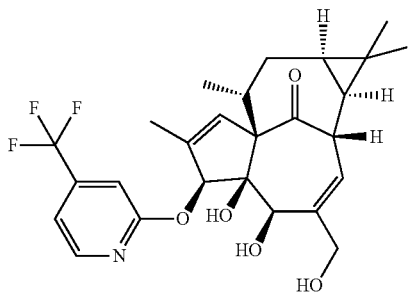 [SMILES: CC1=C[C@]23C(=O)[C@@H](C=C(CO)[C@@H](O)[C@]2(O)[C@H]1Oc1cc(C(F)(F)F)ccn1)[C@H]1[C@@H](C[C@H]3C)C1(C)C]

Example 113

3-O-(4-(Trifluoromethyl)-2-pyridyl)-ingenol (Compound 113)

Compound 113 was prepared according to Procedure d. Starting material: Compound 213.
$^1$H NMR (300 MHz, CDCl$_3$) δ 8.26 (d, 1H), 7.17-7.15 (m, 1H), 7.13-7.12 (m, 1H), 6.09-6.06 (m, 2H), 5.71 (s, 1H), 4.91 (d, 1H), 4.17-4.06 (m, 4H), 3.79 (s, 1H), 2.62-2.57 (m, 1H), 2.48 (t, 1H), 2.29-2.20 (m, 1H), 1.83 (d, 3H), 1.82-1.74 (m, 1H), 1.07 (s, 3H), 1.05 (s, 3H), 1.01 (d, 3H), 1.00-0.93 (m, 1H), 0.75 (m, 1H).

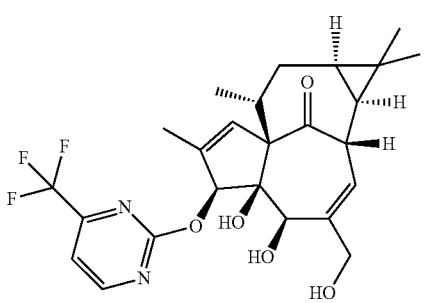 [SMILES: CC1=C[C@]23C(=O)[C@@H](C=C(CO)[C@@H](O)[C@]2(O)[C@H]1Oc1nccc(C(F)(F)F)n1)[C@H]1[C@@H](C[C@H]3C)C1(C)C]

Example 114

3-O-(4-(Trifluoromethyl)-pyrimidin-2-yl)-ingenol (Compound 114)

Compound 114 was prepared according to Procedure d. Starting material: Compound 214.
$^1$H NMR (300 MHz, CDCl$_3$) δ 8.79 (d, 2H), 7.34 (d, 1H), 6.15-6.13 (m, 1H), 6.09-6.06 (m, 1H), 5.91 (s, 1H), 4.18-4.07 (m, 4H), 3.97-3.95 (d, 1H), 3.80 (s, 1H), 2.69-2.64 (m, 1H), 2.33-2.21 (m, 2H), 1.86 (d, 3H), 1.83-1.76 (m, 1H), 1.07 (s, 3H), 1.06 (s, 3H), 1.02 (d, 3H), 0.98-0.91 (m, 1H), 0.76-0.68 (m, 1H).

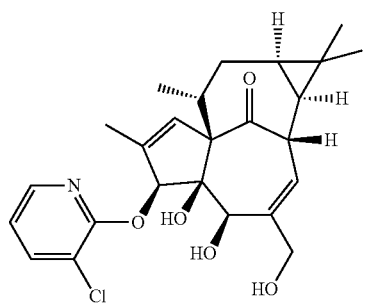 [SMILES: CC1=C[C@]23C(=O)[C@@H](C=C(CO)[C@@H](O)[C@]2(O)[C@H]1Oc1ncccc1Cl)[C@H]1[C@@H](C[C@H]3C)C1(C)C]

Example 115

3-O-(3-Chloro-2-pyridyl)-ingenol (Compound 115)

Compound 115 was prepared according to Procedure d. Starting material: Compound 215.
$^1$H NMR (300 MHz, CDCl$_3$) δ 8.02 (dd, 1H), 7.71 (dd, 1H), 6.94 (dd, 1H), 6.08-6.06 (m, 2H), 5.75 (s, 1H), 4.47 (d, 1H), 4.16-4.07 (m, 4H), 3.97 (s, 1H), 2.68-2.62 (m, 1H), 2.40 (t, 1H), 2.29-2.20 (m, 1H), 1.87 (d, 3H), 1.86-1.76 (m, 1H), 1.10 (s, 3H), 1.05 (s, 3H), 1.02 (d, 3H), 1.01-0.95 (m, 1H), 0.76-0.68 (m, 1H).

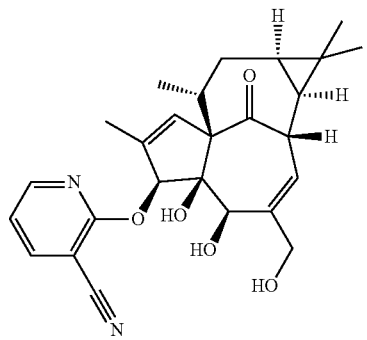 [SMILES: CC1=C[C@]23C(=O)[C@@H](C=C(CO)[C@@H](O)[C@]2(O)[C@H]1Oc1ncccc1C#N)[C@H]1[C@@H](C[C@H]3C)C1(C)C]

Example 116

3-O-(3-Cyano-2-pyridyl)-ingenol (Compound 116)

Compound 116 was prepared according to Procedure d. Starting material: Compound 216.
$^1$H NMR (300 MHz, CDCl$_3$) δ 8.33 (dd, 1H), 7.95 (dd, 1H), 7.07 (dd, 1H), 6.13-6.12 (m, 1H), 6.08 (d, 1H), 5.90 (s, 1H), 4.4 (bs, 1H), 4.17-4.09 (m, 4H), 3.74 (s, 1H), 2.71-2.66 (m, 1H), 2.29-2.20 (m, 1H), 2.0 (bs, 1H), 1.88-1.78 (m, 4H), 1.08 (s, 3H), 1.05 (s, 3H), 1.04 (d, 3H), 0.99-0.91 (m, 1H), 0.76-0.68 (m, 1H).

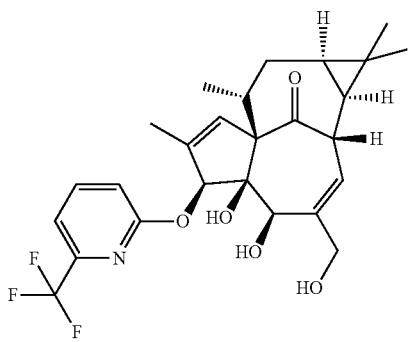 [SMILES: CC1=C[C@]23C(=O)[C@@H](C=C(CO)[C@@H](O)[C@]2(O)[C@H]1Oc1cccc(C(F)(F)F)n1)[C@H]1[C@@H](C[C@H]3C)C1(C)C]

Example 117

3-O-(6-(Trifluoromethyl)-2-pyridyl)-ingenol (Compound 117)

Compound 117 was prepared according to Procedure d.
Starting material: Compound 217.
¹H NMR (300 MHz, CDCl₃) δ 7.80 (t, 1H), 7.33 (d, 1H), 7.05 (d, 1H), 6.11-6.09 (m, 1H), 6.08-6.06 (m, 1H), 5.72 (s, 1H), 4.21-4.08 (m, 5H), 3.80 (s, 1H), 2.62-2.57 (m, 1H), 2.43 (t, 1H), 2.31-2.21 (m, 1H), 1.84 (d, 3H), 1.82-1.73 (m, 1H), 1.07 (s, 3H), 1.05 (s, 3H), 1.02 (d, 3H), 0.99-0.93 (m, 1H), 0.74-0.66 (m, 1H).

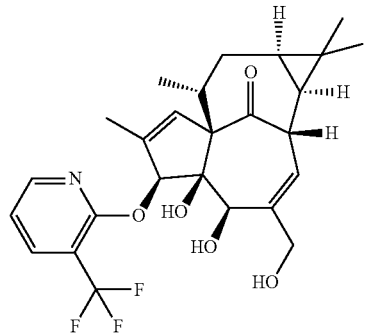 [SMILES: CC1=C[C@]23C(=O)[C@@H](C=C(CO)[C@@H](O)[C@]2(O)[C@H]1Oc1ncccc1C(F)(F)F)[C@H]1[C@@H](C[C@H]3C)C1(C)C]

Example 118

3-O-(3-(Trifluoromethyl)-2-pyridyl)-ingenol (Compound 118)

Compound 118 was prepared according to Procedure d.
Starting material: Compound 218.
¹H NMR (300 MHz, CDCl₃) δ 8.29 (dd, 1H), 7.94 (dd, 1H), 7.06 (dd, 1H), 6.09-6.06 (m, 2H), 5.93 (s, 1H), 4.40 (bs, 1H), 4.16 (s, 2H), 4.12-4.07 (m, 2H), 3.84 (s, 1H), 2.63-2.58 (m, 1H), 2.43 (bs, 1H), 2.27-2.18 (m, 1H), 1.84 (d, 3H), 1.84-1.75 (m, 1H), 1.09 (s, 3H), 1.05 (s, 3H), 1.00 (d, 3H), 0.98-0.90 (m, 1H), 0.75-0.68 (m, 1H).

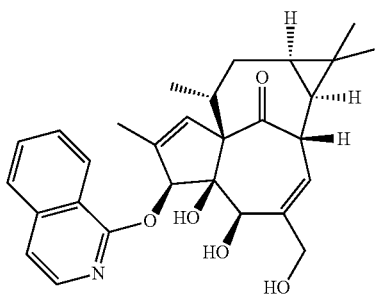 [SMILES: CC1=C[C@]23C(=O)[C@@H](C=C(CO)[C@@H](O)[C@]2(O)[C@H]1Oc1nccc2ccccc12)[C@H]1[C@@H](C[C@H]3C)C1(C)C]

Example 119

3-O-(1-Isoquinolyl)-ingenol (Compound 119)

Compound 119 was prepared according to Procedure d.
Starting material: Compound 219.
¹H NMR (300 MHz, CDCl₃) δ 8.30-8.27 (m, 1H), 7.87 (d, 1H), 7.80-7.70 (m, 2H), 7.63-7.57 (m, 1H), 7.31-7.29 (m, 1H), 6.28 (bs, 1H), 6.12-6.10 (m, 1H), 6.08-6.06 (m, 1H), 5.72 (s, 1H), 4.26-4.05 (m, 4H), 3.93 (bs, 1H), 2.76-2.65 (m, 2H), 2.25-2.16 (m, 1H), 1.89 (d, 3H), 1.82-1.73 (m, 1H), 1.06 (s, 3H), 1.05 (d, 3H), 1.03 (s, 3H), 1.03-0.96 (m, 1H), 0.74-0.66 (m, 1H).

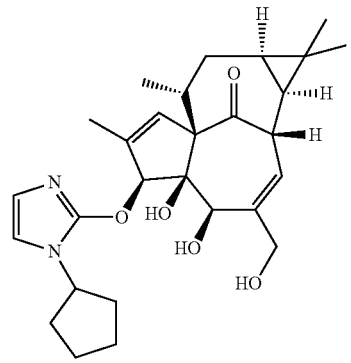 [SMILES: CC1=C[C@]23C(=O)[C@@H](C=C(CO)[C@@H](O)[C@]2(O)[C@H]1Oc1nccn1C1CCCC1)[C@H]1[C@@H](C[C@H]3C)C1(C)C]

Example 120

3-O-(1-Cyclopentylimidazol-2-yl)-ingenol (Compound 120)

Compound 120 was prepared according to Procedure d.
Starting material: Compound 220.
¹H NMR (300 MHz, CDCl₃) δ 6.55 (d, 1H), 6.52 (d, 1H), 6.07-6.05 (m, 1H), 6.04-6.02 (m, 1H), 5.18 (s, 1H), 6.46-6.42 (m, 1H), 6.07-6.05 (m, 1H), 6.04-6.02 (m, 1H), 5.18 (s, 1H), 4.46-4.41 (m, 1H), 4.18-4.06 (m, 4H), 2.62-2.56 (m, 1H), 2.30-2.21 (m, 1H), 2.13-2.06 (m, 2H), 1.85 (d, 3H), 1.83-1.66 (m, 7H), 1.09 (s, 3H), 1.04 (s, 3H), 1.01-0.94 (m, 4H), 0.72-0.65 (m, 1H).

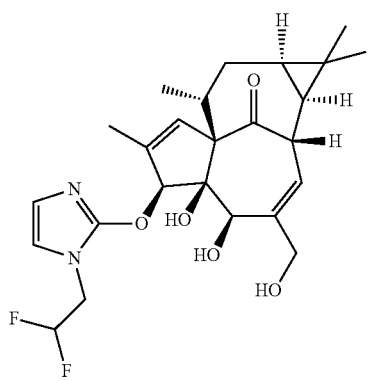 [SMILES: CC1=C[C@]23C(=O)[C@@H](C=C(CO)[C@@H](O)[C@]2(O)[C@H]1Oc1nccn1CC(F)F)[C@H]1[C@@H](C[C@H]3C)C1(C)C]

Example 121

3-O-(1-(2,2-Difluoroethyl)imidazol-2-yl)-ingenol (Compound 121)

Compound 121 was prepared according to Procedure d.
Starting material: Compound 221.

¹H NMR (300 MHz, CDCl₃) δ 6.60-6.59 (m, 2H), 6.10-6.08 (m, 1H), 6.05-6.03 (m, 1H), 5.94 (tt, 1H), 5.22 (s, 1H), 4.3 (bs, 1H), 4.19-4.04 (m, 6H), 2.7 (bs, 1H), 2.55-2.51 (m, 1H), 2.35 (s, 1H), 2.29-2.20 (m, 1H), 1.84 (d, 3H), 1.81-1.71 (m, 1H), 1.08 (s, 3H), 1.04 (s, 3H), 1.02-0.93 (m, 4H), 0.73-0.65 (m, 1H).

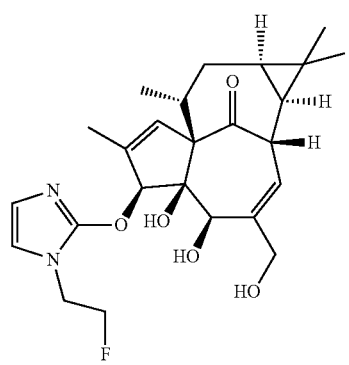 [SMILES: CC1=C[C@]23C(=O)[C@@H](C=C(CO)[C@@H](O)[C@]2(O)[C@H]1Oc1nccn1CCF)[C@H]1[C@@H](C[C@H]3C)C1(C)C]

Example 122

3-O-(1-(2-Fluoroethyl)imidazol-2-yl)-ingenol (Compound 122)

Compound 122 was prepared according to Procedure d.
Starting material: Compound 222.

¹H NMR (300 MHz, CDCl₃) δ 6.61 (m, 1H), 6.58 (d, 1H), 6.08-6.06 (m, 1H), 6.04-6.03 (m, 1H), 5.20 (s, 1H), 4.63 (dt, 2H), 4.4 (bs, 1H), 4.18-4.00 (m, 7H), 2.75 (bs, 1H), 2.57-2.51 (m, 1H), 2.29-2.20 (m, 1H), 1.84 (d, 3H), 1.80-1.71 (m, 1H), 1.09 (s, 3H), 1.04 (s, 3H), 1.02-0.94 (m, 4H), 0.72-0.65 (m, 1H).

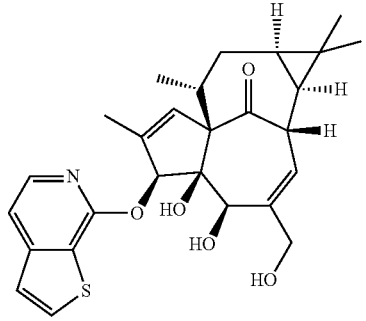 [SMILES: CC1=C[C@]23C(=O)[C@@H](C=C(CO)[C@@H](O)[C@]2(O)[C@H]1Oc1nccc2ccsc12)[C@H]1[C@@H](C[C@H]3C)C1(C)C]

Example 123

3-O-(Thieno[2,3-c]pyridine-7-yl)-ingenol (Compound 123)

Compound 123 was prepared according to Procedure d.
Starting material: Compound 223.

¹H NMR (300 MHz, CDCl₃) δ 7.93 (d, 1H), 7.73 (d, 1H), 7.40-7.37 (m, 2H), 6.10-6.06 (m, 2H), 5.78 (bs, 1H), 5.70 (s, 1H), 4.20-4.07 (m, 5H), 2.69-2.63 (m, 2H), 2.27-2.17 (m, 1H), 1.89 (d, 3H), 1.83-1.73 (m, 1H), 1.07 (s, 3H), 1.05-1.03 (m, 6H), 1.02-0.95 (m, 1H), 0.74-0.67 (m, 1H).

Example 124

3-O-(3-Methyl-2-pyridyl)-ingenol (Compound 124)

Compound 124 was prepared according to Procedure d.
Starting material: Compound 224.

¹H NMR (300 MHz, CDCl₃) δ 7.90-7.88 (m, 1H), 7.51-7.47 (m, 1H), 6.88 (dd, 1H), 6.06-6.04 (m, 1H), 6.03-6.02 (m, 1H), 5.94 (bs, 1H), 5.49 (s, 1H), 4.17-4.04 (m, 5H), 2.73 (bs, 1H), 2.65-2.59 (m, 1H), 2.26-2.17 (m, 4H), 1.84 (d, 3H), 1.82-1.72 (m, 1H), 1.09 (s, 3H), 1.04 (s, 3H), 1.02-0.96 (m, 4H), 0.73-0.66 (m, 1H).

63

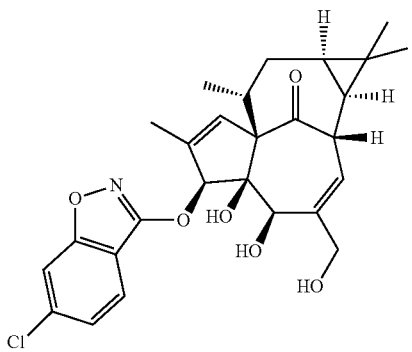 [SMILES: CC1=C[C@]23C(=O)[C@@H](C=C(CO)[C@@H](O)[C@]2(O)[C@H]1Oc1noc2cc(Cl)ccc12)[C@H]1[C@@H](C[C@H]3C)C1(C)C]

Example 125

3-O-(6-Chloro-1,2-benzoxazol-3-yl)-ingenol (Compound 125)

Compound 125 was prepared according to Procedure d.
Starting material: Compound 225.

¹H NMR (300 MHz, DMSO-d₆) δ 7.86-7.85 (m, 1H), 7.79 (d, 1H), 7.42 (dd, 1H), 6.04-6.02 (m, 1H), 5.90-5.88 (m, 1H), 5.77 (s, 1H), 5.48 (s, 1H), 5.37 (d, 1H), 4.63 (t, 1H), 4.21 (bd, 1H), 3.95-3.90 (m, 2H), 3.62 (d, 1H), 2.67-2.61 (m, 1H), 2.36-2.26 (m, 1H), 1.82 (d, 3H), 1.78-1.69 (m, 1H), 1.05 (s, 3H), 1.04 (s, 3H), 0.96 (d, 3H), 0.84-0.77 (m, 1H), 0.68-0.60 (m, 1H).

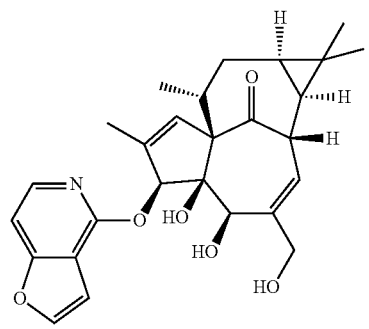 [SMILES: CC1=C[C@]23C(=O)[C@@H](C=C(CO)[C@@H](O)[C@]2(O)[C@H]1Oc1nccc2occc12)[C@H]1[C@@H](C[C@H]3C)C1(C)C]

Example 126

3-O-(Furo[3,2-c]pyridine-4-yl)-ingenol (Compound 126)

Compound 126 was prepared according to Procedure d.
Starting material: Compound 226.

¹H NMR (300 MHz, CDCl₃) δ 7.90 (d, 1H), 7.63 (d, 1H), 7.18 (dd, 1H), 6.90 (dd, 1H), 6.09-6.00 (m, 3H), 5.64 (s, 1H), 4.21-4.06 (m, 5H), 2.72-2.61 (m, 2H), 2.27-2.19 (m, 1H), 1.87 (d, 3H), 1.82-1.72 (m, 1H), 1.06 (s, 3H), 1.04-1.01 (m, 6H), 1.01-0.95 (m, 1H), 0.74-0.66 (m, 1H).

64

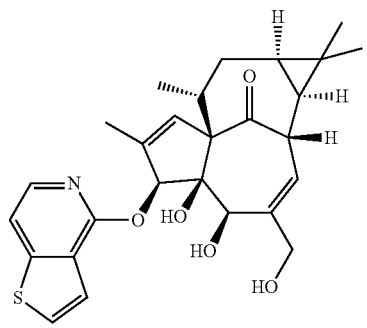 [SMILES: CC1=C[C@]23C(=O)[C@@H](C=C(CO)[C@@H](O)[C@]2(O)[C@H]1Oc1nccc2sccc12)[C@H]1[C@@H](C[C@H]3C)C1(C)C]

Example 127

3-O-(Thieno[3,2-c]pyridine-4-yl)-ingenol (Compound 127)

Compound 127 was prepared according to Procedure d.
Starting material: Compound 227.

¹H NMR (300 MHz, CDCl₃) δ 7.87 (d, 1H), 7.55-7.53 (m, 1H), 7.48-7.45 (m, 2H), 6.10-6.00 (m, 3H), 5.68 (s, 1H), 4.23-4.00 (m, 5H), 2.71-2.61 (m, 2H), 2.26-2.17 (m, 1H), 1.87 (d, 3H), 1.82-1.72 (m, 1H), 1.06 (s, 3H), 1.04-1.02 (m, 6H), 1.02-0.96 (m, 1H), 0.74-0.66 (m, 1H).

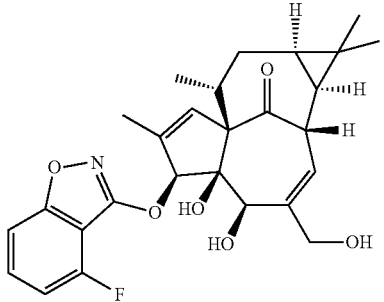 [SMILES: CC1=C[C@]23C(=O)[C@@H](C=C(CO)[C@@H](O)[C@]2(O)[C@H]1Oc1noc2cccc(F)c12)[C@H]1[C@@H](C[C@H]3C)C1(C)C]

Example 128

3-O-(4-Fluoro-1,2-benzoxazol-3-yl)-ingenol (Compound 128)

Compound 128 was prepared according to Procedure d.
Starting material: Compound 228

¹H NMR (300 MHz, CDCl₃) δ 7.49 (td, J=8.3, 5.1 Hz, 1H), 7.23 (d, J=9.1 Hz, 1H), 6.91 (dd, J=9.1, 8.1 Hz, 1H), 6.17-6.13 (m, 1H), 6.05-6.01 (m, 1H), 5.68 (s, 1H), 4.52 (d, J=5.9 Hz, 1H), 4.28-4.02 (m, 4H), 3.84 (s, 1H), 2.89-2.76 (m, 1H), 2.76-2.63 (m, 1H), 2.28 (ddd, J=15.8, 8.9, 3.1 Hz, 1H), 1.91 (d, J=1.7 Hz, 3H), 1.80 (dt, J=15.8, 5.7 Hz, 1H), 1.11-0.99 (m, 9H), 0.98-0.88 (m, 1H), 0.70 (td, J=8.7, 6.2 Hz, 1H).

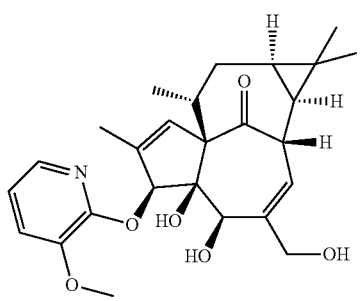 [SMILES: COc1cccnc1O[C@H]1C(C)=C[C@]23C(=O)[C@@H](C=C(CO)[C@@H](O)[C@]12O)[C@H]1[C@@H](C[C@H]3C)C1(C)C]

Example 129

3-O-(3-Methoxy-pyridin-2-yl)-ingenol (Compound 129)

Compound 129 was prepared according to Procedure d.
Starting material: Compound 229

$^1$H NMR (300 MHz, CDCl$_3$) δ 7.66 (dd, J=5.0, 1.5 Hz, 1H), 7.14 (dd, J=7.7, 1.5 Hz, 1H), 6.93 (dd, J=7.9, 5.1 Hz, 1H), 6.09-6.02 (m, 2H), 5.57 (s, 1H), 5.00 (bs, 1H), 4.31 (bs, 1H), 4.17-4.05 (m, 4H), 3.87 (s, 3H), 2.90-2.50 (m, 2H), 2.27 (ddd, J=15.7, 8.4, 3.1 Hz, 1H), 1.88 (d, J=1.5 Hz, 3H), 1.79 (dt, J=15.7, 6.0 Hz, 1H), 1.09 (s, 3H), 1.05 (s, 3H), 1.02 (d, J=7.1 Hz, 3H), 1.05-0.95 (m, 1H), 0.71 (td, J=8.3, 6.2 Hz, 1H).

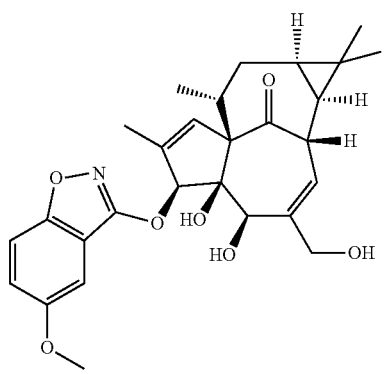 [SMILES: COc1ccc2onc(O[C@H]3C(C)=C[C@]45C(=O)[C@@H](C=C(CO)[C@@H](O)[C@]34O)[C@H]3[C@@H](C[C@H]5C)C3(C)C)c2c1]

Example 130

3-O-(5-Methoxy-1,2-benzoxazol-3-yl)-ingenol (Compound 130)

Compound 130 was prepared according to Procedure d.
Starting material: Compound 230

$^1$H NMR (300 MHz, CDCl$_3$) δ 7.35 (d, J=9.3 Hz, 1H), 7.18 (dd, J=9.1, 2.4 Hz, 1H), 7.01 (d, J=2.4 Hz, 1H), 6.17 (q, J=1.7 Hz, 1H), 6.07 (dd, J=4.7, 1.4 Hz, 1H), 5.58 (s, 1H), 4.46 (d, J=4.9 Hz, 1H), 4.29-4.01 (m, 4H), 3.87 (s, 3H), 3.80 (s, 1H), 3.55-3.45 (m, 1H), 2.75-2.60 (m, 1H), 2.40-2.20 (m, 1H), 1.90 (d, J=1.6 Hz, 3H), 1.79 (ddd, J=15.7, 6.2, 4.9 Hz, 1H), 1.13-1.02 (m, 9H), 0.96 (dd, J=11.6, 8.4 Hz, 1H), 0.71 (td, J=8.8, 6.3 Hz, 1H).

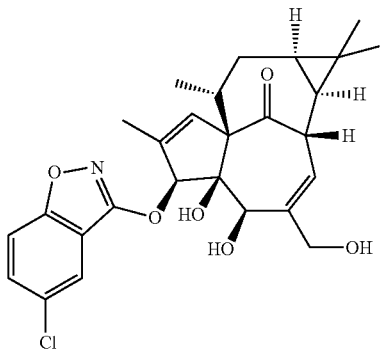 [SMILES: CC1=C[C@]23C(=O)[C@@H](C=C(CO)[C@@H](O)[C@]2(O)[C@H]1Oc1noc2ccc(Cl)cc12)[C@H]1[C@@H](C[C@H]3C)C1(C)C]

Example 131

3-O-(5-Chloro-1,2-benzoxazol-3-yl)-ingenol (Compound 131)

Compound 131 was prepared according to Procedure d.
Starting material: Compound 231

$^1$H NMR (300 MHz, CDCl$_3$) δ 7.67 (d, J=2.1 Hz, 1H), 7.51 (dd, J=9.0, 2.1 Hz, 1H), 7.39 (d, J=8.9 Hz, 1H), 6.18 (q, J=1.5 Hz, 1H), 6.08 (dd, J=4.8, 1.4 Hz, 1H), 5.63 (s, 1H), 4.42 (d, J=4.7 Hz, 1H), 4.28-4.03 (m, 4H), 3.74 (s, 1H), 2.70-2.56 (m, 1H), 2.29 (ddd, J=15.9, 9.2, 3.1 Hz, 1H), 2.18 (t, J=6.0 Hz, 1H), 1.89 (d, J=1.6 Hz, 3H), 1.81 (ddd, J=15.9, 6.3, 4.9 Hz, 1H), 1.13-1.01 (m, 9H), 1.02-0.90 (m, 1H), 0.72 (td, J=8.9, 6.3 Hz, 1H).

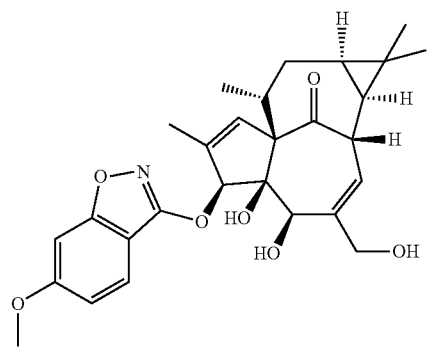 [SMILES: COc1ccc2c(O[C@H]3C(C)=C[C@]45C(=O)[C@@H](C=C(CO)[C@@H](O)[C@]34O)[C@H]3[C@@H](C[C@H]5C)C3(C)C)noc2c1]

Example 132

3-O-(6-Methoxy-1,2-benzoxazol-3-yl)-ingenol (Compound 132)

Compound 132 was prepared according to Procedure d.
Starting material: Compound 232

$^1$H NMR (300 MHz, DMSO-d6) δ 7.61 (d, J=8.9 Hz, 1H), 7.16 (d, J=2.1 Hz, 1H), 6.93 (dd, J=8.8, 2.0 Hz, 1H), 6.25-5.97 (m, 1H), 5.92-5.86 (m, 1H), 5.71 (s, 1H), 5.42-5.31 (m, 2H), 4.64 (t, J=5.6 Hz, 1H), 4.27-4.16 (m, 1H), 4.00-3.80 (m, 4H), 3.66-3.56 (m, 1H), 3.17 (d, J=5.2 Hz, 1H), 2.73-2.59 (m, 1H), 2.39-2.24 (m, 1H), 1.81 (d, J=1.5 Hz, 3H), 1.79-1.65 (m, 1H), 1.05 (s, 3H), 1.04 (s, 3H), 0.95 (d, J=7.0 Hz, 3H), 0.80 (dd, J=11.8, 8.4 Hz, 1H), 0.64 (td, J=8.7, 6.2 Hz, 1H).

Example 133

3-O-(5-Isopropyl-1,2,4-oxadiazol-3-yl)-ingenol (Compound 133)

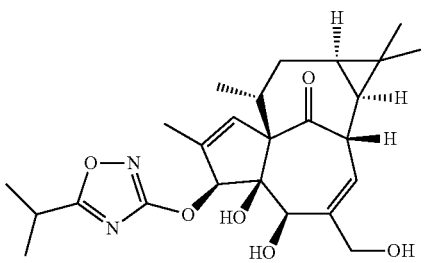 [SMILES: CC1=C[C@]23C(=O)[C@@H](C=C(CO)[C@@H](O)[C@]2(O)[C@H]1Oc1noc(C(C)C)n1)[C@H]1[C@@H](C[C@H]3C)C1(C)C]

Compound 133 was prepared according to Procedure d.
Starting material: Compound 233
$^1$H NMR (300 MHz, CDCl$_3$) δ 6.13 (q, J=1.6 Hz, 1H), 6.05 (dd, J=4.6, 1.6 Hz, 1H), 5.46 (s, 1H), 4.24-4.05 (m, 4H), 3.98 (d, J=6.1 Hz, 1H), 3.91 (s, 1H), 3.12 (p, J=6.9 Hz, 1H), 2.70-2.50 (m, 1H), 2.50-2.30 (m, 1H), 2.30-2.20 (m, 1H), 1.87 (d, J=1.6 Hz, 3H), 1.84-1.63 (m, 1H), 1.38 (m, 6H), 1.08 (s, 3H), 1.05 (s, 3H), 0.99 (d, J=7.1 Hz, 3H), 1.00-0.85 (m, 1H), 0.72 (dd, J=9.0, 6.1 Hz, 1H).

Example 1

Neutrophil Oxidative Burst

PMN's (polymorphonuclear leukocytes) are isolated and purified from fresh buffy coats by sequential sedimentation, density centrifugation and lysis of contaminating erythrocytes. In brief, buffy coats are incubated with 2% methocel for 30-45 min to differentially sediment red blood cells. The leukocyte-rich supernatant is transferred to lymphoprep tubes to remove mononuclear cells by density centrifugation (400× g, 30 min). The pellet is resuspended and any remaining erythrocytes lysed using 0.2% NaCl for 30 sec before restoring isotonicity by the addition of 1.2% NaCl. This step is repeated until the cell pellet appears relatively free of red blood cells. Cells are resuspended in DPBS (Dulbecco's Phosphate Buffered Saline) (w.o. Ca$^{2+}$, Mg$^{2+}$) and the concentration adjusted to 1.4×10$^6$ cells/ml in HBSS (Hanks Balanced Salt solution) (w Ca$^{2+}$, Mg$^{2+}$) containing 0.1% BSA (Bovine Serum Albumin) and 5 mM glucose just prior to assay initiation. Titrated reference and test compounds are pre-mixed with HE (Hydroethidine) (10 µM final assay concentration) before addition to 96-well plates containing 2.5×10$^5$ cells. Following 40 min incubation at rt, changes in the respiratory burst is estimated by measuring fluorescence at 579 nm (excitation: 485 nm) using an Envision plate reader.

Test compound titration curves are fitted to a four-parameter sigmoidal curve after normalizing the effect of the test compound to the effect of the positive control (5×10$^{-7}$ M PEP0005). Rel EC$_{50}$ denotes the concentration of test compound producing an effect that is midway between the fitted top and bottom. Abs EC$_{50}$ is the concentration of test compound that provokes a response corresponding to 50% of the maximal effect associated with the positive control (5×10$^{-7}$ M PEP0005).

Example 2

HeKa Cytokine Release (IL-8)

Primary human epidermal keratinocytes, HeKa, are seeded (10.000 cells/well) in 96-well plates the day before the assay. Test compounds are diluted in DMSO (dimethyl sulfoxide) and further diluted in assay medium and pipetted into wells of 96 well-plates containing HeKa cells. The plates are incubated for 6 h at 37° C. in humidified air with 5% CO$_2$. Plates are centrifuged briefly to spin down cells at 4° C., the supernatant is removed and analysed by Meso Scale Discovery (MSD) 4-spot cytokine assay (Pro-inflammatory II Ultra Sensitive kit, MSD, MD, USA). The MSD assay employs a sandwich immunoassay format where capture antibodies are coated in a patterned array on the bottom of the wells of a 4-Spot-Multi-MSD plate. Standard samples are incubated in the MULTI-SPOT plates as well, and the cytokine (IL-8) binds to its corresponding capture antibody spot. The cytokine level is quantitated on a SECTOR™ Imager using a cytokine-specific Detection Antibody labelled with MSD SULFO-TAG™ reagent.

Test compound titration curves are fitted to a four-parameter sigmoidal curve after normalizing the effect of the test compound to the effect of the positive control (1.5×10$^{-7}$ M PEP0005). Rel EC$_{50}$ denotes the concentration of test compound producing an effect that is midway between the fitted top and bottom. Abs EC$_{50}$ is the concentration of test compound that provokes a response corresponding to 50% of the maximal effect associated with the positive control (1.5×10$^{-7}$ M PEP0005).

Example 3

Necrosis Assay

HeLa cells (ATCC CCL-002) were grown in minimal essential medium (Invitrogen catalog no. 42360) containing 10% fetal bovine serum, 100 IU/ml penicillin and 100 µg/ml streptomycin. 4,000-6,000 cells were seeded into 96-well black ViewPlates-plates, clear bottom, (Perkin Elmer) in 100 µl medium and incubated overnight. Compounds were dissolved and pre-diluted in DMSO in 96-well polypropylene plates (Greiner) in a concentration range of 15 µM to 600 µM. At the time of the experiment cell plates were placed on heating blocks at 37° C., medium was removed and 40 µl fresh, pre-warmed medium was added per well. Cells were incubated for 15 min before addition of compounds. In parallel, 3 µl of compounds were diluted with 197 µl growth medium on a Tecan freedom-EVO pipetting station using 250 µl/s pipetting speed, in order to ensure effective mixing of the highly concentrated compound solutions with the aqueous phase.

These pre-dilution plates were then equilibrated on heating blocks at 37° C. for 10 min. 80 µl pre-diluted compound were transferred manually to the corresponding wells containing HeLa cells yielding compound concentrations of 10 µM to 400 µM. Control conditions were 1% DMSO in growth medium (100% viability) and 400 µM ingenol mebutate in growth medium (0% viability). Plates were incubated on the heating blocks at 37° C. for 30 min. At the end of the incubation 10 µl PrestoBlue reagent (Invitrogen) were added to each well, plates were sealed with black seal, followed by incubation at 37° C. for 10 min with gentle shaking (150 rpm). Subsequently, plates were placed at room temperature for 20-30 min. Plates were read immediately after on an Envision Fluorescence reader (Perkin Elmer) with excitation at 535 nm and emission at 630 nm. Test compound titration curves were fitted to a four-parameter sigmoidal curve after normalizing the effect of the test compound to the effect of the positive control (4 10$^{-4}$ M PEP0005/ingenol mebutate). Abs $EC_{50}$ denotes the concentration of test compound producing 50% effect.

Compounds of the present invention were tested in the neutrophil oxidative burst assay according to the description in example 1, in the HeKa cytokine release assay according to the description in example 2 and in the necrosis assay according to the description in example 3.

Compounds of the present invention display Rel $EC_{50}$ values below 10000 nM in the neutrophil oxidative burst assay and Rel $EC_{50}$ values below 10000 nM in the HeKa cytokine release assay.

Neutrophil oxidative burst Rel $EC_{50}$ ranges
* indicates that Rel $EC_{50}$ values are ≥100 nM
** indicates that Rel $EC_{50}$ values are ≥20 nM and <100 nM
*** indicates that Rel $EC_{50}$ values are <20 nM HeKa cytokine release (IL-8) Rel $EC_{50}$ ranges
* indicates that Rel $EC_{50}$ values are ≥100 nM
** indicates that Rel $EC_{50}$ values are ≥20 nM and <100 nM
*** indicates that Rel $EC_{50}$ values are <20 nM HeLa Necrosis $EC_{50}$ ranges
* indicates that $EC_{50}$ values are ≥350 μM
** indicates that $EC_{50}$ values are ≥150 μM and <350 μM
*** indicates that $EC_{50}$ values are <150 μM Results are shown in the table below.

| Compound name and number | Neutrophil oxidative burst Rel $EC_{50}$ range | HeKa cytokine release (IL-8) Rel $EC_{50}$ range | HeLa necrosis $EC_{50}$ range |
|---|---|---|---|
| 3-O-(6-Chloro-5-methyl-pyrimidin-4-yl)-ingenol (Compound 101) | ** | *** | *** |
| 3-O-(1,2-Benzoxazol-3-yl)-ingenol (Compound 102) | *** | *** | ** |
| 3-O-(5-(Trifluoromethyl)-2-pyridyl)-ingenol (Compound 103) | nd | ** | ** |
| 3-O-(5-Allyl-6-chloro-pyrimidin-4-yl)-ingenol (Compound 104) | ** | *** | *** |
| 3-O-(3-Formyl-2-pyridyl)-ingenol (Compound 105) | * | * | * |
| 3-O-(2-Pyridyl)-ingenol (Compound 106) | * | ** | * |
| 3-O-(1-Methylindazol-3-yl)-ingenol (Compound 107) | * | * | ** |
| 3-O-(1-Methylimidazol-2-yl)-ingenol (Compound 108) | * | * | * |
| 3-O-(1-Allylimidazol-2-yl)-ingenol (Compound 109) | ** | nd | * |
| 3-O-(5-(Trifluoromethyl)-pyrimidin-2-yl)-ingenol (Compound 110) | * | * | * |
| 3-O-(4-Bromo-2-pyridyl)-ingenol (Compound 111) | ** | ** | ** |
| 3-O-(3-Fluoro-2-pyridyl)-ingenol (Compound 112) | ** | * | * |
| 3-O-(4-(Trifluoromethyl)-2-pyridyl)-ingenol (Compound 113) | ** | ** | ** |
| 3-O-(4-(Trifluoromethyl)-pyrimidin-2-yl)-ingenol (Compound 114) | * | * | * |
| 3-O-(3-Chloro-2-pyridyl)-ingenol (Compound 115) | ** | ** | ** |
| 3-O-(3-Cyano-2-pyridyl)-ingenol (Compound 116) | ** | * | * |
| 3-O-(6-(Trifluoromethyl)-2-pyridyl)-ingenol (Compound 117) | * | * | * |
| 3-O-(3-(Trifluoromethyl)-2-pyridyl)-ingenol (Compound 118) | *** | ** | *** |
| 3-O-(1-Isoquinolyl)-ingenol (Compound 119) | ** | *** | ** |
| 3-O-(1-Cyclopentylimidazol-2-yl)-ingenol (Compound 120) | *** | *** | ** |
| 3-O-(1-(2,2-Difluoroethyl)imidazol-2-yl)-ingenol (Compound 121) | ** | * | nd |
| 3-O-(1-(2-Fluoroethyl)imidazol-2-yl)-ingenol (Compound 122) | * | * | nd |
| 3-O-(Thieno[2,3-c]pyridine-7-yl)-ingenol (Compound 123) | ** | *** | * |
| 3-O-(3-Methyl-2-pyridyl)-ingenol (Compound 124) | * | * | * |
| 3-O-(6-Chloro-1,2-benzoxazol-3-yl)-ingenol (Compound 125) | *** | *** | *** |
| 3-O-(Furo[3,2-c]pyridine-4-yl)-ingenol (Compound 126) | ** | nd | ** |
| 3-O-(Thieno[3,2-c]pyridine-4-yl)-ingenol (Compound 127) | ** | ** | ** |
| 3-O-(4-Fluoro-1,2-benzoxazol-3-yl)-ingenol (Compound 128) | *** | *** | ** |

-continued

| Compound name and number | Neutrophil oxidative burst Rel $EC_{50}$ range | HeKa cytokine release (IL-8) Rel $EC_{50}$ range | HeLa necrosis $EC_{50}$ range |
|---|---|---|---|
| 3-O-(3-Methoxy-pyridin-2-yl)-ingenol (Compound 129) | * | * | * |
| 3-O-(5-Methoxy-1,2-benzoxazol-3-yl)-ingenol (Compound 130) | *** | *** | ** |
| 3-O-(5-Chloro-1,2-benzoxazol-3-yl)-ingenol (Compound 131) | *** | *** | *** |
| 3-O-(6-Methoxy-1,2-benzoxazol-3-yl)-ingenol (Compound 132) | *** | *** | * |
| 3-O-(5-Isopropyl-1,2,4-oxadiazol-3-yl)-ingenol (Compound 133) | ** | ** | * |

The invention claimed is:

1. A compound according to the general formula I

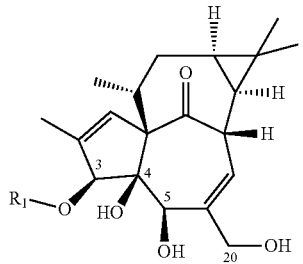

I wherein $R_1$ represents heteroaryl, and wherein $R_1$ is optionally substituted with one or more substituents independently selected from $R_2$;

wherein $R_2$ represents cyano or halogen;

or $R_2$ represents $(C_1-C_6)$alkyl, $(C_2-C_6)$alkenyl, $(C_1-C_6)$alkoxy, $(C_3-C_6)$cycloalkyl, halo$(C_1-C_6)$alkyloxy, heterocycloalkyl, aryl or heteroaryl; said $(C_1-C_6)$alkyl optionally being substituted with one or more substituents independently selected from the group consisting of halogen, cyano, hydroxyl and oxo;

or $R_2$ represents —$NR_aCOR_b$, —$CONR_aR_b$, —$COOR_a$, —$COOR_a$, —$OR_a$, —$COONR_aR_b$, —$NR_aCOOR_b$, —$NR_aSO_2R_b$, —$SO_2NR_aR_b$, —$SO_2R_a$, —$S(O)R_a$ or —$NR_aR_b$;

wherein $R_a$ and $R_b$ are each independently selected from the group consisting of hydrogen, $(C_1-C_4)$alkyl, halo$(C_1-C_4)$alkyl, hydroxy$(C_1-C_4)$alkyl, cyano$(C_1-C_4)$alkyl, aryl, heteroaryl, $(C_3-C_6)$cycloalkyl and heterocycloalkyl;

or two adjacent $R_2$'s join together to form a 5-7 membered non-aromatic carbocyclic or heterocyclic ring together with the carbon or nitrogen atoms to which they are attached;

and pharmaceutically acceptable salts, hydrates, solvates or pharmaceutically acceptable and physiologically cleavable esters thereof.

2. The compound according to claim 1 wherein $R_1$ represents heteroaryl; said heteroaryl optionally being substituted with one or more substituents independently selected from $R_2$; and wherein said heteroaryl is selected from the group consisting of

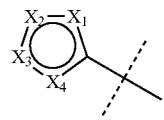

G1

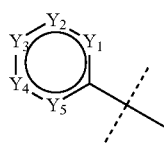

G2

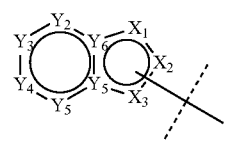

G3

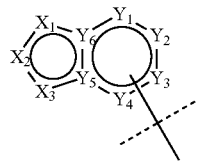

G4

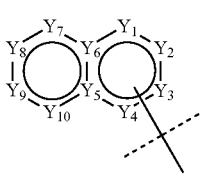

G5 wherein $X_1$, $X_2$, $X_3$ and $X_4$ are each independently selected from the group consisting of C, CH, N, NH, S and O; and wherein $Y_1$, $Y_2$, $Y_3$, $Y_4$, $Y_5$, $Y_6$, $Y_7$, $Y_8$, $Y_9$ and $Y_{10}$ are each independently selected from the group consisting of C, CH and N.

3. The compound according to claim 2, wherein $R_1$ represents $G_1$ and wherein at least one of $X_1$ or $X_4$ is selected from the group consisting of N, NH, S and O; or $R_1$ represents $G_2$ and wherein at least one of $Y_1$ or $Y_5$ represents N; or $R_1$ represents $G_3$ and wherein the point of attachment to formula I occurs through $X_1$ or $X_3$ and wherein $X_2$ is selected from the group consisting of N, NH, S and O; or $R_1$ represents $G_3$ and wherein the point of attachment to formula I occurs through $X_2$ and wherein at least one of $X_1$ and $X_3$ is selected from the group consisting of N, NH, S and O; or R₁ represents G₄ and wherein the point of attachment to formula I occurs through Y₁ and wherein Y₂ represents N; or R₁ represents G₄ and wherein the point of attachment to formula I occurs through Y₂ and wherein at least one of Y₁ and Y₃ represents N; or R₁ represents G₅ and wherein the point of attachment to formula I occurs through Y₁ and wherein Y₂ represents N; or R₁ represents G₅ and wherein the point of attachment to formula I occurs through Y₂ and wherein at least one of Y₁ and Y₃ represents N.

4. The compound according to claim 2, wherein

R₁ represents G₁ and wherein one X₁ or X₄ is selected from the group consisting of N, NH, S and O and wherein the other X₁ or X₄ is substituted with R₂; or R₁ represents G₂ and wherein one Y₁ or Y₅ represents N, and wherein the other Y₁ or Y₅ is substituted with R₂; or R₁ represents G₃ and wherein the point of attachment to formula I occurs through X₁ or X₃ and wherein X₂ is selected from the group consisting of N, NH, S and O; or R₁ represents G₄ and wherein the point of attachment to formula I occurs through Y₁ and wherein Y₂ represents N; or R₁ represents G₅ and wherein the point of attachment to formula I occurs through Y₁ and wherein Y₂ represents N.

5. The compound according to claim 1 wherein R₁ represents oxazolyl, isoxazolyl, thiazolyl, isothiazolyl, imidazolyl, pyrazolyl, pyridyl, pyrimidinyl, pyrazinyl, pyridazinyl, triazinyl, isoquinolinyl, benzoxazolyl, indazolyl, thienopyridyl, furopyridyl or oxadiazolyl.

6. The compound according to claim 1 wherein R₂ represents halogen, cyano, $(C_1\text{-}C_4)$alkyl, halo$(C_1\text{-}C_4)$alkyl, $(C_2\text{-}C_6)$alkenyl, $(C_1\text{-}C_6)$alkoxy or $(C_3\text{-}C_6)$cycloalkyl.

7. The compound according to claim 1 wherein R₂ represents methyl, trifluoromethyl, trifluoroethyl, propenyl, bromo, chloro, fluoro, cyano, methoxy, isopropyl, cyclopentyl, difluoroethyl or fluoroethyl.

8. The compound according to claim 1 selected from the group consisting of:
3-O-(6-Chloro-5-methyl-pyrimidin-4-yl)-ingenol,
3-O-(1,2-Benzoxazol-3-yl)-ingenol,
3-O-(5-(Trifluoromethyl)-2-pyridyl)-ingenol,
3-O-(5-Allyl-6-chloro-pyrimidin-4-yl)-ingenol,
3-O-(3-Formyl-2-pyridyl)-ingenol,
3-O-(2-Pyridyl)-ingenol,
3-O-(1-Methylindazol-3-yl)-ingenol,
3-O-(1-Methylimidazol-2-yl)-ingenol,
3-O-(1-Allylimidazol-2-yl)-ingenol,
3-O-(5-(Trifluoromethyl)-pyrimidin-2-yl)-ingenol,
3-O-(4-Bromo-2-pyridyl)-ingenol,
3-O-(3-Fluoro-2-pyridyl)-ingenol,
3-O-(4-(Trifluoromethyl)-2-pyridyl)-ingenol,
3-O-(4-(Trifluoromethyl)-pyrimidin-2-yl)-ingenol,
3-O-(3-Chloro-2-pyridyl)-ingenol,
3-O-(3-Cyano-2-pyridyl)-ingenol,
3-O-(6-(Trifluoromethyl)-2-pyridyl)-ingenol,
3-O-(3-(Trifluoromethyl)-2-pyridyl)-ingenol,
3-O-(1-Isoquinolyl)-ingenol,
3-O-(1-Cyclopentylimidazol-2-yl)-ingenol,
3-O-(1-(2,2-Difluoroethyl)imidazol-2-yl)-ingenol,
3-O-(1-(2-Fluoroethyl)imidazol-2-yl)-ingenol,
3-O-(Thieno[2,3-c]pyridine-7-yl)-ingenol,
3-O-(3-Methyl-2-pyridyl)-ingenol,
3-O-(6-Chloro-1,2-benzoxazol-3-yl)-ingenol,
3-O-(Furo[3,2-c]pyridine-4-yl)-ingenol,
3-O-(Thieno[3,2-c]pyridine-4-yl)-ingenol,
3-O-(4-Fluoro-1,2-benzoxazol-3-yl)-ingenol,
3-O-(3-Methoxy-pyridin-2-yl)-ingenol,
3-O-(5-Methoxy-1,2-benzoxazol-3-yl)-ingenol,
3-O-(5-Chloro-1,2-benzoxazol-3-yl)-ingenol,
3-O-(6-Methoxy-1,2-benzoxazol-3-yl)-ingenol, and
3-O-(5-Isopropyl-1,2,4-oxadiazol-3-yl)-ingenol, and pharmaceutically acceptable salts, hydrates, and solvates or pharmaceutically acceptable and physiologically cleavable esters thereof.

9. A method of ameliorating a disorder or disease which comprises administering to a subject in need thereof a compound according to claim 1, optionally together with a pharmaceutically acceptable carrier or one or more excipients, wherein the disorder or disease is selected from cutaneous warts, genital warts, actinic keratosis, squamous cell carcinoma (SCC), basal cell carcinoma (BCC), lentigo maligna, cervical intraepithelial neoplasia, anal intraepithelial neoplasia or vulva intraepithelial neoplasia.

10. The method according to claim 9 wherein the disorder or disease is actinic keratosis.

11. A method for ameliorating cosmetic indications which comprises administering to a subject in need thereof a compound according to claim 1, optionally together with a pharmaceutically acceptable carrier or one or more excipients.

12. The method according to claim 11 wherein the cosmetic indication is selected from photodamaged skin or seborrheic keratosis.

13. A pharmaceutical composition comprising a compound according to claim 1 or a pharmaceutically acceptable stereoisomer, salt or in vivo hydrolysable ester thereof together with a pharmaceutically acceptable vehicle or excipient.

14. The pharmaceutical composition according to claim 13, wherein the composition is suitable for topical administration.

15. A pharmaceutical composition comprising a compound according to claim 1 or a pharmaceutically acceptable stereoisomer, salt or in vivo hydrolysable ester thereof in combination with one or more other therapeutically active agents.

16. A compound selected from the group consisting of:
3-O-(6-Chloro-5-methyl-pyrimidin-4-yl)-ingenol-5,20-acetonide,
3-O-(1,2-Benzoxazol-3-yl)-ingenol-5,20-acetonide,
3-O-(5-(Trifluoromethyl)-2-pyridyl)-ingenol-5,20-acetonide,
3-O-(5-Allyl-6-chloro-pyrimidin-4-yl)-ingenol-5,20-acetonide,
3-O-(3-Formyl-2-pyridyl)-ingenol-5,20-acetonide,
3-O-(2-Pyridyl)-ingenol-5,20-acetonide,
3-O-(1-Methylindazol-3-yl)-ingenol-5,20-acetonide,
3-O-(1-Methylimidazol-2-yl)-ingenol-5,20-acetonide,
3-O-(1-Allylimidazol-2-yl)-ingenol-5,20-acetonide,
3-O-(5-(Trifluoromethyl)-pyrimidin-2-yl)-ingenol-5,20-acetonide,
3-O-(4-Bromo-2-pyridyl)-ingenol-5,20-acetonide,
3-O-(3-Fluoro-2-pyridyl)-ingenol-5,20-acetonide,
3-O-(4-(Trifluoromethyl)-2-pyridyl)-ingenol-5,20-acetonide,
3-O-(4-(Trifluoromethyl)-pyrimidin-2-yl)-ingenol-5,20-acetonide,
3-O-(3-Chloro-2-pyridyl)-ingenol-5,20-acetonide,
3-O-(3-Cyano-2-pyridyl)-ingenol-5,20-acetonide,
3-O-(6-(Trifluoromethyl)-2-pyridyl)-ingenol-5,20-acetonide, 3-O-(3-(Trifluoromethyl)-2-pyridyl)-ingenol-5,20-acetonide,
3-O-(1-Isoquinolyl)-ingenol-5,20-acetonide,
3-O-(1-Cyclopentylimidazol-2-yl)-ingenol-5,20-acetonide,
3-O-(1-(2,2-Difluoroethyl)imidazol-2-yl)-ingenol-5,20-acetonide,
3-O-(1-(2-Fluoroethyl)imidazol-2-yl)-ingenol-5,20-acetonide,
3-O-(Thieno[2,3-c]pyridine-7-yl)-ingenol-5,20-acetonide,
3-O-(3-Methyl-2-pyridyl)-ingenol-5,20-acetonide,
3-O-(6-Chloro-1,2-benzoxazol-3-yl)-ingenol-5,20-acetonide,
3-O-(Furo[3,2-c]pyridine-4-yl)-ingenol-5,20-acetonide,
3-O-(Thieno[3,2-c]pyridine-4-yl)-ingenol-5,20-acetonide,
3-O-(4-Fluoro-1,2-benzoxazol-3-yl)-ingenol-5,20-acetonide,
3-O-(3-Methoxy-pyridin-2-yl)-ingenol-5,20-acetonide,
3-O-(5-Methoxy-1,2-benzoxazol-3-yl)-ingenol-5,20-acetonide,
3-O-(5-Chloro-1,2-benzoxazol-3-yl)-ingenol-5,20-acetonide,
3-O-(6-Methoxy-1,2-benzoxazol-3-yl)-ingenol-5,20-acetonide, and
3-O-(5-Isopropyl-1,2,4-oxadiazol-3-yl)-ingenol-5,20-acetonide.

17. The compound 3-O-(1,2-benzoxazol-3-yl)-ingenol.

18. The compound 3-O-(5-methoxy-1,2-benzoxazol-3-yl)-ingenol.

19. The compound 3-O-(5-chloro-1,2-benzoxazol-3-yl)-ingenol.

* * * * *